(12) United States Patent
Jackson

(10) Patent No.: US 12,127,863 B2
(45) Date of Patent: Oct. 29, 2024

(54) PATIENT POSITIONING SUPPORT STRUCTURE

(71) Applicant: WARSAW ORTHOPEDIC INC., Warsaw, IN (US)

(72) Inventor: Roger P. Jackson, Prairie Village, KS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 256 days.

(21) Appl. No.: 17/308,337

(22) Filed: May 5, 2021

(65) Prior Publication Data
US 2021/0282726 A1    Sep. 16, 2021

Related U.S. Application Data

(60) Division of application No. 15/479,007, filed on Apr. 4, 2017, now Pat. No. 11,051,770, which is a
(Continued)

(51) Int. Cl.
*A61G 13/02* (2006.01)
*A61B 6/04* (2006.01)
(Continued)

(52) U.S. Cl.
CPC ............ *A61B 6/0407* (2013.01); *A61G 7/001* (2013.01); *A61G 7/008* (2013.01);
(Continued)

(58) Field of Classification Search
CPC ........ A61G 7/015; A61G 7/018; A61G 13/02; A61G 13/004; A61G 13/04; A61G 13/06; A61G 13/08; A61G 13/10
See application file for complete search history.

(56) References Cited

U.S. PATENT DOCUMENTS 377,377 A    2/1888    Ferry
392,743 A    11/1888   Millen
(Continued)

FOREIGN PATENT DOCUMENTS

CN    2467091 Y    12/2001
EP    2226010 B1   6/2014
(Continued)

OTHER PUBLICATIONS

U.S. Appl. No. 15/421,994, filed Feb. 1, 2017, Jackson et al.
(Continued)

*Primary Examiner* — Justin C Mikowski
*Assistant Examiner* — Ifeolu A Adeboyejo
(74) *Attorney, Agent, or Firm* — Sorell, Lenna & Schmidt, LLP

(57) ABSTRACT

A patient support system includes independently adjustable end columns supporting a centrally hinged, jointed or breaking patient support structure. At least one column includes a powered rotation assembly. The patient support includes at least two sections. A coordinated drive system provides for both upwardly and downwardly breaking or jointed orientations of the two sections in various inclined and tilted positions. Cable, cantilevered and pull-rod systems are included.

20 Claims, 37 Drawing Sheets

Related U.S. Application Data continuation of application No. 14/538,310, filed on Nov. 11, 2014, now abandoned, which is a continuation-in-part of application No. 14/096,875, filed on Dec. 4, 2013, now Pat. No. 9,364,380, which is a continuation-in-part of application No. 14/050,998, filed on Oct. 10, 2013, now Pat. No. 9,265,679, which is a continuation of application No. 13/317,012, filed on Oct. 6, 2011, now Pat. No. 8,719,979, which is a continuation of application No. 12/460,702, filed on Jul. 23, 2009, now Pat. No. 8,060,960, which is a continuation of application No. 11/788,513, filed on Apr. 20, 2007, now Pat. No. 7,565,708, which is a continuation of application No. 11/159,494, filed on Jun. 23, 2005, now Pat. No. 7,343,635, which is a continuation-in-part of application No. 11/062,775, filed on Feb. 22, 2005, now Pat. No. 7,152,261.

(60) Provisional application No. 60/798,288, filed on May 5, 2006.

(51) Int. Cl.
| | | |
|---|---|---|
| *A61G 7/00* | | (2006.01) |
| *A61G 7/008* | | (2006.01) |
| *A61G 13/00* | | (2006.01) |
| *A61G 13/04* | | (2006.01) |
| *A61G 13/06* | | (2006.01) |
| *A61G 13/08* | | (2006.01) |
| *A61G 13/10* | | (2006.01) |

(52) U.S. Cl.
CPC ..... *A61G 13/0036* (2013.01); *A61G 13/0054* (2016.11); *A61G 13/02* (2013.01); *A61G 13/04* (2013.01); *A61G 13/06* (2013.01); *A61G 13/08* (2013.01); *A61G 13/104* (2013.01); *A61G 2200/325* (2013.01)

(56) References Cited

U.S. PATENT DOCUMENTS

| | | | |
|---|---|---|---|
| 430,635 A | 6/1890 | Fox | |
| 769,415 A | 9/1904 | Smock | |
| 987,423 A | 3/1911 | Barnett | |
| 1,032,743 A | 7/1912 | Courtney | |
| 1,046,430 A | 12/1912 | Beitz | |
| 1,098,209 A | 5/1914 | Allen | |
| 1,098,477 A | 6/1914 | Cashman | |
| 1,143,618 A | 6/1915 | Ewald | |
| 1,160,451 A | 11/1915 | Sanford | |
| 1,171,713 A | 2/1916 | Gilkerson | |
| 1,356,467 A | 10/1920 | Payne | |
| 1,404,482 A | 1/1922 | Sawyer | |
| 1,482,439 A | 2/1924 | McCullough | |
| 1,524,399 A | 1/1925 | Krueger | |
| 1,528,835 A | 3/1925 | McCullough | |
| 1,667,982 A | 5/1928 | Pearson | |
| 1,780,399 A | 11/1930 | Munson | |
| 1,799,692 A | 4/1931 | Knott | |
| 1,938,006 A | 12/1933 | Blanchard | |
| 1,990,357 A | 2/1935 | Ward | |
| 2,188,592 A | 1/1940 | Hosken et al. | |
| 2,261,297 A | 11/1941 | Seib | |
| 2,411,768 A | 11/1946 | Welch | |
| 2,475,003 A | 7/1949 | Black | |
| 2,636,793 A | 4/1953 | Meyer | |
| 2,688,410 A | 9/1954 | Nelson | |
| 2,792,945 A | 5/1957 | Brenny | |
| 3,046,071 A | 7/1962 | Shampaine et al. | |
| 3,049,726 A | 8/1962 | Getz | |
| 3,281,141 A | 10/1966 | Smiley et al. | |
| 3,302,218 A | 2/1967 | Stryker | |
| 3,584,321 A * | 6/1971 | Buchanan | A61B 6/0442 5/607 |
| 3,599,964 A | 8/1971 | Magni | |
| 3,640,416 A | 2/1972 | Temple | |
| 3,766,384 A | 10/1973 | Anderson | |
| 3,814,414 A | 6/1974 | Chapa | |
| 3,827,089 A | 8/1974 | Grow | |
| 3,832,742 A | 9/1974 | Stryker | |
| 3,868,103 A | 2/1975 | Pageot et al. | |
| 3,937,054 A | 2/1976 | Hortvet et al. | |
| 3,988,790 A | 11/1976 | Mracek et al. | |
| 4,101,120 A | 7/1978 | Seshima | |
| 4,131,802 A | 12/1978 | Braden et al. | |
| 4,144,880 A | 3/1979 | Daniels | |
| 4,148,472 A | 4/1979 | Rais et al. | |
| 4,175,550 A | 11/1979 | Leininger et al. | |
| 4,186,917 A | 2/1980 | Rais et al. | |
| 4,195,829 A | 4/1980 | Reser | |
| 4,227,269 A | 10/1980 | Johnston | |
| 4,230,100 A | 10/1980 | Moon | |
| 4,244,358 A * | 1/1981 | Pyers | A61G 7/001 5/607 |
| 4,292,962 A | 10/1981 | Krause | |
| 4,391,438 A | 7/1983 | Heffington, Jr. | |
| 4,435,861 A | 3/1984 | Lindley | |
| 4,474,364 A | 10/1984 | Brendgord | |
| 4,503,844 A | 3/1985 | Siczek | |
| 4,552,346 A | 11/1985 | Schnelle et al. | |
| 4,712,781 A | 12/1987 | Watanabe | |
| 4,715,073 A | 12/1987 | Butler | |
| 4,718,077 A | 1/1988 | Moore et al. | |
| 4,763,643 A | 8/1988 | Vrzalik | |
| 4,771,785 A | 9/1988 | Duer | |
| 4,830,337 A | 5/1989 | Ichiro et al. | |
| 4,850,775 A | 7/1989 | Lee et al. | |
| 4,862,529 A | 9/1989 | Peck | |
| 4,872,656 A | 10/1989 | Brendgord et al. | |
| 4,872,657 A | 10/1989 | Lussi | |
| 4,887,325 A | 12/1989 | Tesch | |
| 4,937,901 A | 7/1990 | Brennan | |
| 4,939,801 A | 7/1990 | Schaal et al. | |
| 4,944,500 A | 7/1990 | Mueller et al. | |
| 4,953,245 A | 9/1990 | Jung | |
| 4,970,737 A | 11/1990 | Sagel | |
| 4,989,848 A | 2/1991 | Monroe | |
| 5,013,018 A | 5/1991 | Sicek et al. | |
| 5,088,706 A | 2/1992 | Jackson | |
| 5,131,103 A | 7/1992 | Thomas et al. | |
| 5,131,105 A | 7/1992 | Harrawood et al. | |
| 5,131,106 A * | 7/1992 | Jackson | A61G 13/00 5/607 |
| 5,161,267 A | 11/1992 | Smith | |
| 5,163,890 A | 11/1992 | Perry, Jr. | |
| 5,181,289 A | 1/1993 | Kassai | |
| 5,208,928 A | 5/1993 | Kuck et al. | |
| 5,210,887 A | 5/1993 | Kershaw | |
| 5,210,888 A | 5/1993 | Canfield | |
| 5,230,112 A | 7/1993 | Harrawood et al. | |
| 5,231,741 A | 8/1993 | Maguire | |
| 5,239,716 A | 8/1993 | Fisk | |
| 5,274,862 A | 1/1994 | Palmer, Jr. | |
| 5,294,179 A | 3/1994 | Rudes et al. | |
| 5,333,334 A | 8/1994 | Kassai | |
| 5,393,018 A | 2/1995 | Roth et al. | |
| 5,444,882 A | 8/1995 | Andrews et al. | |
| 5,461,740 A | 10/1995 | Pearson | |
| 5,468,216 A | 11/1995 | Johnson et al. | |
| 5,487,195 A | 1/1996 | Ray | |
| 5,499,408 A | 3/1996 | Nix | |
| 5,524,304 A | 6/1996 | Shutes | |
| 5,544,371 A | 8/1996 | Fuller | |
| 5,579,550 A | 12/1996 | Bathrick et al. | |
| 5,588,705 A | 12/1996 | Chang | |
| 5,613,254 A | 3/1997 | Clayman et al. | |
| 5,640,730 A * | 6/1997 | Godette | A47C 20/041 5/617 |
| 5,645,079 A | 7/1997 | Zahiri et al. | |
| 5,658,315 A * | 8/1997 | Lamb | A61G 13/0036 606/240 |

(56) References Cited

U.S. PATENT DOCUMENTS

| | | | |
|---|---|---|---|
| 5,659,909 A | 8/1997 | Pfeuffer et al. |
| 5,673,443 A | 10/1997 | Marmor |
| 5,737,781 A | 4/1998 | Votel |
| 5,754,997 A | 5/1998 | Lussi et al. |
| 5,774,914 A | 7/1998 | Johnson et al. |
| 5,794,286 A | 8/1998 | Scott et al. |
| 5,829,077 A | 11/1998 | Neige |
| 5,862,549 A | 1/1999 | Morton et al. |
| 5,870,784 A * | 2/1999 | Elliott .................. A47C 20/041 5/616 |
| 5,890,238 A | 4/1999 | Votel |
| 5,901,388 A | 5/1999 | Cowan |
| 5,937,456 A | 8/1999 | Norris |
| 5,940,911 A | 8/1999 | Wang |
| 5,996,151 A | 12/1999 | Bartow et al. |
| 6,000,076 A | 12/1999 | Webster et al. |
| 6,035,465 A | 3/2000 | Rogozinski |
| 6,049,923 A | 4/2000 | Ochiai |
| 6,058,532 A | 5/2000 | Allen |
| 6,109,424 A | 8/2000 | Doan |
| 6,212,713 B1 | 4/2001 | Kuck et al. |
| 6,224,037 B1 | 5/2001 | Novick |
| 6,240,582 B1 | 6/2001 | Reinke |
| 6,260,220 B1 * | 7/2001 | Lamb .................. A61G 13/02 5/607 |
| 6,282,736 B1 | 9/2001 | Hand et al. |
| 6,282,738 B1 | 9/2001 | Heimbrock et al. |
| 6,286,164 B1 | 9/2001 | Lamb et al. |
| 6,287,241 B1 | 9/2001 | Ellis |
| 6,295,666 B1 | 10/2001 | Takaura |
| 6,295,671 B1 * | 10/2001 | Reesby ............. A61G 13/0036 5/621 |
| 6,315,564 B1 | 11/2001 | Levisman |
| 6,322,251 B1 | 11/2001 | Ballhaus et al. |
| 6,438,777 B1 | 8/2002 | Bender |
| 6,496,991 B1 | 12/2002 | Votel |
| 6,499,162 B1 | 12/2002 | Lu |
| 6,505,365 B1 | 1/2003 | Hanson et al. |
| 6,526,610 B1 | 3/2003 | Hand et al. |
| 6,634,043 B2 | 10/2003 | Lamb et al. |
| 6,638,299 B2 | 10/2003 | Cox |
| 6,662,388 B2 | 12/2003 | Friel |
| 6,668,396 B2 | 12/2003 | Wei |
| 6,681,423 B2 | 1/2004 | Zachrisson |
| 6,701,553 B1 | 3/2004 | Hand et al. |
| 6,779,210 B1 | 8/2004 | Kelly |
| 6,791,997 B2 | 9/2004 | Beyer et al. |
| 6,794,286 B2 | 9/2004 | Aoyama et al. |
| 6,817,363 B2 | 11/2004 | Biondo et al. |
| 6,854,137 B2 | 2/2005 | Johnson |
| 6,857,144 B1 | 2/2005 | Huang |
| 6,862,759 B2 | 3/2005 | Hand et al. |
| 6,885,165 B2 | 4/2005 | Henley et al. |
| 6,971,131 B2 | 12/2005 | Bannister |
| 6,971,997 B1 | 12/2005 | Ryan et al. |
| 7,003,828 B2 | 2/2006 | Roussy |
| 7,055,195 B2 | 6/2006 | Roussy |
| 7,089,612 B2 | 8/2006 | Rocher et al. |
| 7,103,931 B2 | 9/2006 | Somasundaram et al. |
| 7,137,160 B2 | 11/2006 | Hand et al. |
| 7,152,261 B2 | 12/2006 | Jackson |
| 7,171,709 B2 | 2/2007 | Weismiller |
| 7,189,214 B1 | 3/2007 | Saunders |
| 7,197,778 B2 | 4/2007 | Sharps |
| 7,213,279 B2 | 5/2007 | Weismiller et al. |
| 7,234,180 B2 | 6/2007 | Horton et al. |
| 7,290,302 B2 | 11/2007 | Sharps |
| 7,331,557 B2 | 2/2008 | Dewert |
| 7,343,635 B2 | 3/2008 | Jackson |
| 7,428,760 B2 | 9/2008 | McCrimmon |
| 7,437,785 B2 | 10/2008 | Farooqui |
| 7,552,490 B2 | 6/2009 | Saracen et al. |
| 7,565,708 B2 | 7/2009 | Jackson |
| 7,596,820 B2 | 10/2009 | Nielsen et al. |
| 7,653,953 B2 | 2/2010 | Lopez-Sansalvador |
| 7,669,262 B2 | 3/2010 | Skripps et al. |
| 7,739,762 B2 | 6/2010 | Lamb et al. |
| 7,874,030 B2 | 1/2011 | Cho et al. |
| 7,874,695 B2 | 1/2011 | Jensen |
| 7,882,583 B2 | 2/2011 | Skripps |
| 8,056,163 B2 | 11/2011 | Lemire et al. |
| 8,060,960 B2 | 11/2011 | Jackson |
| 8,381,331 B2 | 2/2013 | Sharps et al. |
| 8,584,281 B2 | 11/2013 | Diel et al. |
| 8,635,725 B2 | 1/2014 | Tannoury et al. |
| 8,677,529 B2 | 3/2014 | Jackson |
| 8,707,476 B2 | 4/2014 | Sharps |
| 8,707,484 B2 | 4/2014 | Jackson |
| 8,719,979 B2 | 5/2014 | Jackson |
| 8,826,474 B2 | 9/2014 | Jackson |
| 8,826,475 B2 | 9/2014 | Jackson |
| 8,839,471 B2 | 9/2014 | Jackson |
| 8,844,077 B2 | 9/2014 | Jackson et al. |
| 8,856,986 B2 | 10/2014 | Jackson |
| D720,076 S | 12/2014 | Sharps et al. |
| 8,938,826 B2 | 1/2015 | Jackson |
| 8,978,180 B2 | 3/2015 | Jackson |
| 9,180,062 B2 | 11/2015 | Jackson |
| 9,186,291 B2 | 11/2015 | Jackson et al. |
| 9,198,817 B2 | 12/2015 | Jackson |
| 9,205,013 B2 | 12/2015 | Jackson |
| 9,211,223 B2 | 12/2015 | Jackson |
| 9,226,865 B2 | 1/2016 | Jackson et al. |
| 9,265,679 B2 | 2/2016 | Jackson |
| 9,265,680 B2 | 2/2016 | Sharps et al. |
| 9,289,342 B2 | 3/2016 | Jackson |
| 9,295,433 B2 | 3/2016 | Jackson et al. |
| 9,301,897 B2 | 4/2016 | Jackson |
| 9,308,145 B2 | 4/2016 | Jackson |
| 9,339,430 B2 | 5/2016 | Jackson et al. |
| 9,358,170 B2 | 6/2016 | Jackson |
| 9,364,380 B2 | 6/2016 | Jackson |
| 9,402,775 B2 | 8/2016 | Jackson et al. |
| 9,414,982 B2 | 8/2016 | Jackson |
| 9,456,945 B2 | 10/2016 | Jackson |
| 9,468,576 B2 | 10/2016 | Jackson |
| 9,504,622 B2 | 11/2016 | Jackson |
| 9,510,987 B2 | 12/2016 | Jackson et al. |
| 9,549,863 B2 | 1/2017 | Jackson et al. |
| 9,561,145 B2 | 2/2017 | Jackson et al. |
| 9,572,734 B2 | 2/2017 | Jackson et al. |
| 9,610,206 B2 | 4/2017 | Jackson |
| 9,622,928 B2 | 4/2017 | Jackson et al. |
| 2001/0037524 A1 | 11/2001 | Truwit |
| 2002/0170116 A1 | 11/2002 | Borders et al. |
| 2003/0074735 A1 | 4/2003 | Zachrisson |
| 2003/0145383 A1 | 8/2003 | Schwaegerle |
| 2004/0098804 A1 | 5/2004 | Varadharajulu et al. |
| 2004/0133983 A1 * | 7/2004 | Newkirk ............ A61G 13/0036 5/624 |
| 2004/0168253 A1 | 9/2004 | Hand et al. |
| 2004/0219002 A1 | 11/2004 | Lenaers |
| 2006/0248650 A1 | 11/2006 | Skripps |
| 2007/0056105 A1 | 3/2007 | Hyre et al. |
| 2007/0107126 A1 | 5/2007 | Koch et al. |
| 2007/0157385 A1 | 7/2007 | Lemire et al. |
| 2007/0174965 A1 | 8/2007 | Lemire et al. |
| 2007/0266516 A1 | 11/2007 | Cakmak |
| 2008/0216241 A1 | 9/2008 | Mangiardi |
| 2009/0126116 A1 | 5/2009 | Lamb et al. |
| 2009/0235456 A1 | 9/2009 | Bock |
| 2010/0037397 A1 | 2/2010 | Wood |
| 2010/0107790 A1 | 5/2010 | Yamaguchi |
| 2010/0192300 A1 | 8/2010 | Tannoury et al. |
| 2010/0223728 A1 | 9/2010 | Hutchison et al. |
| 2011/0107517 A1 | 5/2011 | Lamb et al. |
| 2011/0197361 A1 | 8/2011 | Hornbach et al. |
| 2012/0005832 A1 | 1/2012 | Turner et al. |
| 2012/0144589 A1 | 6/2012 | Skripps et al. |
| 2012/0174319 A1 | 7/2012 | Menkedick |
| 2012/0246829 A1 | 10/2012 | Lamb et al. |
| 2012/0246830 A1 | 10/2012 | Hornbach |
| 2013/0111666 A1 | 5/2013 | Jackson |
| 2013/0133137 A1 | 5/2013 | Jackson et al. |

(56) References Cited

U.S. PATENT DOCUMENTS

| | | |
|---|---|---|
| 2013/0269710 A1 | 10/2013 | Hight et al. |
| 2013/0282234 A1 | 10/2013 | Roberts et al. |
| 2013/0312188 A1 | 11/2013 | Jackson |
| 2014/0068861 A1 | 3/2014 | Jackson et al. |
| 2014/0201914 A1 | 7/2014 | Jackson |
| 2014/0208512 A1 | 7/2014 | Jackson |
| 2014/0317847 A1 | 10/2014 | Jackson |
| 2015/0007391 A1 | 1/2015 | Xu |
| 2015/0059094 A1 | 3/2015 | Jackson |
| 2015/0113733 A1 | 4/2015 | Diel et al. |
| 2015/0150743 A1 | 6/2015 | Jackson |
| 2016/0000620 A1 | 1/2016 | Koch |
| 2016/0000621 A1 | 1/2016 | Jackson et al. |
| 2016/0000626 A1 | 1/2016 | Jackson et al. |
| 2016/0000627 A1 | 1/2016 | Jackson et al. |
| 2016/0000629 A1 | 1/2016 | Jackson et al. |
| 2016/0008201 A1 | 1/2016 | Jackson |
| 2016/0038364 A1 | 2/2016 | Jackson |
| 2016/0136027 A1 | 5/2016 | Jackson |
| 2016/0166452 A1 | 6/2016 | Jackson et al. |
| 2016/0213542 A1 | 7/2016 | Jackson |
| 2016/0296395 A1 | 10/2016 | Jackson et al. |
| 2016/0317372 A1 | 11/2016 | Jackson |
| 2016/0317373 A1 | 11/2016 | Jackson et al. |
| 2016/0346148 A1 | 12/2016 | Jackson et al. |
| 2016/0346149 A1 | 12/2016 | Jackson et al. |
| 2017/0071809 A1 | 3/2017 | Jackson et al. |

FOREIGN PATENT DOCUMENTS

| | | |
|---|---|---|
| GB | 569758 | 6/1945 |
| GB | 810956 | 3/1959 |
| JP | S53763 | 1/1978 |
| JP | 2000-060995 | 2/2000 |
| JP | 2000-116733 | 4/2000 |
| WO | WO99/07320 | 2/1999 |
| WO | WO 00/07537 | 2/2000 |
| WO | WO2000/062731 | 10/2000 |
| WO | WO2001/060308 | 8/2001 |
| WO | WO 02/078589 A1 | 10/2002 |
| WO | WO2003/070145 | 8/2003 |
| WO | WO 2007/130679 A2 | 11/2007 |
| WO | WO2009/054969 | 4/2009 |
| WO | WO2009/100692 | 8/2009 |
| WO | WO2010/051303 A1 | 5/2010 |

OTHER PUBLICATIONS

U.S. Appl. No. 15/431,439, filed Feb. 13, 2017, Jackson.
U.S. Appl. No. 15/465,289, filed Mar. 21, 2017, Jackson et al.
U.S. Appl. No. 15/483,063, filed Apr. 10, 2017, Jackson et al.
Brochure of Smith & Nephew on Spinal Positioning System, 2003, 2004.
Complaint for Patent Infringement, *Jackson v. Mizuho Orthopedic Sys., Inc.*, No. 4:12-CV-01031 (W.D. Mo. Aug. 7, 2012).
First Amended Complaint For Patent Infringement And Correction Of Inventorship, *Jackson v. Mizuho Orthopedic Sys., Inc.*, No. 4:12-CV-01031 (W.D. Mo. Sep. 21, 2012).
Defendant Mizuho Orthopedic Systems, Inc.'s Answer To First Amended Complaint And Counterclaims, *Jackson v. Mizuho Orthopedic Sys., Inc.*, No. 4:12-CV-01031 (W.D. Mo. Nov. 1, 2012).
Plaintiff Roger P. Jackson, MD's, Reply To Counterclaims, *Jackson v. Mizuho Orthopedic Sys., Inc.*, No. 4:12-CV-01031 (W.D. Mo. Nov. 26, 2012).
Roger P. Jackson's Disclosure Of Asserted Claims And Preliminary Infringement Contentions, *Jackson v. Mizuho Orthopedic Sys., Inc.*, No. 4:12-CV-01031 (W.D. Mo. Jan. 4, 2013).
Second Amended Complaint For Patent Infringement, For Correction Of Inventorship, For Breach Of A Non-Disclosure And Confidentiality Agreement, And For Misappropriation Of Dr. Jackson's Right Of Publicity, *Jackson v. Mizuho Orthopedic Sys., Inc.*, No. 4:12-CV-01031 (W.D. Mo. Jan. 28, 2013).
Defendant Mizuho Orthopedic Systems, Inc.'s Answer To Second Amended Complaint And Counterclaims, *Jackson v. Mizuho Orthopedic Sys., Inc.*, No. 4:12-CV-01031 (W.D. Mo. Feb. 19, 2013).
Defendant Mizuho Osi's Invalidity Contentions Pursuant To The Parties' Joint Scheduling Order, *Jackson v. Mizuho Orthopedic Sys., Inc.*, No. 4:12-CV-01031 (W.D. Mo. Feb. 22, 2013).
Plaintiff Roger P. Jackson, MD's, Reply To Second Counterclaims, *Jackson v. Mizuho Orthopedic Sys., Inc.*, No. 4:12-CV-01031 (W.D. Mo. Mar. 12, 2013).
Roger P. Jackson, MD's Disclosure Of Proposed Terms To Be Construed, *Jackson v. Mizuho Orthopedic Sys., Inc.*, No. 4:12-CV-01031 (W.D. Mo. Apr. 5, 2013).
Defendant Mizuho Orthopedic Systems, Inc.'s Disclosure of Proposed Terms and Claim Elements for Construction, *Jackson v. Mizuho Orthopedic Sys., Inc.*, No. 4:12-CV-01031 (W.D. Mo. Apr. 5, 2013).
Mizuho Orthopedic Systems, Inc.'s Disclosure Of Proposed Claim Constructions And Extrinsic Evidence, *Jackson v. Mizuho Orthopedic Sys., Inc.*, No. 4:12-CV-01031 (W.D. Mo. May 13, 2013).
Plaintiff Roger P. Jackson, MD's Disclosure Of Preliminary Proposed Claim Constructions, *Jackson v. Mizuho Orthopedic Sys., Inc.*, No. 4:12-CV-01031 (W.D. Mo. May 13, 2013).
Defendant Mizuho Osi's Amended Invalidity Contentions Pursuant To The Parties' Joint Scheduling Order, *Jackson v. Mizuho Orthopedic Sys., Inc.*, No. 4:12-CV-01031 (W.D. Mo. May 15, 2013).
Joint Claim Construction Chart And Joint Prehearing Statement, *Jackson v. Mizuho Orthopedic Sys., Inc.*, No. 4:12-CV-01031 (W.D. Mo. Jun. 7, 2013).
Defendant Mizuho Orthopedic Systems, Inc.'s Objections And Responses To Plaintiff's First Set Of Interrogatories, *Jackson v. Mizuho Orthopedic Sys., Inc.*, No. 4:12-CV-01031 (W.D. Mo. Jun. 24, 2013).
Defendant Mizuho Orthopedic Systems, Inc.'s Opening Claim Construction Brief, *Jackson v. Mizuho Orthopedic Sys., Inc.*, No. 4:12-CV-01031 (W.D. Mo. Jul. 31, 2013).
Plaintiff Roger P. Jackson, MD's Opening Claim Construction Brief, *Jackson v. Mizuho Orthopedic Sys., Inc.*, No. 4:12-CV-01031 (W.D. Mo. Jul. 31, 2013).
Appendix A Amended Infringement Contentions Claim Chart For Mizuho's Axis System Compared To U.S. Pat. No. 7,565,708, *Jackson v. Mizuho Orthopedic Sys., Inc.*, No. 4:12-CV-01031 (W.D. Mo. Aug. 12, 2013).
Appendix B Amended Infringement Contentions Claim Chart For Mizuho's Axis System Compared To U.S. Pat. No. 8,060,960, *Jackson v. Mizuho Orthopedic Sys., Inc.*, No. 4:12-CV-01031 (W.D. Mo. Aug. 12, 2013).
Appendix C Amended Infringement Contentions Claim Chart For Mizuho's Proaxis System Compared To U.S. Pat. No. 7,565,708, *Jackson v. Mizuho Orthopedic Sys., Inc.*, No. 4:12-CV-01031 (W.D. Mo. Aug. 12, 2013).
Appendix D Amended Infringement Contentions Claim Chart For Mizuho's Proaxis System Compared To U.S. Pat. No. 8,060,960, *Jackson v. Mizuho Orthopedic Sys., Inc.*, No. 4:12-CV-01031 (W.D. Mo. Aug. 12, 2013).
Plaintiff Roger P. Jackson, MD's Responsive Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc's Brief in Response To Plaintiff's Opening Claim Construction Brief, *Jackson v. Mizuho Orthopedic Sys., Inc.*, No. 4:12-CV-01031 (W.D. Mo. Aug. 16, 2013).
Plaintiff Roger P. Jackson, Md's Suggestions in Support Of His Motion To Strike Exhibit A Of Mizuho's Opening Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc.'s Opposition to Plaintiff's Motion to Strike, *Jackson v. Mizuho Orthopedic Sys., Inc.*, No. 4:12-CV-01031 (W.D. Mo. Sep. 3, 2013).
Transcript of Claim Construction Hearing, *Jackson v. Mizuho Orthopedic Sys., Inc.*, No. 4:12-CV-01031 (W.D. Mo. Oct. 11, 2013).

(56) References Cited

OTHER PUBLICATIONS

Plaintiff Roger P. Jackson, MD's Claim Construction Presentation for U.S. District Judge Nanette K. Laughrey, *Jackson v. Mizuho Orthopedic Sys., Inc.*, No. 4:12-CV-01031 (W.D. Mo. Oct. 11, 2013).
Mizuho's Claim Construction Argument, *Jackson v. Mizuho Orthopedic Sys., Inc.*, No. 4:12-CV-01031 (W.D. Mo. Oct. 11, 2013).
Order, *Jackson v. Mizuho Orthopedic Sys., Inc.*, No. 4:12-CV-01031 (W.D. Mo. Apr. 4, 2014).
Brochure of OSI on Modular Table System 90D, pp. 1-15, date of first publication: Unknown.
Pages from website http://www.schaerermayfieldusa.com, pp. 1-5, date of first publication: Unknown.
European Search Report, EP11798501.0, dated Mar. 30, 2015.
Canadian Office Action, CA2803110, dated Mar. 5, 2015.
Chinese Office Action, CN 201180039162.0, dated Jan. 19, 2015.
Japanese Office Action, JP 2014-142074, dated Jun. 18, 2015.
Japanese Office Action, JP 2014-132463, dated Jun. 18, 2015.
Quayle Action, U.S. Appl. No. 14/792,216, dated Sep. 9, 2015.
Australian Patent Examination Report No. 2, AU2014200274, dated Oct. 9, 2015.
European Examination Report, EP11798501.0, dated Nov. 12, 2015.
Japanese Final Rejection (English version), JP 2014-142074, dated Dec. 6, 2015.
International Search Report and Written Opinion of the International Searching Authority, PCT/US2015/039400, dated Dec. 7, 2015, 13 pages.
Japanese Office Action, JP 2016-041088, dated Apr. 12, 2016.

\* cited by examiner

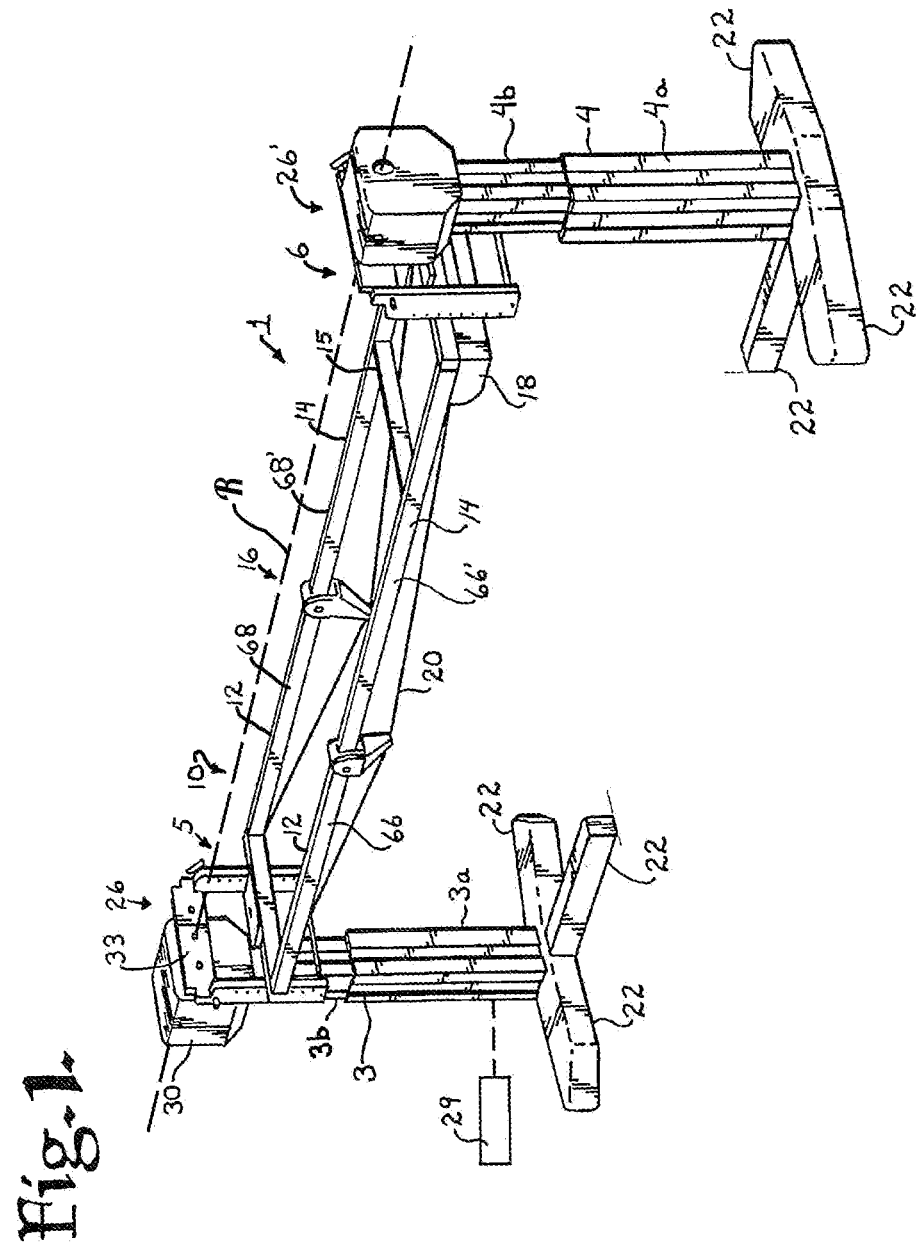

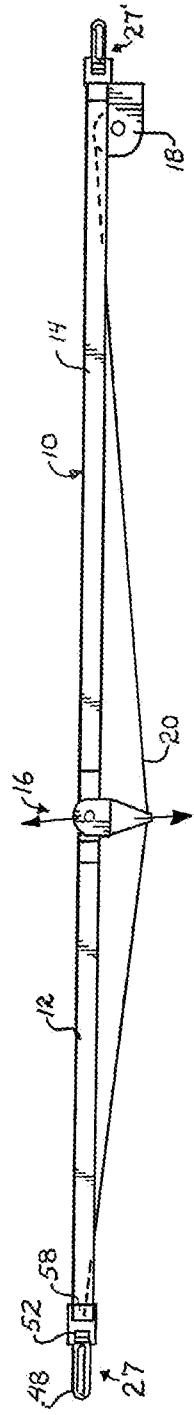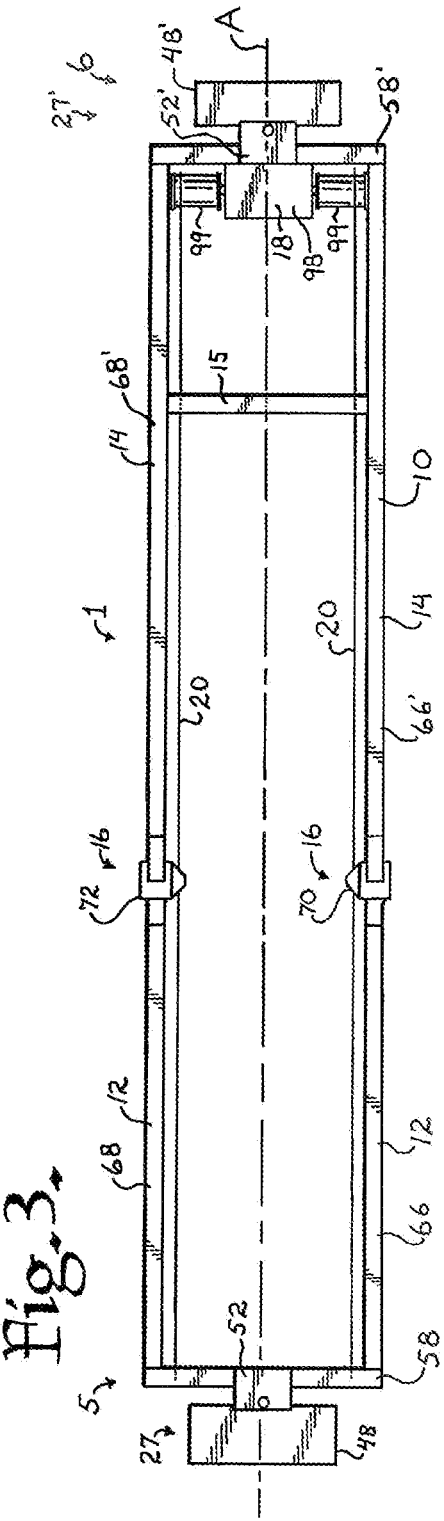

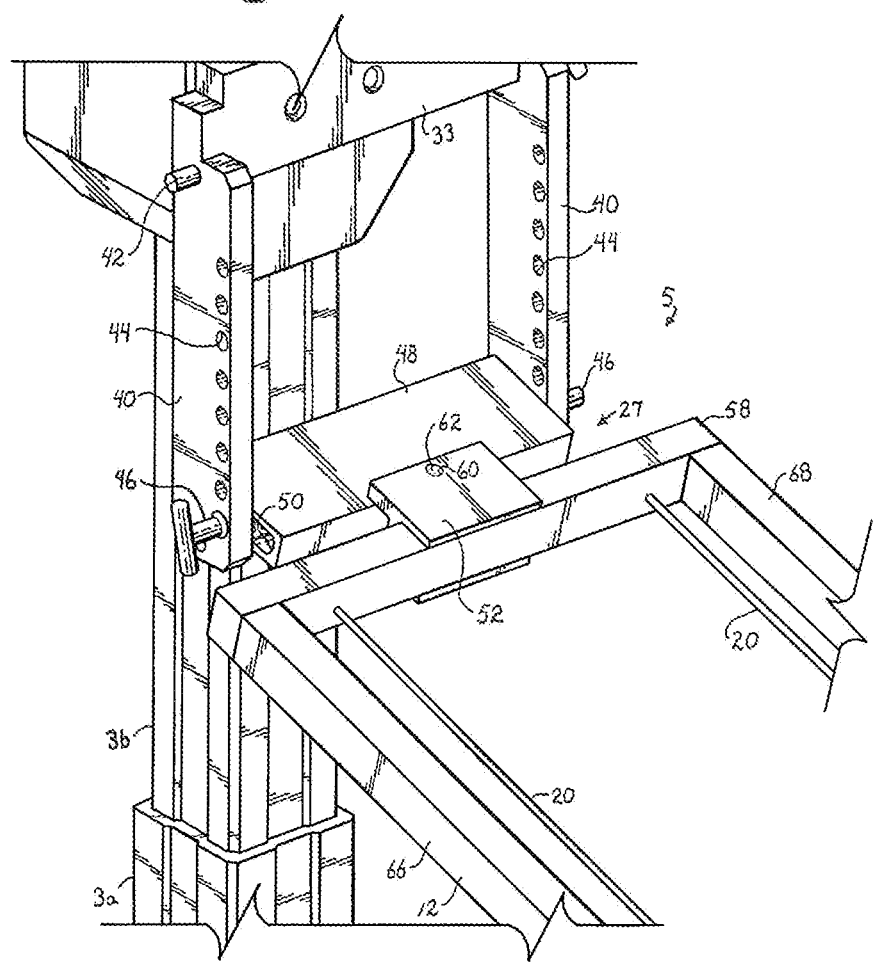

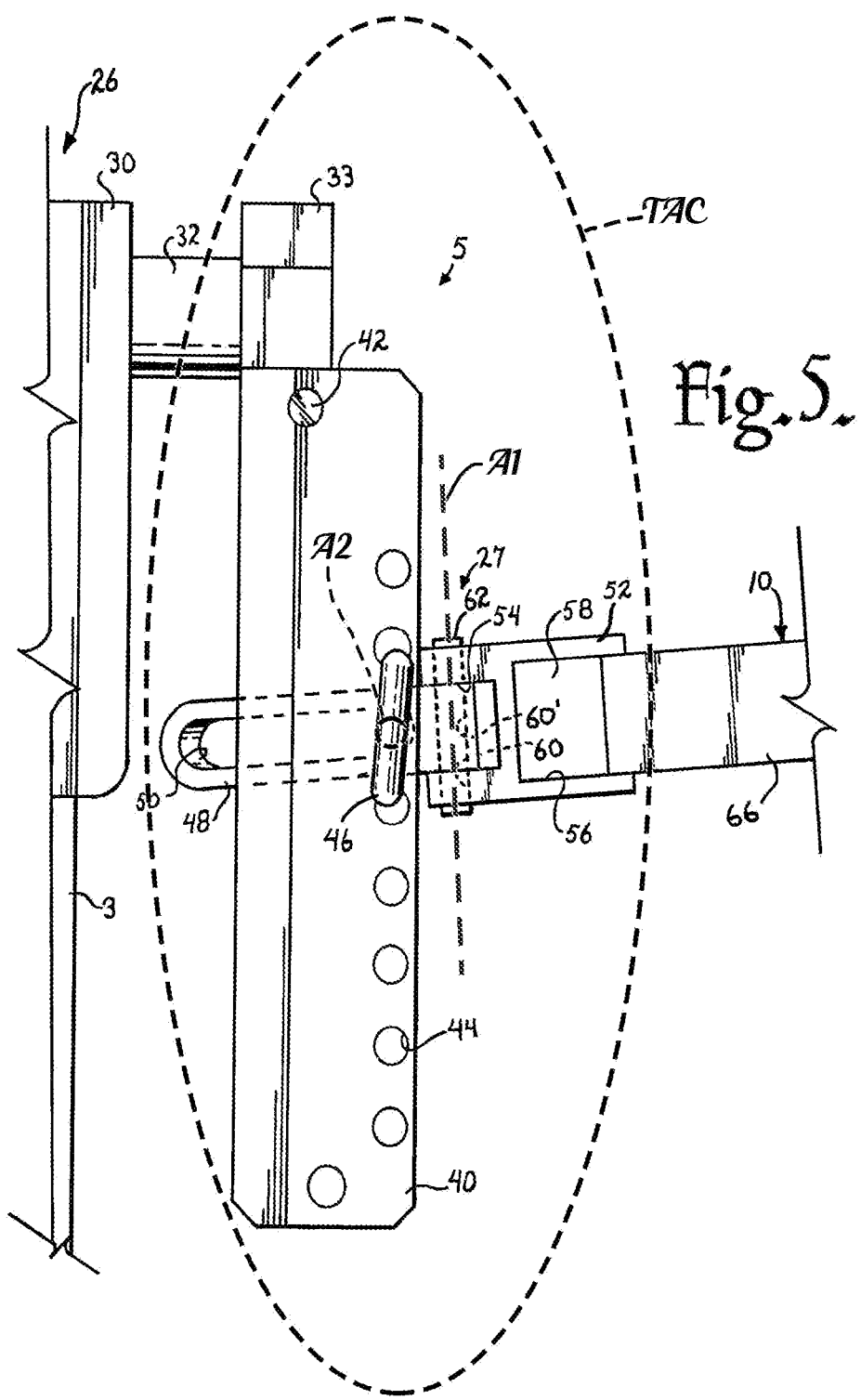

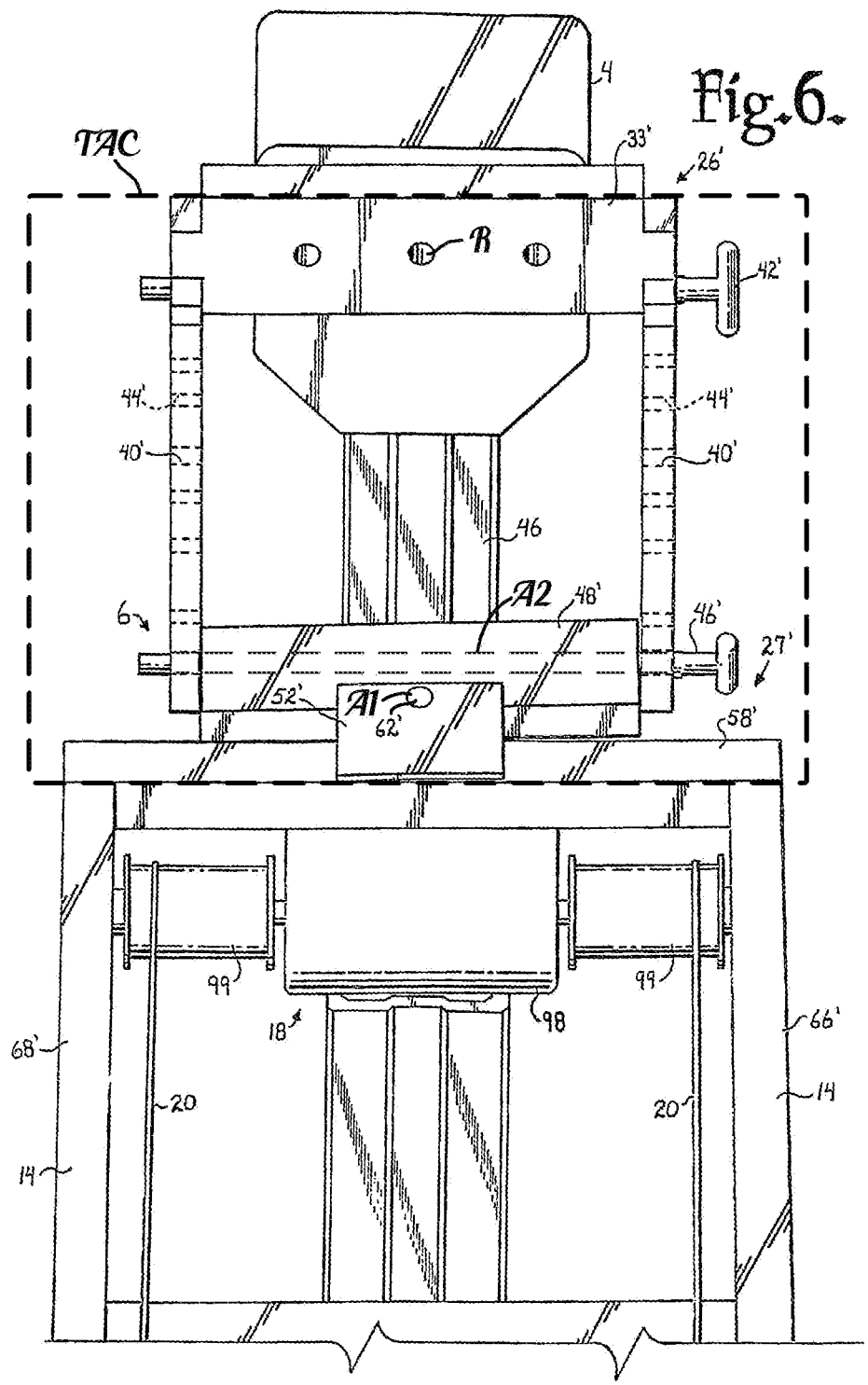

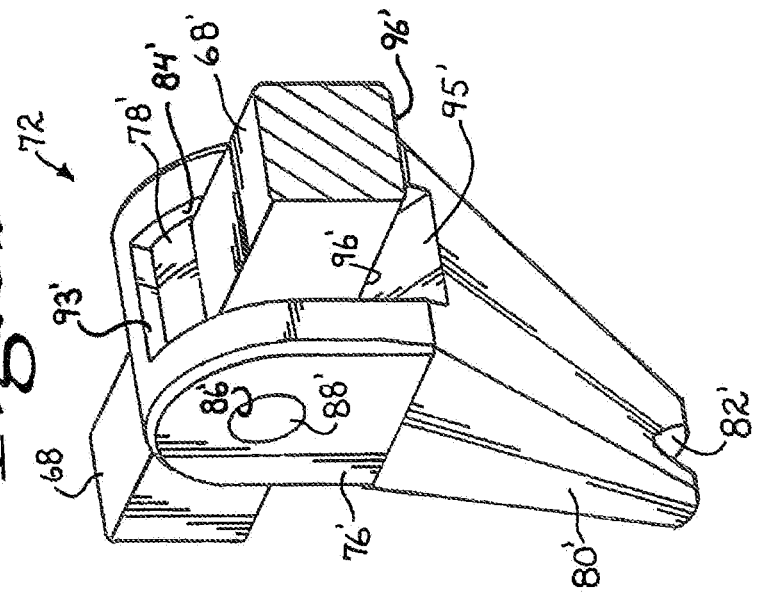
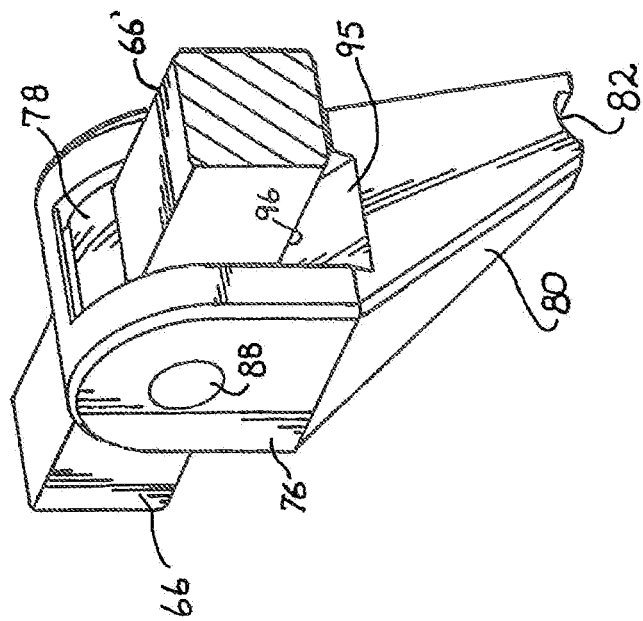

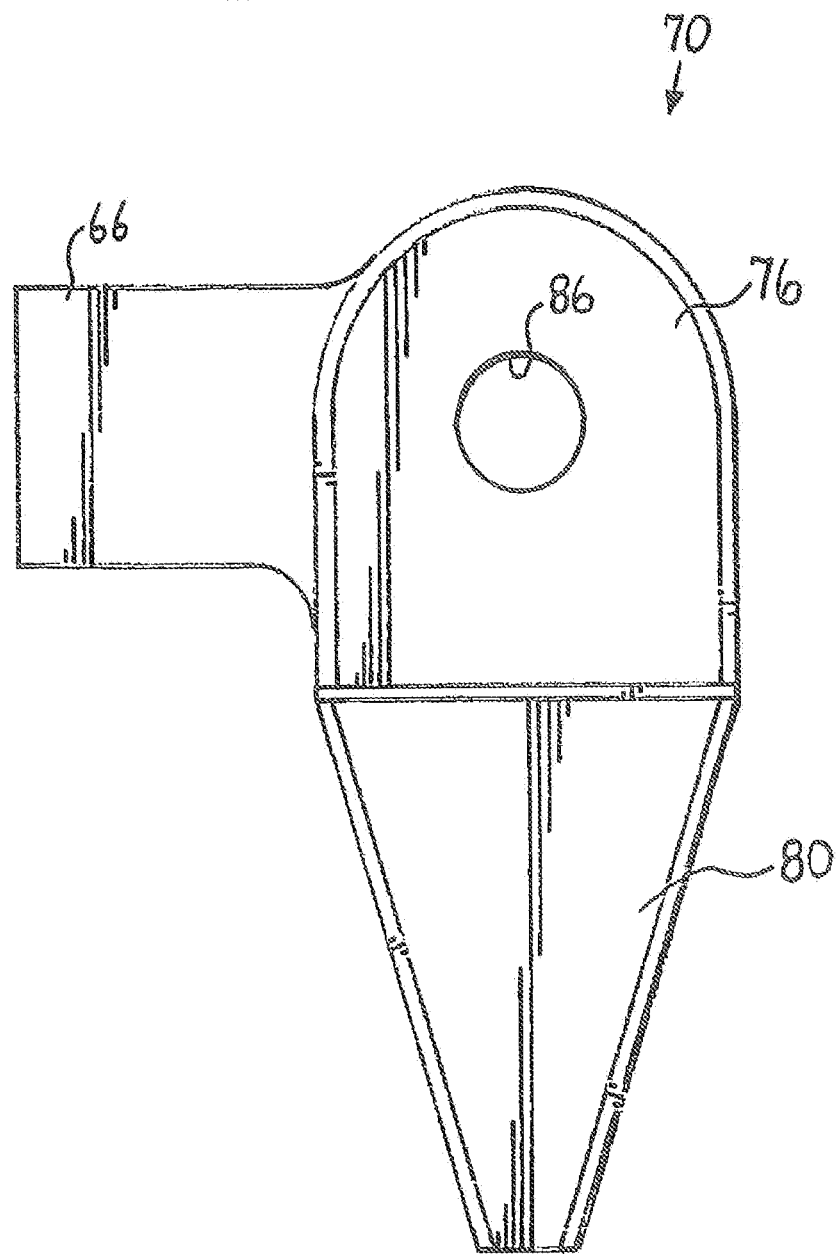

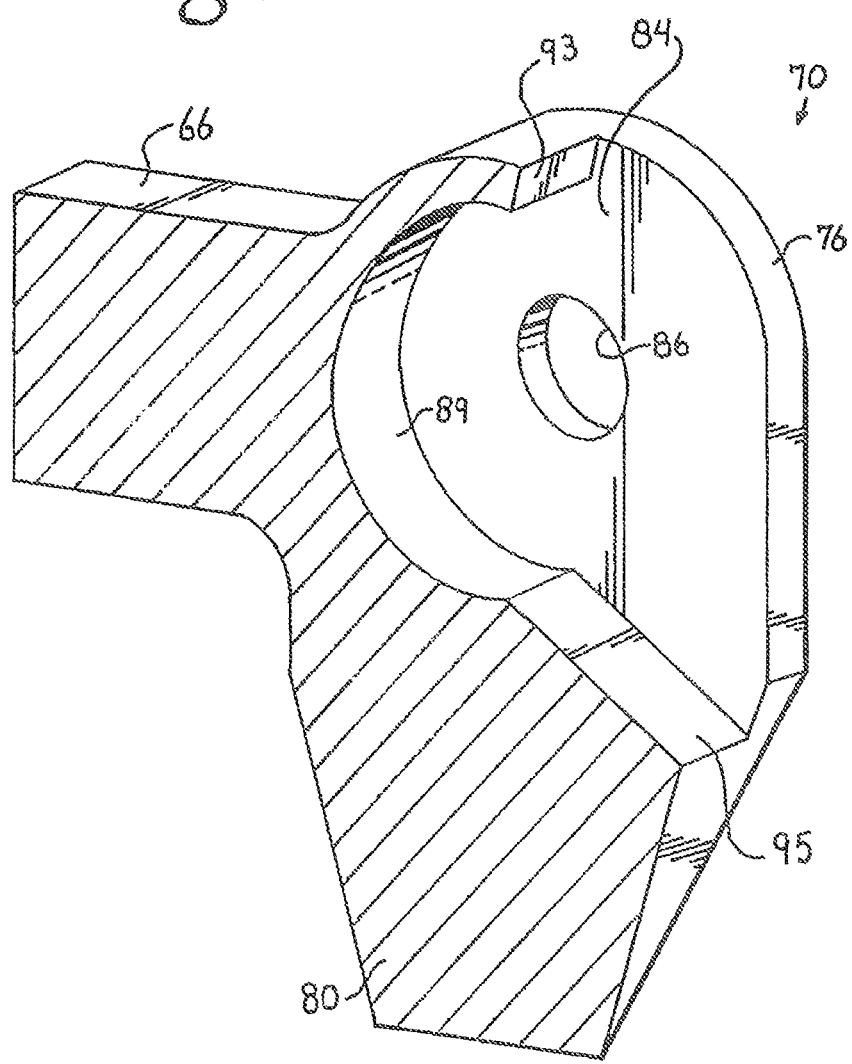

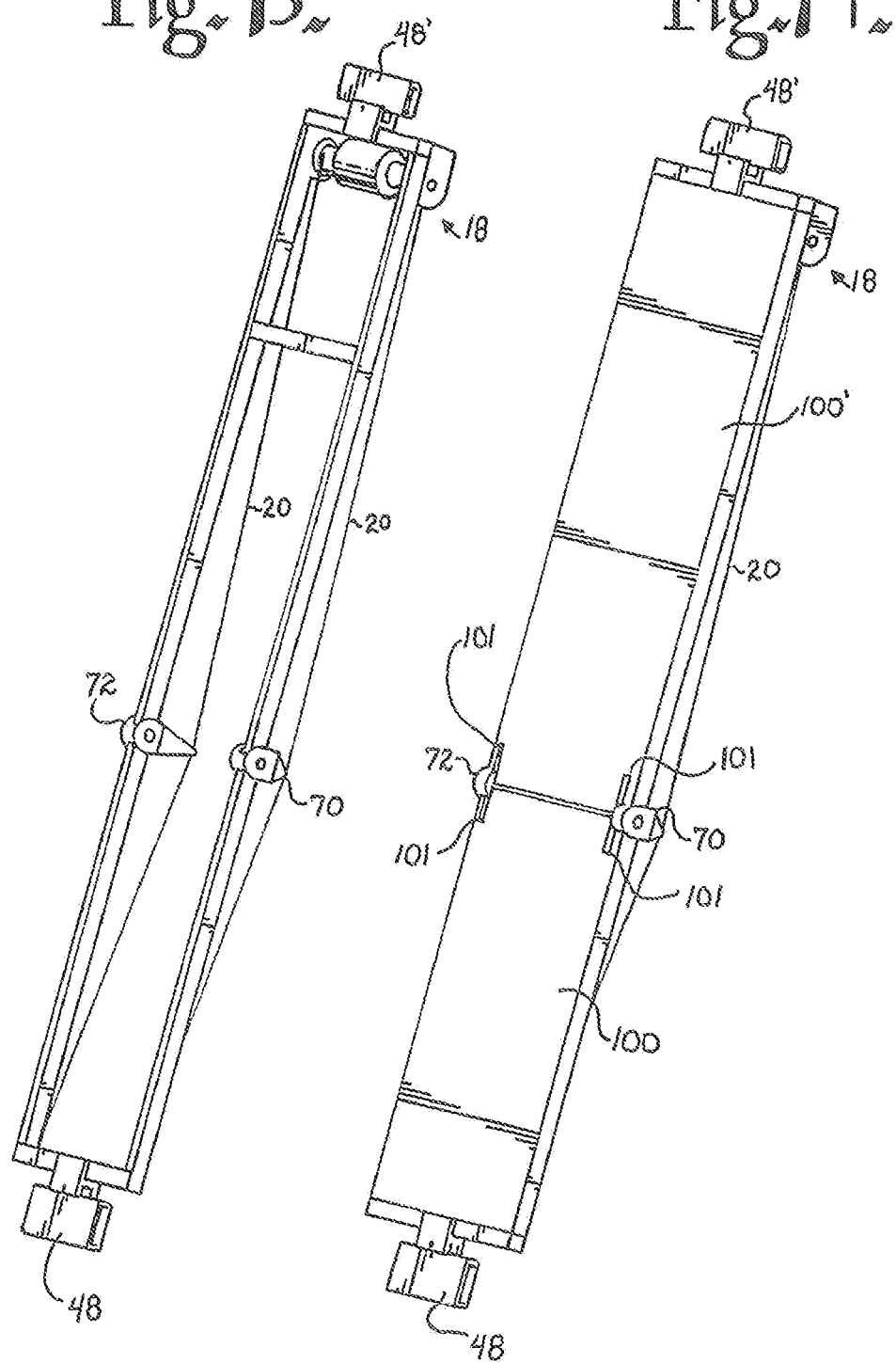

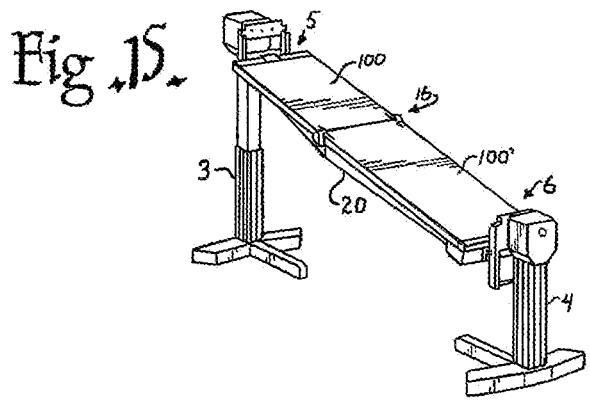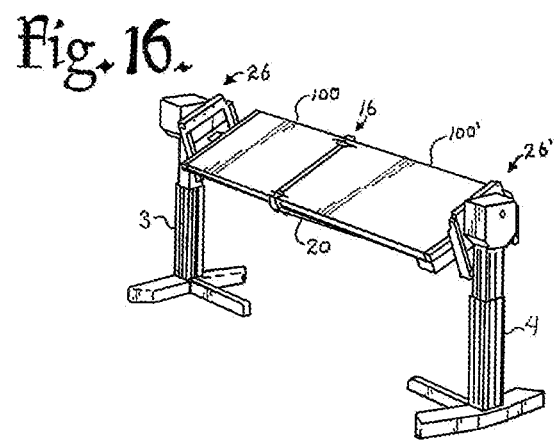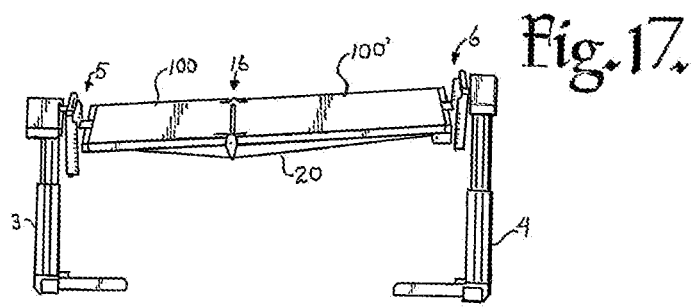

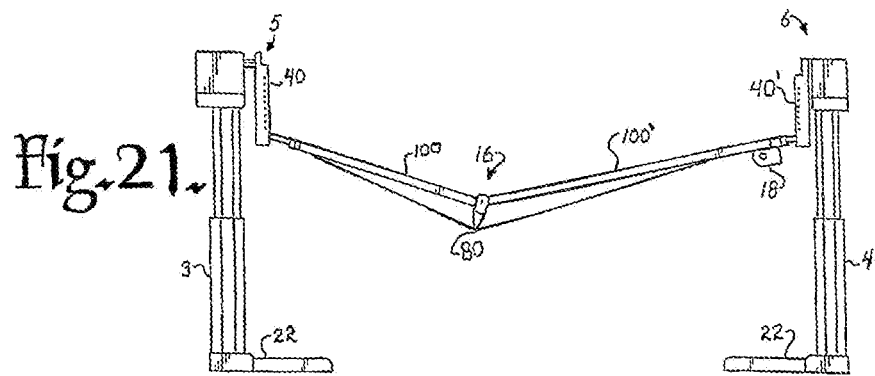
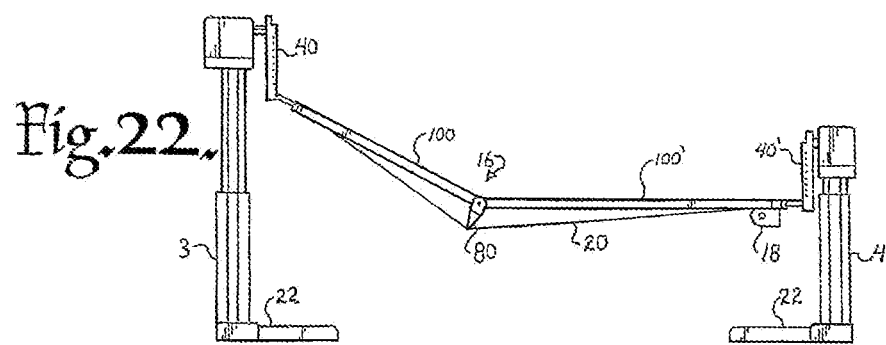
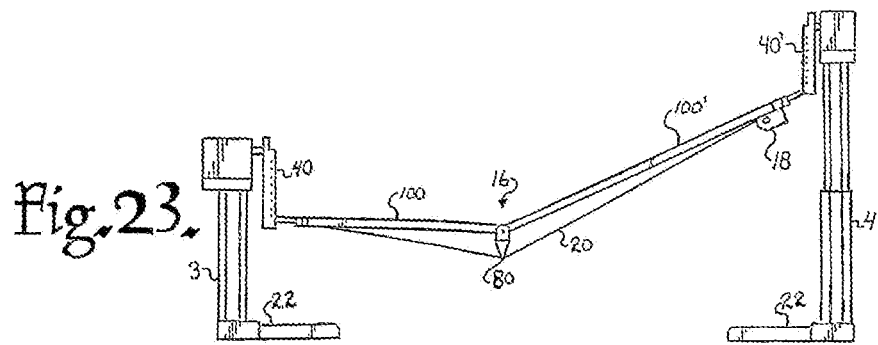

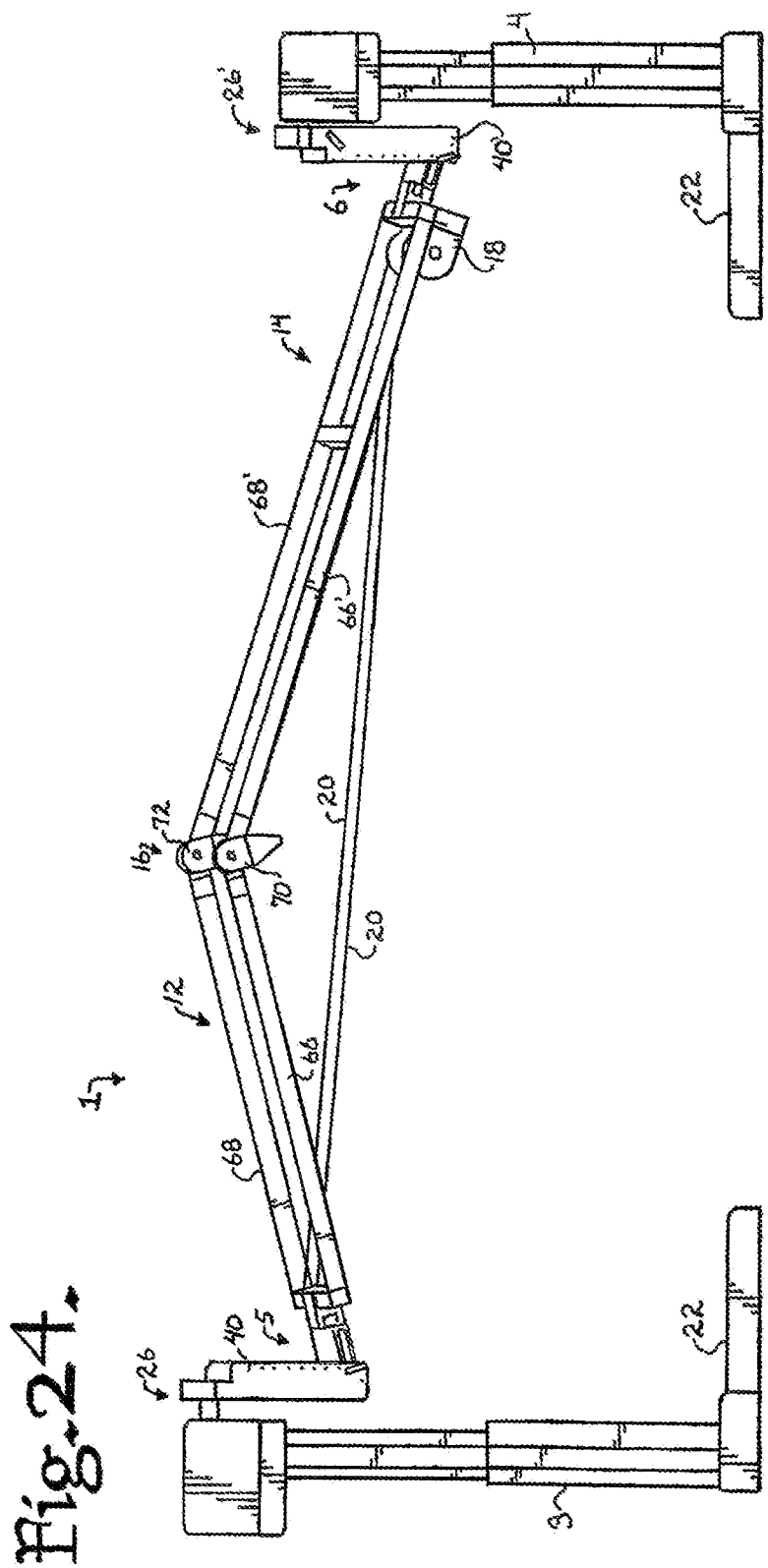

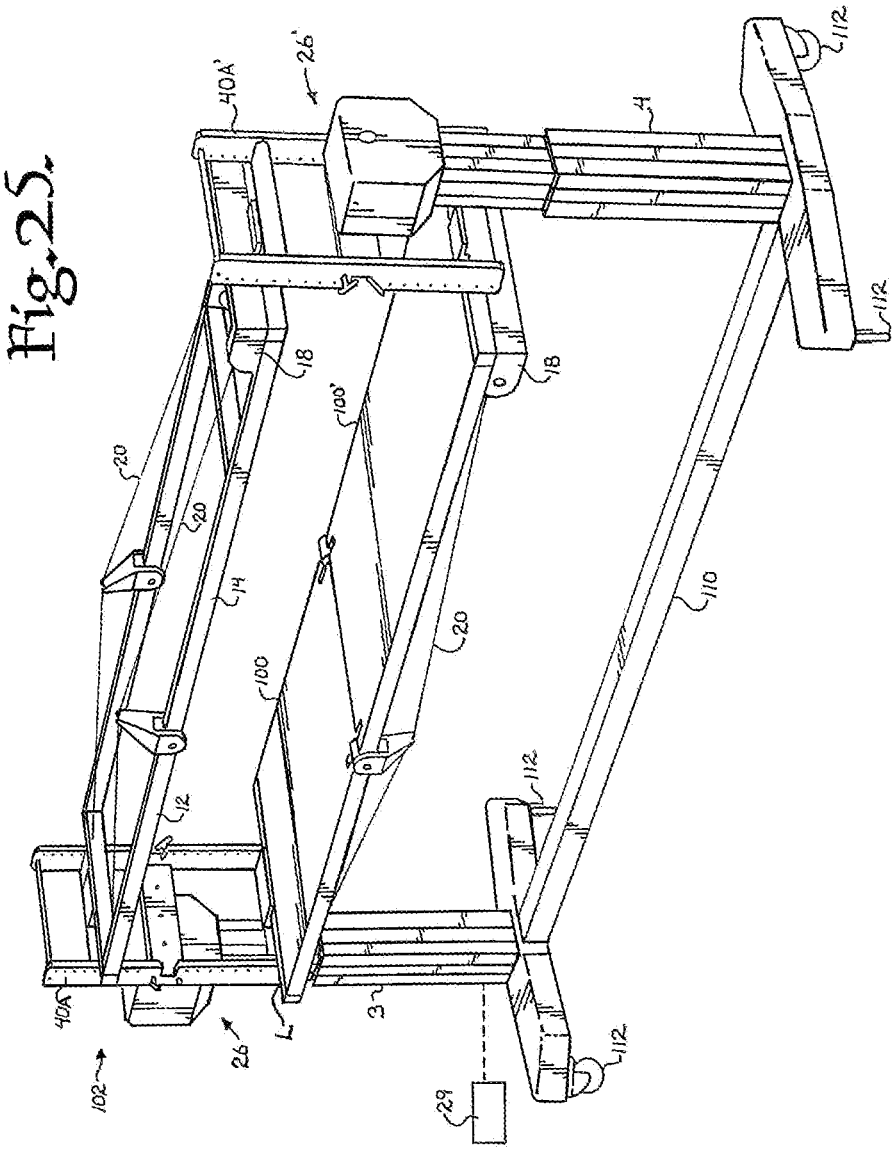

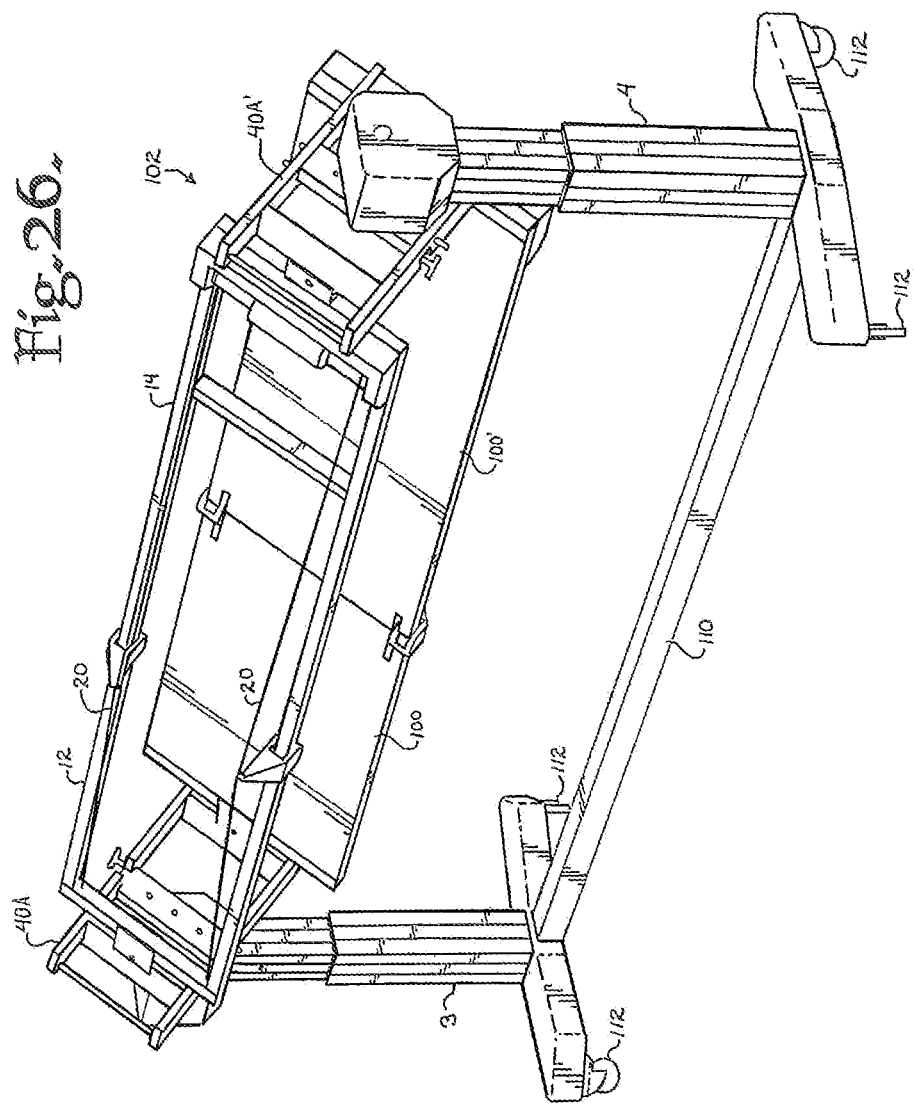

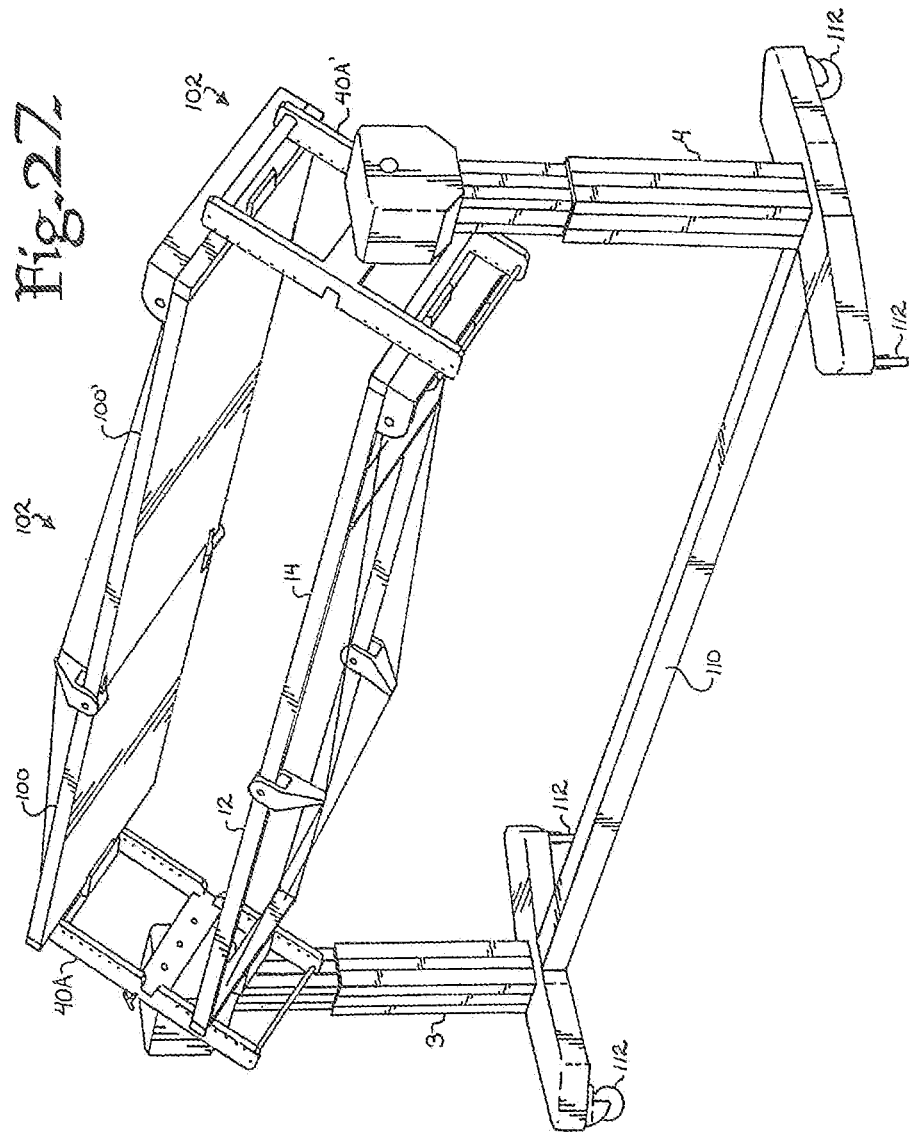

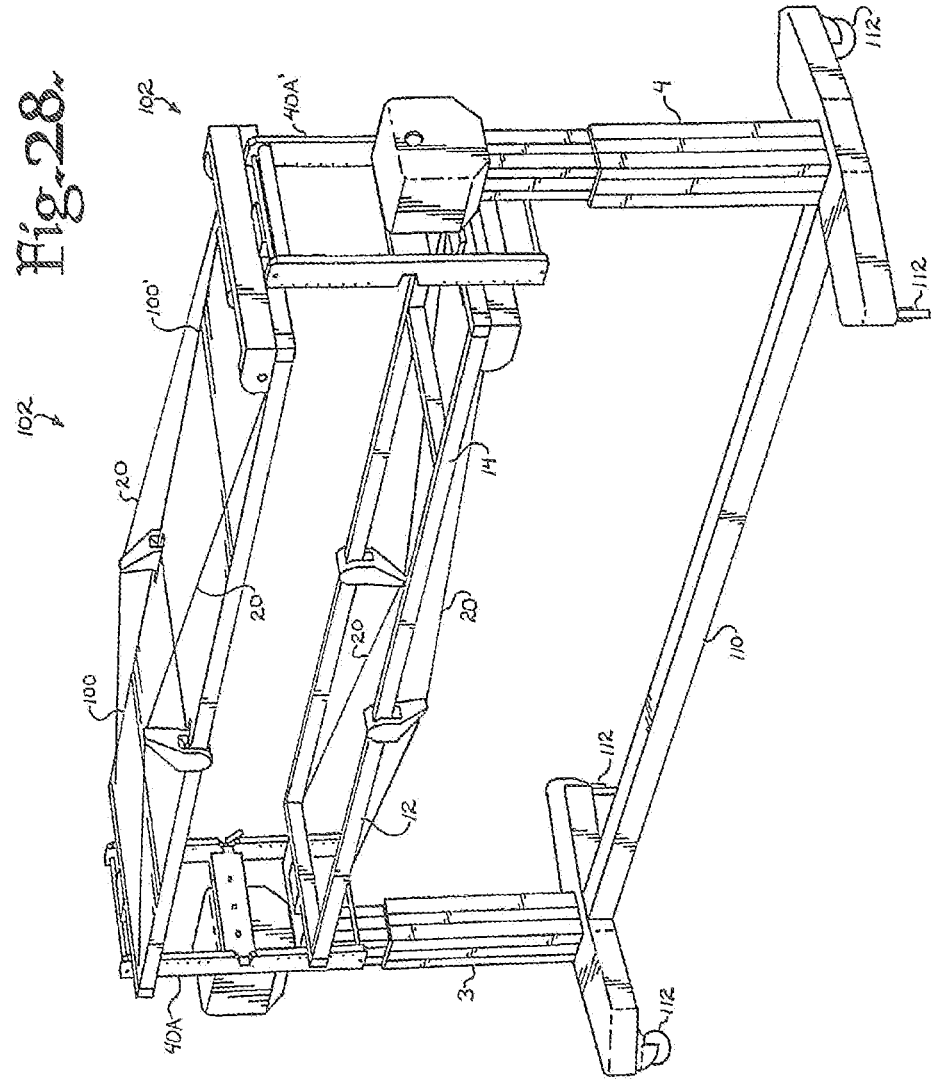

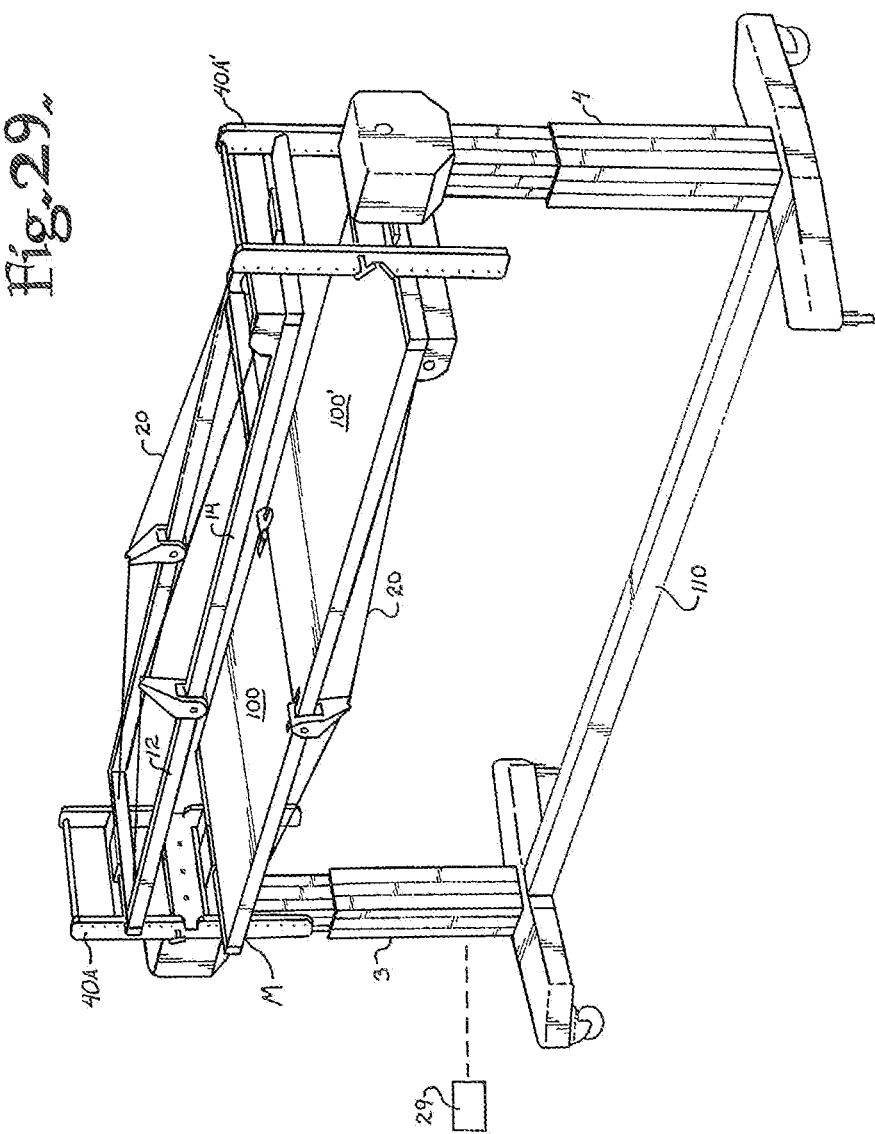

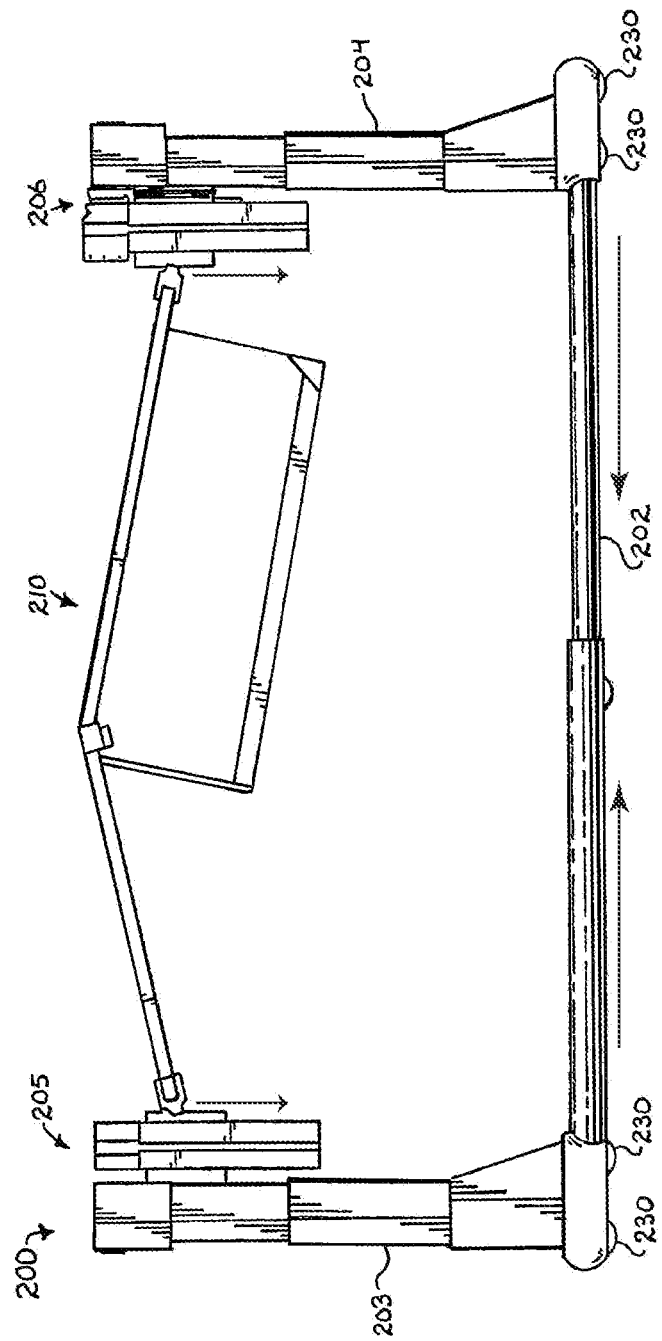

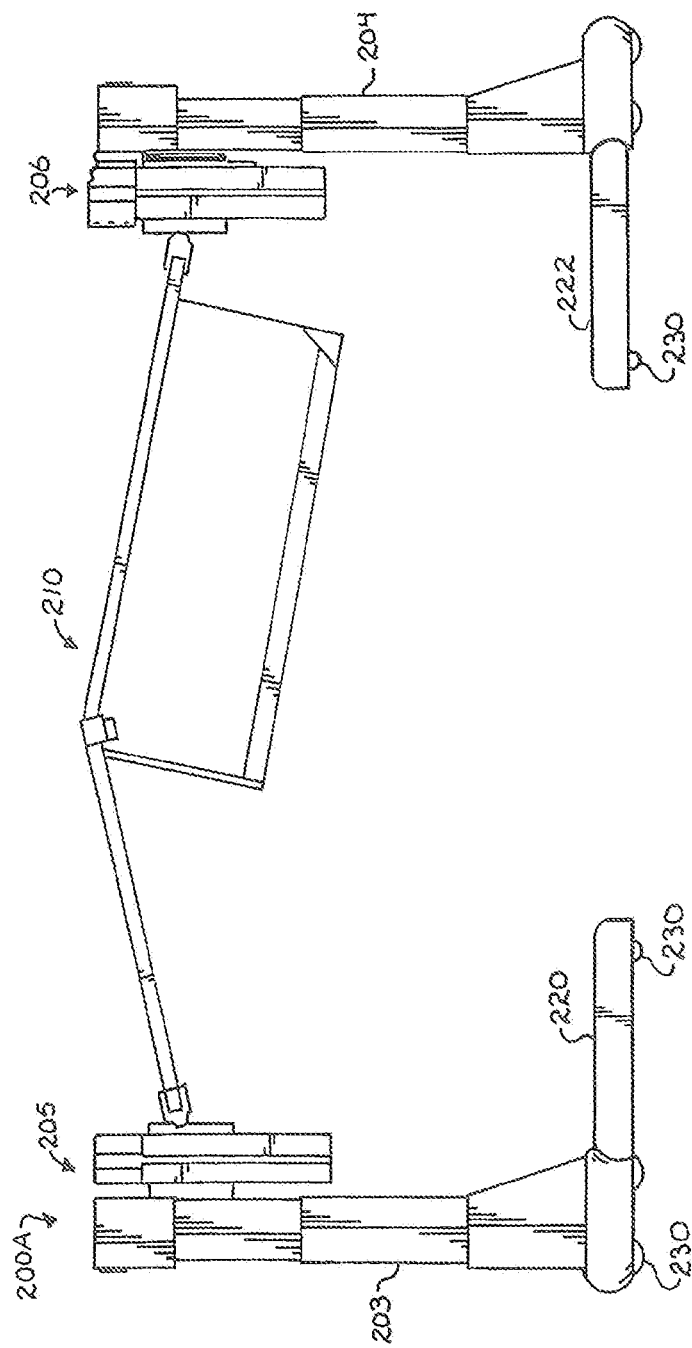

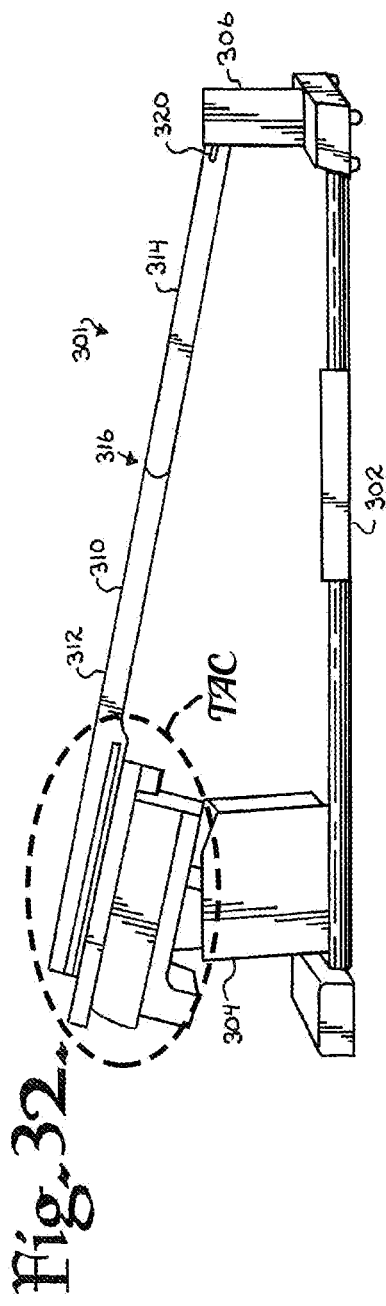
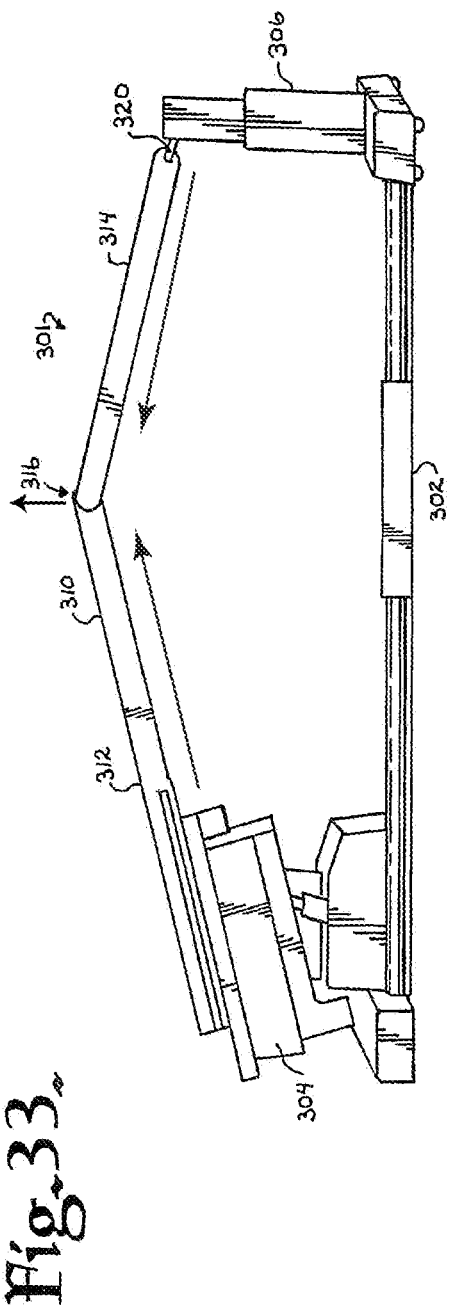

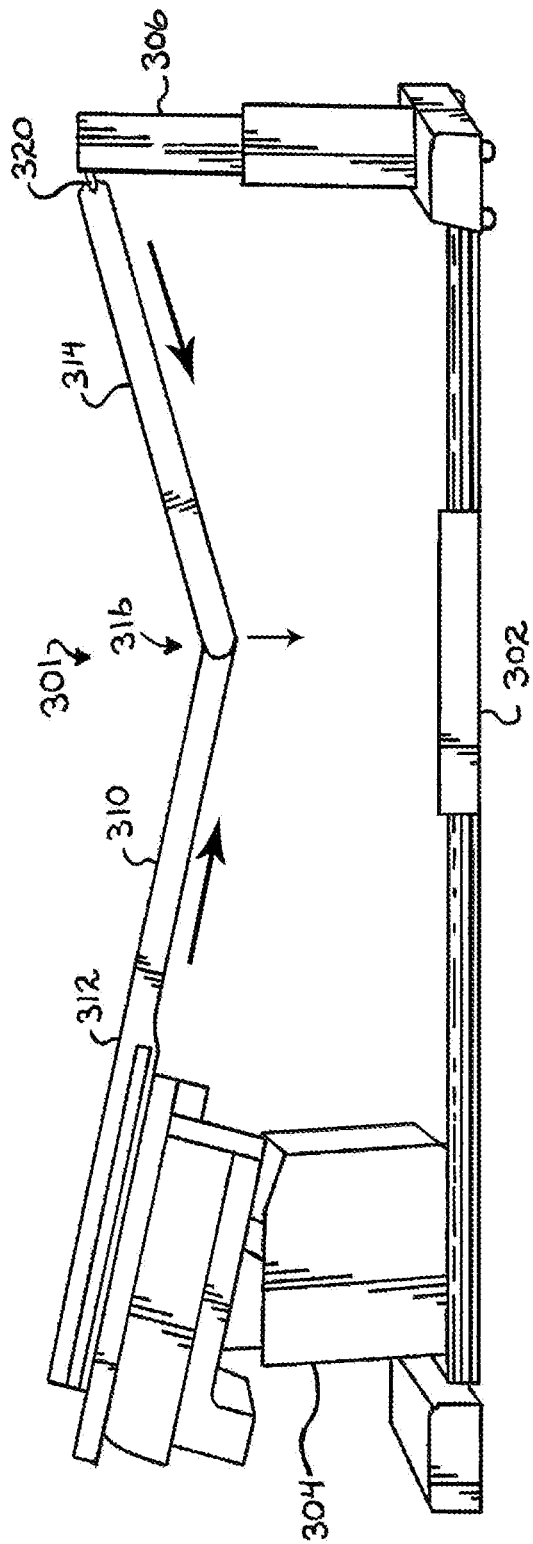

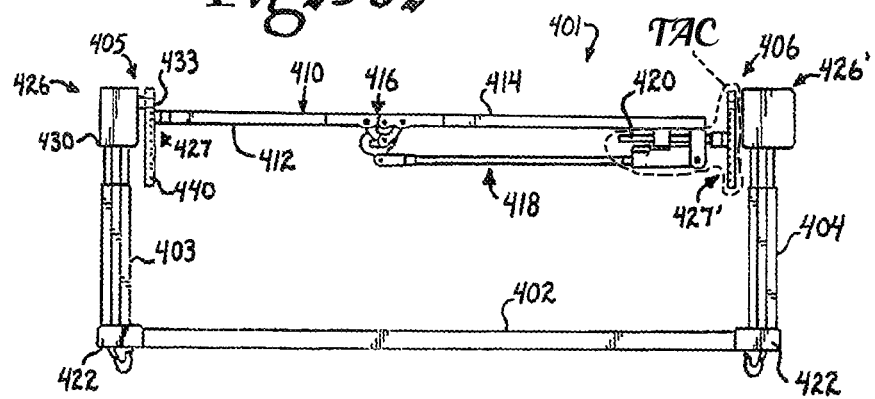
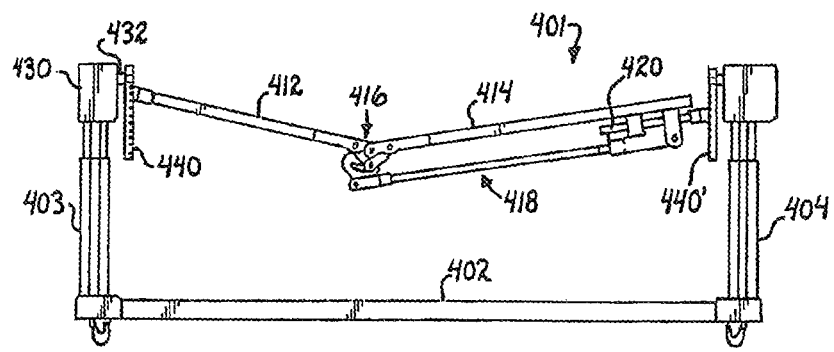
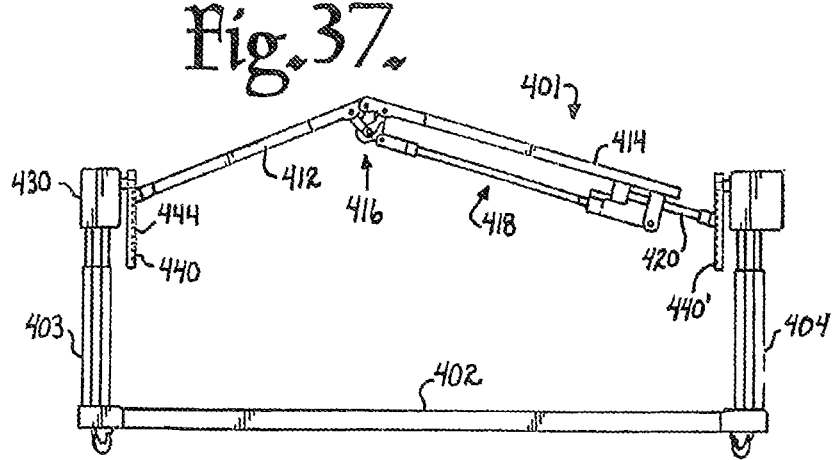

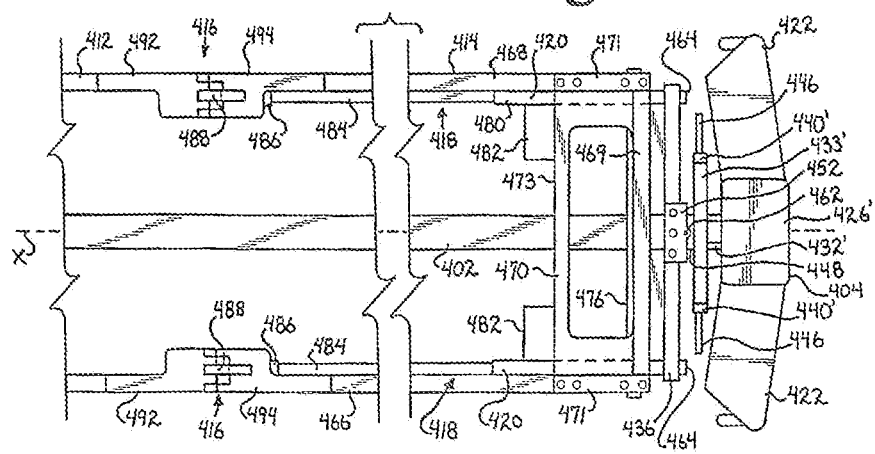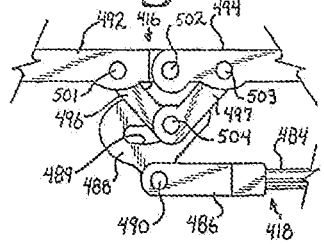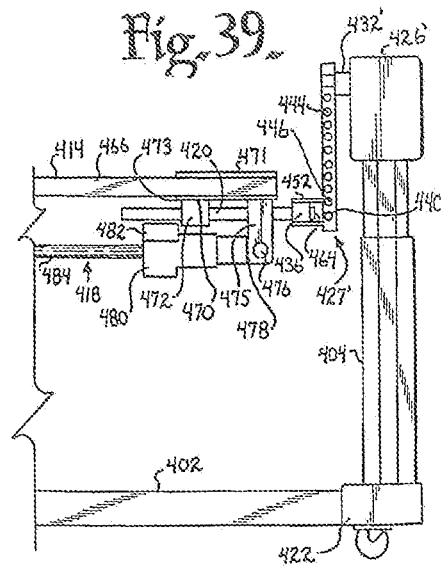

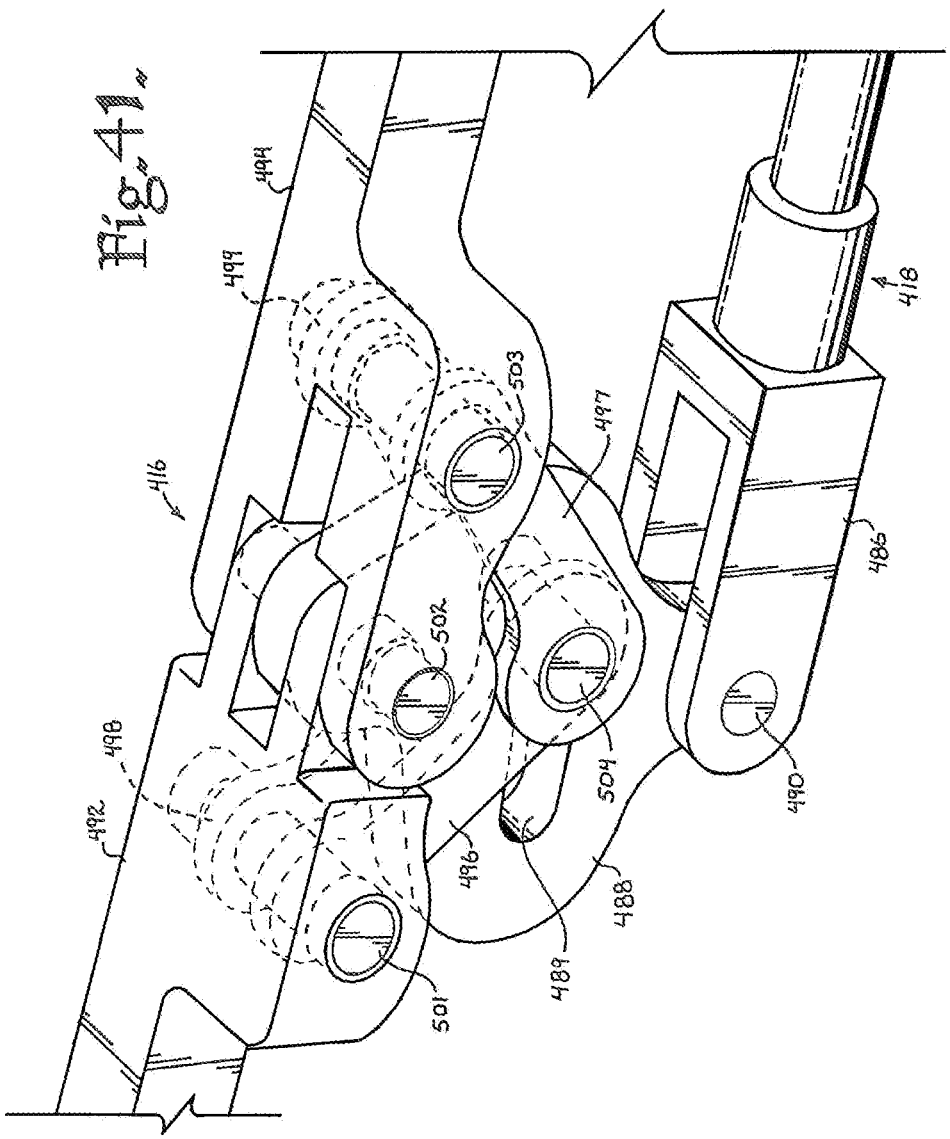

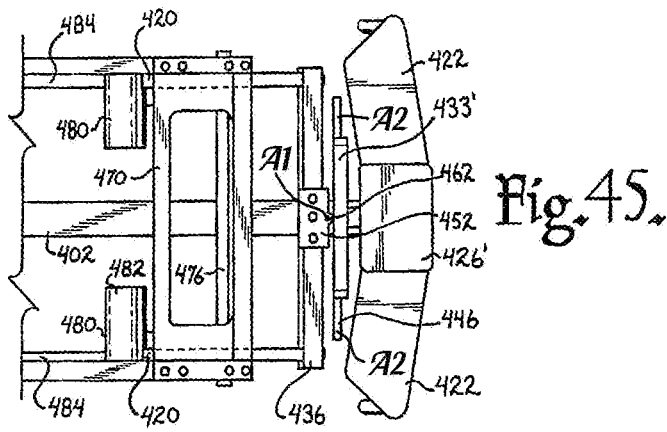
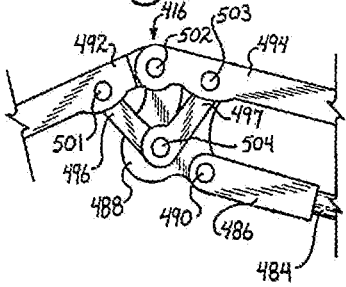
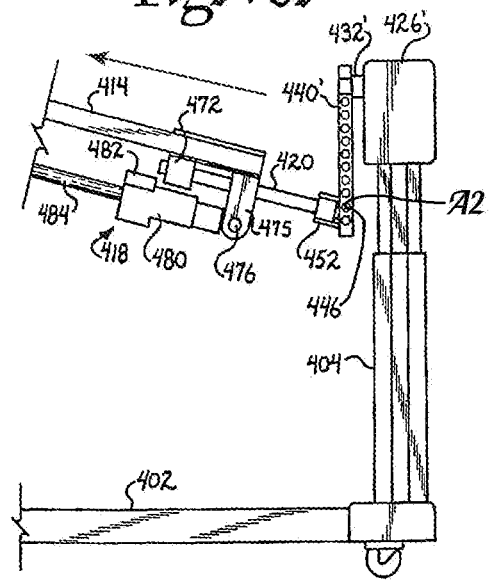

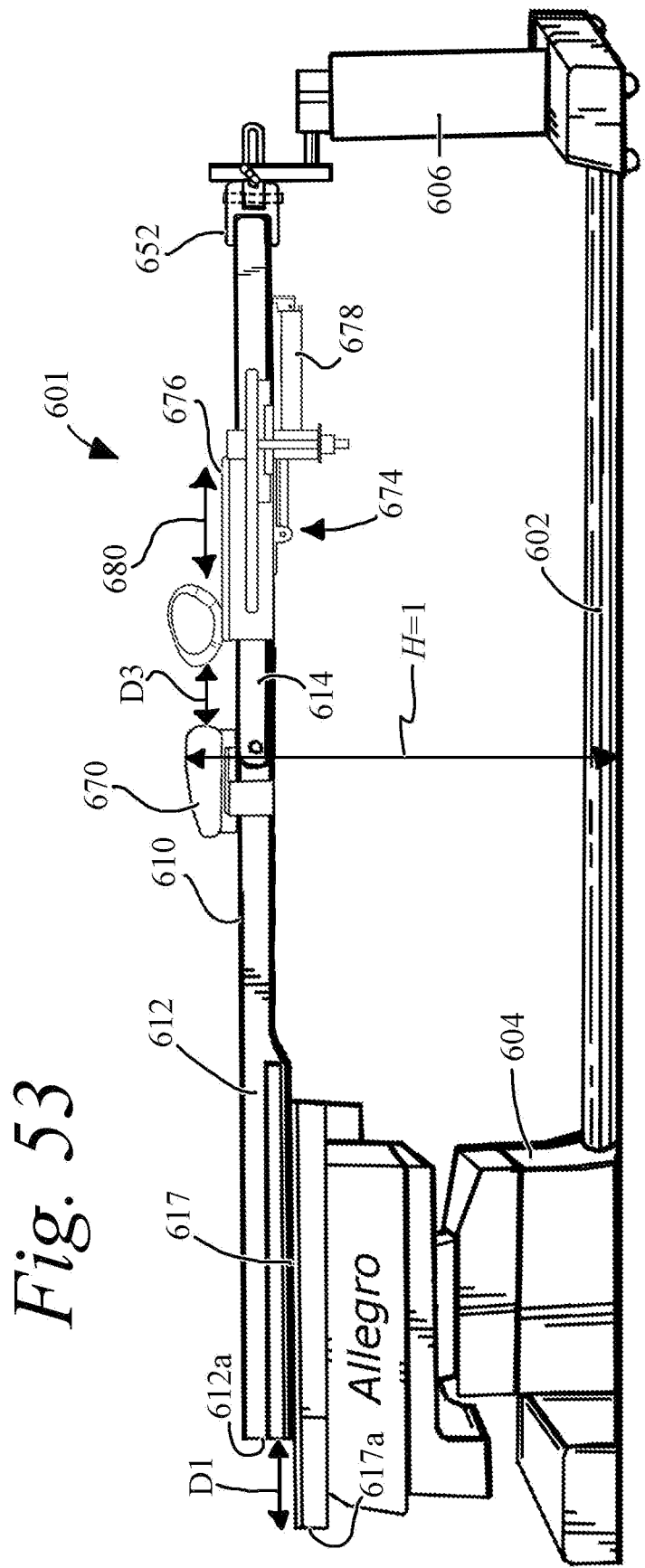

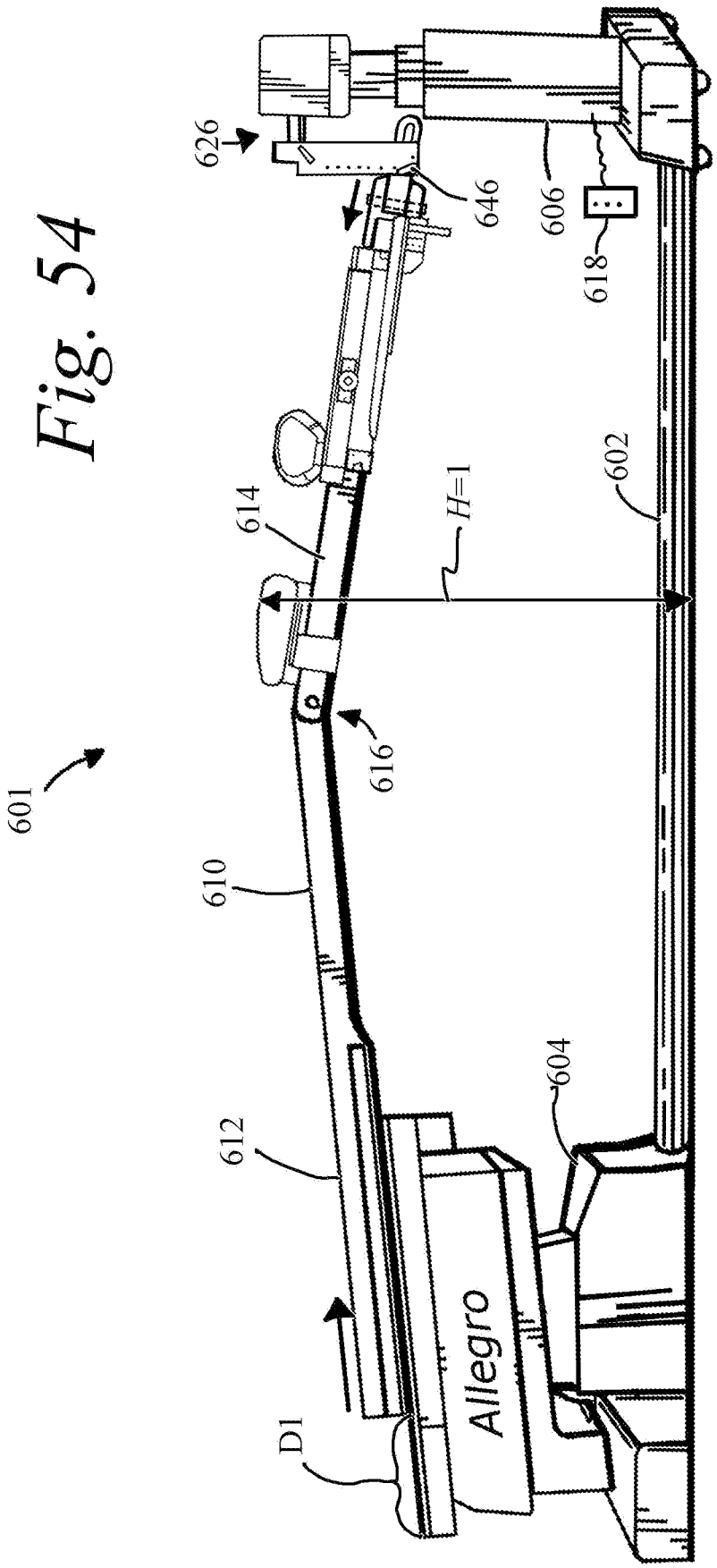

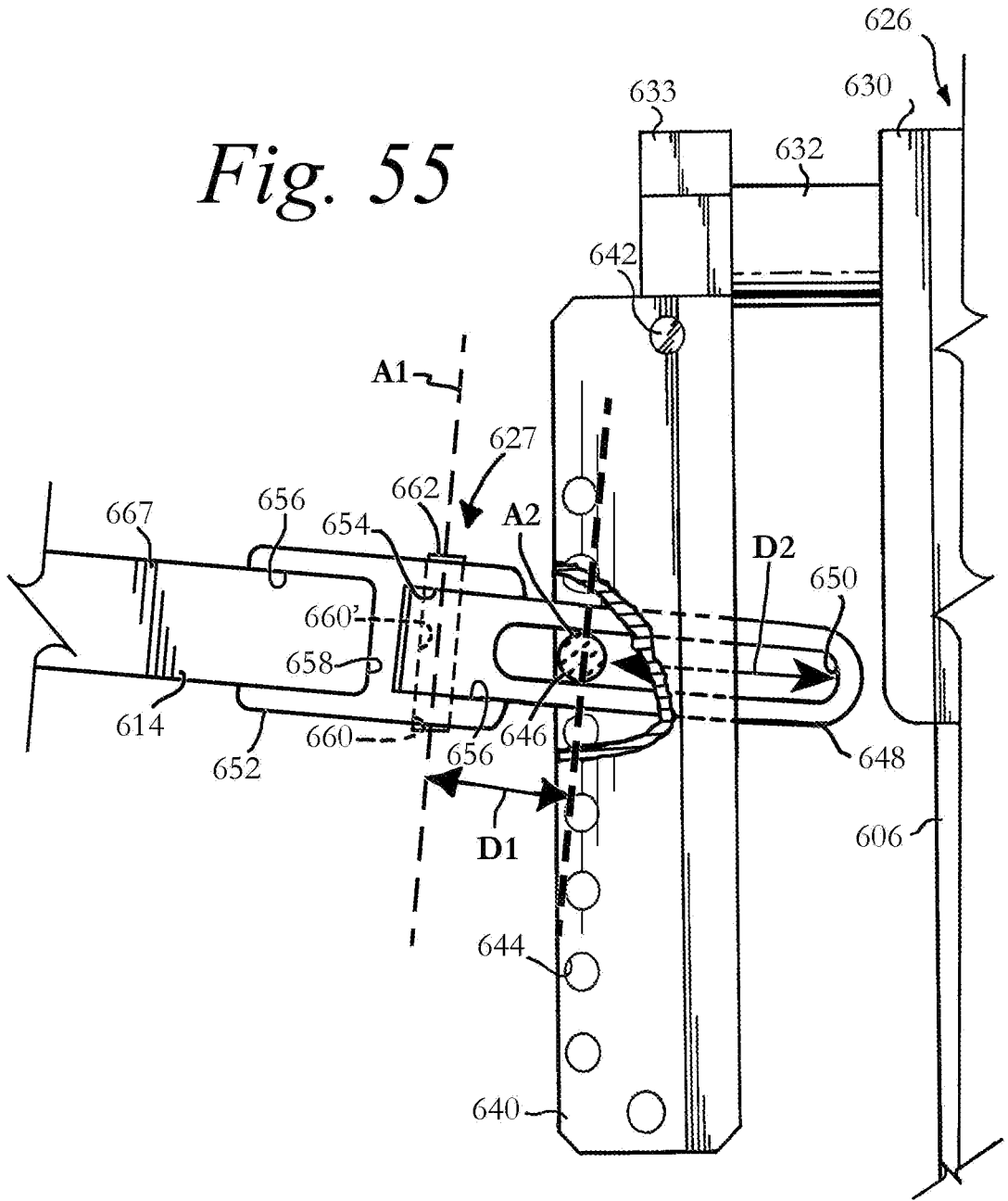

PATIENT POSITIONING SUPPORT STRUCTURE

CROSS-REFERENCE TO RELATED APPLICATIONS

This application is a divisional of U.S. Ser. No. 15/479,007, filed on Apr. 4, 2017, which is a continuation of U.S. Ser. No. 14/538,310, filed Nov. 11, 2014, which is a continuation-in-part of U.S. Ser. No. 14/096,875, filed Dec. 4, 2013, and which is a continuation of U.S. Ser. No. 13/317,012, filed Oct. 6, 2011, now U.S. Pat. No. 8,719,979, all of which are incorporated by reference herein. U.S. Ser. No. 13/317,012 is a continuation of U.S. Ser. No. 12/460,702, filed Jul. 23, 2009, now U.S. Pat. No. 8,060,960, which is a continuation of U.S. Ser. No. 11/788,513, filed Apr. 20, 2007, now U.S. Pat. No. 7,565,708, which claimed the benefit of U.S. Provisional Application No. 60/798,288 filed May 5, 2006 and was also a continuation-in-part of pending U.S. patent application Ser. No. 11/159,494 filed Jun. 23, 2005, now U.S. Pat. No. 7,343,635, that is a continuation-in-part of U.S. patent application Ser. No. 11/062,775 filed Feb. 22, 2005, now U.S. Pat. No. 7,152,261, all of which are incorporated by reference herein. Application Ser. No. 14/538,310 is a continuation-in-part of U.S. Ser. No. 14/050,998, filed Oct. 10, 2013, and which is a continuation-in-part of U.S. Ser. No. 13/317,012, filed Oct. 6, 2011, now U.S. Pat. No. 8,719,979, all of which are incorporated by reference herein.

BACKGROUND OF THE INVENTION

The present invention is directed to structure for use in maintaining a patient in a desired position during examination and treatment, including medical procedures such as imaging and surgery and in particular to such a structure that allows a surgeon to selectively position the patient for convenient access to the surgery site and providing for manipulation of the patient during surgery including the tilting, pivoting, angulating or bending of a trunk and/or a joint of a patient in a supine, prone or lateral position.

Current surgical practice incorporates imaging techniques and technologies throughout the course of patient examination, diagnosis and treatment. For example, minimally invasive surgical techniques, such as percutaneous insertion of spinal implants, involve small incisions that are guided or navigated by continuous or repeated intra-operative imaging requiring patient positioning for image registration and navigation. These images can be processed using computer software programs that produce three dimensional images for reference by the surgeon during the course of the procedure. If the patient support structure having an open frame or a flat top surface is not radiolucent or compatible with these imaging technologies, it may be necessary to interrupt the surgery periodically in order to remove the patient to a separate patient support structure for imaging followed by transfer back to the operating support surface for resumption of the surgical procedure. Such patient transfers for imaging purposes may be avoided by employing radiolucent and other imaging compatible patient support systems. The patient support system should also be constructed to permit unobstructed movement of the imaging equipment and other surgical equipment around, over and under the patient throughout the course of the surgical procedure without contamination of the sterile field and without pulling out tubes and lines.

It is also necessary that the patient support system be constructed to provide optimum access to the surgical field by the surgery team. Some procedures require positioning of portions of the patient's body in different ways at different times during the procedure. Some procedures, for example, spinal surgery, involve access through more than one surgical site or field. Since all of these fields may not be in the same plane or anatomical location, the patient support structures should be adjustable and capable of providing support in different planes for different parts of the patient's body as well as different positions or alignments for a given part of the body. Preferably, the support structure should be adjustable to provide support in separate planes and in different alignments for the head and upper trunk portion of the patient's body, the lower trunk and pelvic portion of the body as well as each of the limbs independently.

Certain types of surgery, such as orthopedic surgery, may require that the patient or a part of the patient be repositioned during the procedure while in some cases maintaining the sterile field. Where surgery is directed toward motion preservation procedures, such as by installation of artificial joints, total disc prostheses and soft and dynamic stabilization system, for example, the surgeon must be able to manipulate certain joints while supporting selected portions of the patient's body during surgery in order to facilitate the procedure. It is also desirable to be able to test the range of motion of the surgically repaired or stabilized joint and to observe the gliding movement of the reconstructed articulating prosthetic surfaces or the tension and flexibility of spacers and other types of elastic or dynamic stabilizers before the wound is closed. Such manipulation can be used, for example, to verify the correct positioning and function of an implanted prosthetic disc, spinal dynamic longitudinal connecting member, interspinous spacer or joint replacement during a surgical procedure. Where manipulation discloses binding, sub-optimal position or even crushing of the adjacent vertebrae, for example, as may occur with osteoporosis, the prosthesis can be removed and the adjacent vertebrae fused while the patient remains anesthetized. Injury which might otherwise have resulted from a "trial" use of the implant post-operatively will be avoided, along with the need for a second round of anesthesia and surgery to remove the implant or prosthesis and perform the revision, fusion or corrective surgery.

There is also a need for a patient support structure that can be rotated, angulated, articulated and translated so that the patient can be moved from a prone to a supine position or from a prone to a 90° position and whereby intra-operative extension and flexion of at least a portion of the spinal column can be achieved. The patient support structure must also be capable of easy, selective adjustment without necessitating removal of the patient or causing substantial interruption of the procedure.

For certain types of surgical procedures, for example spinal surgeries, it may be desirable to position the patient for sequential anterior and posterior procedures. The patient support structure should also be capable of rotation about an axis in order to provide correct positioning of the patient and optimum accessibility for the surgeon as well as imaging equipment during such sequential procedures.

Orthopedic procedures may also require the use of traction equipment such as cables, tongs, pulleys and weights. The patient support system must include structure for anchoring such equipment and it must provide adequate support to withstand unequal forces generated by traction against such equipment.

Articulated robotic arms are increasingly employed to perform surgical techniques. These units are generally designed to move short distances and to perform very precise work. Reliance on the patient support structure to perform any necessary gross movement of the patient can be beneficial, especially if the movements are synchronized or coordinated. Such units require a surgical support structure capable of smoothly performing the multi-directional movements which would otherwise be performed by trained medical personnel. There is thus a need in this application as well for integration between the robotics technology and the patient positioning technology with synchronization by software programs.

While conventional operating tables generally include mechanisms that permits tilting or rotation of a patient support structure about a longitudinal axis, previous surgical support devices have attempted to address the need for unrestricted access by providing a cantilevered patient support structure on one end of a base. Such designs typically employ either a massive base to counterbalance the extended support member or a large overhead frame structure to provide support from above. The enlarged base members associated with such cantilever designs can be problematic with respect to the movement of C-arm, CT scanners and O-arm mobile fluoroscopic imaging devices as well as other equipment. In addition, their patient support structures have not provided for much articulation or flexion and extension of the patient being supported. Surgical tables with overhead frame structures are bulky and may require the use of dedicated operating rooms, since in some cases they cannot be moved easily out of the way. Neither of these designs is easily portable or storable.

Thus, there remains a need for a patient support system that provides easy access for personnel and equipment, that can be easily and quickly positioned and repositioned in multiple planes without the use of massive counterbalancing support structure, and that does not require use of a dedicated operating room. In this regard, providing support on both outer ends of the patient support structure suspended therebetween can provide some advantages as further outlined herein.

SUMMARY OF THE INVENTION

Prior developments for surgical tables have provided a patient support structure having one or more inward articulations that allow for the support structure to break or angulate. The articulation typically occurs between a head end section and a foot end section of the support structure. The articulation can have a virtual pivot axis, an actual pivot axis or a point along one of these axes. The articulation having a virtual pivot axis keeps the gap between the inner ends of the head and foot end sections or portions a fixed distance apart while they are being articulated into a flexed or extended position or orientation. Such an arrangement has several advantages in that the virtual pivot axis can be entirely radiolucent and it does not directly need to carry or support any load. Binding at the articulation is also not a concern when the outer ends of the head and foot sections, connected to a base, are at different elevations above the floor and the patient support structure itself is rolled or tilted. Load-sharing for this type of articulated patient support structure is concentrated or its outer ends connected to the base by a connection assembly providing rotation structures, angulation or pivot structure and translation compensation structure within the connection assembly between the base and the outer ends of the patient support structure.

The patient support structure having an inward articulation with an actual pivot axis can have a pin about which angulation occurs. Again, the inner ends of the head and foot end section remain a fixed distance apart during the angulation at this inward articulation. This articulation is typically a hinge or joint structure. The hinge or joins structure can extend across the patient support structure or preferably be a pai9r of spaced apart hinges or joints. This articulation can also be radiolucent. It can participate in load-sharing equally with the outer ends of the patient support structure connected to the base by a connection assembly, or it can remain relatively unloaded while the load-sharing is done at said outer ends. This inward articulation can have an actuator that directly or indirectly moves it. The actuator can be located at or near the articulation or at to near the connection assembly between the base and the outer end or ends of the patient support structure. In either case, direct vertical structural support at both outer ends of the patient support structure is fundamental for the surgical table embodiments disclosed in this application. This occurs through multi-functional connection assemblies at both outer ends of the patient support structure.

While manipulation of the patient when on the support structure suspended between outer end supports of the base is desirable, too much vertical and horizontal travel for the patient is not, as this can lead to unwanted consequences concerning anaesthesia, tubing, IV lines in the patient, and son on. Having translation occur at or near both outer ends of the patient support structure can help minimize at least the horizontal travel that might otherwise need to occur at or around the inward articulations, especially with breaking or angulation for patient positioning and during patient manipulations. This translation at both outer ends of the patient support structure can occur in different ways. For example, both outer ends of the patient support structure and the base end supports can translated inwardly simultaneously so as to keep the articulation from moving very much horizontally with angulation thereabout. This is generally favorable for the surgeon, but may not be for other members of the surgical team.

Another way this necessary translation can occur is by dual translation connector mechanisms at both outer ends fo the patient support structure, wherein the base end supports do not need to travel along the floor. The translation connectors can have activators or not, and the actuators can also provide for angulation and rotation at the connection assemblies between the base and the outer end of the patient support structure. When the actuators provide for the angulation between the base and the patient support structure at its outer ends, the inward articulations for the patient support structure need not carry much load. This allows for the hinge or joint mechanism to be fairly simple, wherein it can have a radiolucent pin about which the angulation can occur. Again, the connection assemblies between the outer ends of the patient support structure and the base can include horizontal translation connector subassemblies, in addition to powered mechanisms for angulation and rotation and in some cases even vertical translation for height adjustment above the floor.

The translation connectors in the different table embodiments disclosed herein can also have a plurality of rotational or pivot axes, wherein the axes can translated horizontally with respect to each other. For example, a transverse axis of rotation can be located at or between the attachment of the translation connector mechanism to the end support of the base and a perpendicular axis of rotation can be located at or between the attachment of the translation connector mechanism to the outer end of the patient support structure. In this way, the translation connector mechanism can provide for at least two degrees of freedom for rotational movement between the outer ends of the patient support structure and the base, which is necessary when the patient support structure inward articulation is angulated and rolled, fore example. The roll can occur at the translation connector mechanism, at its outer end attachments or somewhere else in the connecting assembly, such as at the top of the base end supports. In this regard, the various structural components of the connection assemblies can be completely or partially powered.

Therefore, the present invention is directed to patient support systems that permit adjustable positioning, repositioning and selectively lockable support of a patient's head and upper body, lower body and limbs in up to a plurality of individual planes while permitting inclination, roll or tilting, rotation or angulation, breaking or bending and other manipulations as well as full and free access to the patient by medical personnel and equipment. The system of the present invention may be cantilevered, wherein load-sharing is primarily at the outer end of the patient support structure, or non-cantilevered and include a pair of spaced apart support ends, piers or columns that are each height adjustable. The illustrated embodiments include a pair of opposed independently height-adjustable end support columns. The columns may be independent or connected to a horizontally length-adjustable base in one embodiment. One support column according to the invention may be coupled with a wall mount or other stationary support. In each case, a patient support structure is connected to and bridges substantially between the pair of end supports. For example, in a preferred embodiment according to the invention, the patient support structure is hingedly suspended between the end supports.

The patient support structure may be a frame or other patient support that is semi-constrained, having at least first and second hingeable or otherwise joined or connected portions or sections, the first and second portions being selectively lockable in a first substantially planar orientation along a longitudinal or horizontal axis of the support structure that resembles conventional constrained or fixed patient support structures. However, the hinged or semi-constrained support structure of the invention provides for the first and second portions that are also positionable and lockable in a plurality of angles with respect to one another, with each portion being movable to a position on either side of the first planar orientation. In other words, the patient support structure is capable of articulating, hinging or otherwise bending to form an angulation, break or joint, either upwardly or downwardly from a vertical starting position above the floor and also when the support structure is in an inclined or declined position due to one of the support columns raising one end of the structure higher than another end. Furthermore, in addition to an "up" or "down" break, such a break or joint created by the two portions may be oriented from side-to-side, as when the support structure is rolled or rotated about a longitudinal axis thereof.

In a particular illustrated embodiment, articulation, jointing or breaking of the patient support structure at an inward or central location between the pair of stationary end supports is supported by a cable drive system (tension band suspension). The tension band structure can be metal or radiolucent polymer. In another embodiment, a pull-rod assembly supports articulation to control the break or articulation angle and render the patient support structure rigid. Again, the pull-rod can be radiolucent. Such an embodiment further includes a substantially fixed slider bar disposed at an end of the patient support, the patient support structure being supported by and slidingly movable along such slider bar with the bar following the angle of inclination of the patient support at such end. Other embodiments include cantilevered systems with connected or unconnected movable or translating base supports. The first and second patient support structure portions may be in the form of frames, such as rectangular frames or other support structure that may be equipped with support pads for holding the patient, or other structure, such as imaging tops which provide a flat radiolucent surface.

The patient support structure and the base support columns are coupled or connected with respective roll or rotation, articulation, pivot or angulation adjustment and horizontal translation structures in the form of connection and assemblies for positioning the first support portion with respect to a first column or end support and with respect to the second support portion and the second support portion with respect to the second column or end support. Rotation adjustment structure in cooperation with pivoting and height adjustment structure provided by the connection assemblies allow for the lockable positioning of the first and second patient support portions at a variety of selected positions and articulations with respect to the support columns including angulation or pivot coupled with Trendelenburg and reverse Trendelenburg configurations as well as providing for patient roll over in horizontal or tilted orientation. Lateral movement or translation (toward and away from a surgeon) and longitudinal translation may also be provided by powered actuators in the base end support columns. A pair of patient support structures (such as a support frame and an imaging table) may be mounted between end supports of the invention and then rotated in unison about a longitudinal axis to achieve 180° repositioning of a patient, from a prone to a supine position in some embodiments.

In another embodiment, an apparatus for supporting a patient during a medical procedure is provided, the apparatus including a base structure with first and second spaced opposed end supports; each end support being attached to the base structure; an elongate patient support structure including first and second portions joined inwardly at an articulation, the patient support structure outwardly connected to the end supports by connection assemblies and being alignable in a first plane and movable to a plurality of angular orientations with respect to one another on either side of the first plane; the inward articulation joining the first and second portions and movable to a plurality of angular orientations associated with the angular orientations of the outwardly connected ends of the patient support structure relative to the end supports and a translation connector subassembly connecting each outer end of the patient support structure to the base and cooperating with the inward articulation and outwardly connected ends of the patient support structure, as a component of the connection assemblies, so as to allow the patient support structure to move through the various angular orientations thereof without the spaced opposed end supports moving relative to each other with respect to a spaced opposed distance; and a structure to move the articulation into the various angular orientations.

In a further embodiment, at least one of the end supports includes a first vertical height adjustor and a second vertical height adjustor is positioned between the spaced opposed end supports.

In a further embodiment, a single translation connector subassembly can be used in the form of a slider bar, rigidly attached to one outer end of the first and second portions, the slider bar pivotally attached with transverse and perpendicular axes to one of the end supports and providing a large amount of translation at one end of the table so as to make up for not having translation at the opposed or opposite end.

In a further embodiment, at least one of the end supports further includes a rotation mechanism.

In a further embodiment, the patient support structure is detachable and positionable at either end in a plurality of locations vertically spaced from a floor.

In a further embodiment, the articulation has a hinge or joint mechanism, load-sharing and not, that cooperates with the various angular orientations.

Yet another embodiment provides an apparatus for supporting a patient during a medical procedure, including a support subassembly including first and second spaced opposed upright end supports; each end support being attached to a respective base structure; at least one of the first and second end supports being vertically height adjustable; an elongate patient support with first and second ends and extending between the first and second end supports; the patient support being held by the end supports in spaced relation with respect to a floor, the patient support connected to and supported between the end supports; the patient support having a single breaking location spaced from the end supports and adapted to interact with the patient when the patient is located on the patient support; and a vertical elevator connecting a patient support first end with a respective end support; the vertical elevator being controllable to allow continuous non-segmented adjustment of the support first end relative to the respective end support so as to align and orient the patient support subassembly; and wherein the patient support is controllable to be upwardly and downwardly articulatable at both the first and second ends of the patient support relative to respective end supports and at the breaking location so as to be adapted to manipulate a patient into a plurality of selectively prone and non-prone positions in cooperation with a pivoting end support translation compensation mechanism at both outer ends of the patient support structure, while also cooperating with the end supports to move the patient between vertical positions.

Still another embodiment provides an apparatus for supporting a patient during a medical procedure, the apparatus including a support subassembly including first and second spaced opposed end supports; each end support being attached to a respective base structure; at least one of the first and second end supports being vertically height adjustable; an elongate patient support with first and second ends and extending between the first and second end supports; the patient support being held by the end supports in spaced relation with respect to a floor, the patient support connected to and supported between the end supports; the patient support having a single breaking location spaced from the end supports and adapted to interact with the patient when the patient is located on the patient support; and a vertical elevator connecting a patient support first end with a respective end support; the vertical elevator being controllable to allow continuous adjustment of the support first end relative to the respective end support so as to align and orient the patient support subassembly; and wherein the patient support is controllable to be upwardly and downwardly articulatable at both the first and second ends of the patient support relative to respective end supports and at the breaking location so as to be adapted to manipulate a patient into a plurality of selectively prone and non-prone positions in cooperation with a patient support translation compensation mechanism at both outer ends thereof, while also cooperating with the end supports to move the patient between vertical positions, and wherein at least one translation compensation mechanism is moved by an actuator in a longitudinal direction.

Objects and Advantages of the Invention

Therefore, it is an object of the present invention to overcome one or more of the problems with patient support systems described above. Further objects of the present invention include providing breaking or hinged patient support structures; providing such structures wherein such break or joint may be in any desired direction; providing such structures that include at least one base support structure that allows for vertical height adjustment; providing such a structure wherein such base support is located at both outer ends of the patient support, allowing for patient positioning and clearance for access to the patient in a wide variety of orientations; providing such a structure that may be rotated about an axis as well as moved upwardly or downwardly at either end thereof; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a breaking patient support structure according to the invention and having load-sharing hinges and translation compensation mechanisms on both outer ends of the patient support structure.

FIG. 2 is an enlarged and partial side elevational view of a portion of the support structure of FIG. 1.

FIG. 3 is an enlarged and partial top plan view of the support structure of FIG. 1.

FIG. 4 is an enlarged and partial perspective view of a portion of the structure of FIG. 1.

FIG. 5 is an enlarged and partial side elevational view of a portion of the structure of FIG. 1 showing a translation connector subassembly with longitudinally translating transverse and perpendicular axes with respect to each other.

FIG. 6 is an enlarged and partial perspective view of a portion of the structure of FIG. 1.

FIG. 7 is an enlarged and partial perspective view of a radiolucent first hinge of the structure of FIG. 1.

FIG. 8 is an enlarged and partial perspective view of a cooperating radiolucent second hinge of the structure of FIG. 1.

FIG. 9 is an enlarged and partial elevational view of the hinge of FIG. 7.

FIG. 10 is an enlarged and partial perspective view of an outer portion of the hinge of FIG. 7 with portions broken away to show the detail thereof.

FIG. 13 is a partial perspective view of a patient support frame of the structure of FIG. 1.

FIG. 14 is a partial perspective view of a patient imaging top for replacement with the patent support frame of FIG. 13.

FIG. 15 is a reduced perspective view of the structure of FIG. 1 shown with an imaging top of FIG. 14 replacing the support frame of FIG. 13 and shown in a planar inclined position.

FIG. 16 is a perspective view of the structure of FIG. 15 shown in a planar tilted position.

FIG. 17 is a perspective view of the structure of FIG. 15 shown in a planar inclined and tilted position.

FIG. 21 is a side elevational view of the structure of FIG. 15 shown in a symmetrical downward breaking position.

FIG. 22 is a side elevational view of the structure of FIG. 15 shown in a first inclined and downward breaking position.

FIG. 23 is a side elevational view of the structure of FIG. 15 shown in a second inclined and downward breaking position.

FIG. 24 is an enlarged side elevational view of the structure of FIG. 1 shown in an upward breaking, inclined and tilted position.

FIG. 25 is a is a perspective view of a second embodiment of a patient support structure according to the invention including a patient support frame and an imaging table shown in a first spaced orientation.

FIG. 26 is a perspective view of the patient support structure of FIG. 25 shown tilted in an intermediate position during a rotation as would be used for a patient rollover.

FIG. 27 is a perspective view of the structure of FIG. 25 shown further rolled or tilted in a second intermediate position during rotation.

FIG. 28 is a perspective view of the structure of FIG. 25 shown after rotation to a final flipped position.

FIG. 29 is a perspective view similar to FIG. 25 showing the articulating patient support frame and the articulating imaging table in a second spaced orientation.

FIG. 30 is a front elevational view of a third embodiment of a patient support structure according to the invention showing a pair of opposed translating (inwardly and vertically) end supports and a patient support structure articulation that does not share much loading due to angulation actuators at both outer ends thereof.

FIG. 31 is a front elevational view of a fourth embodiment of a patient support structure according to the invention.

FIG. 32 is a perspective view of a fifth embodiment of a patient support structure according to the invention, shown in a planar inclined position, wherein the patient support structure can, again, have translation compensation at both of its outer ends.

FIG. 33 is a perspective view of the structure of FIG. 32 shown in an inclined and upward breaking position at an inward articulation that is only partially load-sharing due to an angulation actuator in one end of the base which carries most of the weight when loaded.

FIG. 34 is a perspective view of the structure of FIG. 32 shown in a substantially symmetrical downward breaking position.

FIG. 35 is a reduced side elevational view of a sixth embodiment of a patient support structure having a load-sharing inward articulation according to the invention shown in a substantially horizontal and planar position and a large amount of translation compensation available on only one outer end of the support structure.

FIG. 36 is a reduced side elevational view of the structure of FIG. 35 shown in a symmetrical downward breaking position.

FIG. 37 is a reduced side elevational view of the structure of FIG. 35 shown in a symmetrical downward breaking position.

FIG. 38 is an enlarged and partial top plan view of a portion of the structure of FIG. 35 and shown in the same position as shown in FIG. 35.

FIG. 39 is an enlarged and partial side elevational view of the structure of FIG. 35 and shown in the same position as shown in FIG. 35.

FIG. 40 is an enlarged and partial side elevational view of the structure of FIG. 35 and shown in the same position as shown in FIG. 35.

FIG. 41 is an enlarged and partial perspective view of the structure shown in FIG. 40.

FIG. 45 is an enlarged and partial top plan view of a portion of the structure of FIG. 35 and shown in the same position as shown in FIG. 37.

FIG. 46 is an enlarged and partial side elevational view of the structure of FIG. 35 and shown in the same position as shown in FIG. 37 and showing all of the translation compensation occurring on the foot end of the patient support structure.

FIG. 47 is an enlarged and partial side elevational view of the structure of FIG. 35 and shown in the same position as shown in FIG. 37.

FIG. 53 is a side view of the structure of FIG. 48 shown in a horizontal and planar position, and including reversibly attached torso support translator with an actuator and the hip-thigh pad structures of FIG. 48 positioned on the foot end portion of the frame adjacent the articulation, wherein D3 stays constant with frame articulation.

FIG. 54 is a side view of the structure of FIG. 48 shown in an inclined and upward breaking position, and including reversibly attached upper body support and hip-thigh pad structures of FIG. 48.

FIG. 55 is an enlarged side elevational view of the translation connector component of FIG. 5 to FIG. 33 and FIG. 48, with portions broken away or shown in cross-section, so as to show greater detail thereof.

DETAILED DESCRIPTION OF THE ILLUSTRATED EMBODIMENTS

Figure 11:
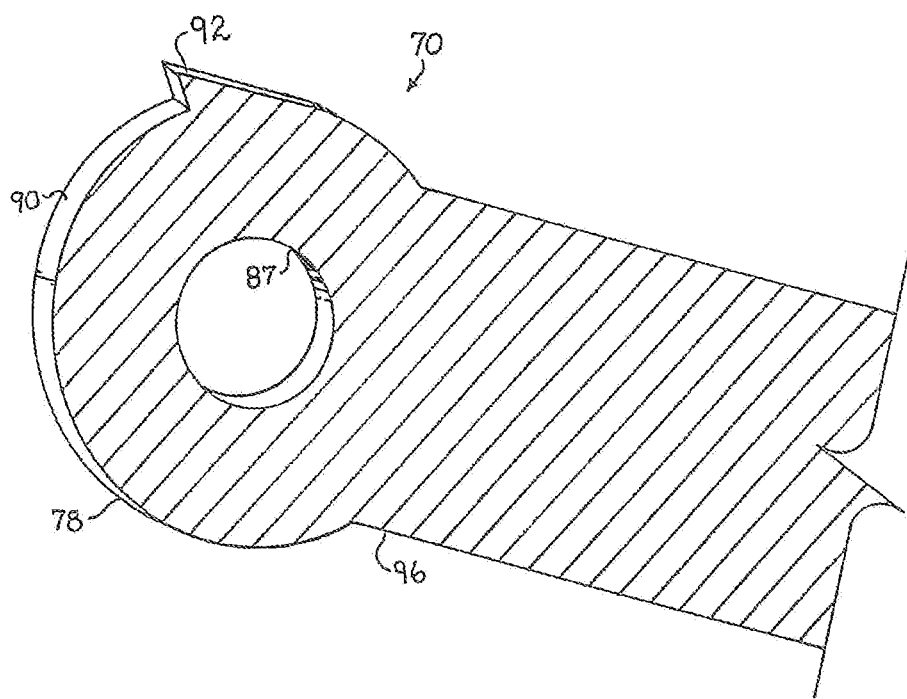
FIG. 11 is an enlarged and partial perspective view of an inner portion of the hinge of FIG. 7 with portions broken away to show the detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawings, a patient positioning support structure according to the invention is generally designated by the reference numeral 1 and is depicted in FIGS. 1-12. The structure 1 includes first and second support piers or column assemblies 3 and 4 which are illustrated as independent, stationary floor base support structures as shown in FIG. 1 or may be connected to one another by a base support as illustrated in the embodiment shown in FIG. 30. In some embodiments according to the invention as shown, for example, in FIGS. 32-34, the base connection provides the columns with a motorized length adjustment compensation at both outer ends thereof. Additionally or alternatively, the base connection may be non-motorized and selectively retractable, such that the length of the base connection can be shortened, such as but not limited to for storing the base with a smaller footprint that the base has when in use. It is also foreseen that in certain embodiments according to the invention, one of the support columns may be replaced by a conventional operating room table as known in the art, having transverse and longitudinal translation (see FIGS. 32-34 and 48-54), or may even be a wall mount.

In the first illustrated embodiment, each of the support columns 3 and 4 includes a translation angulation connection subassembly TAC (see FIGS. 5 and 6), which includes a pivotal support assembly, a rotation subassembly and an angulation subassembly, which are described in greater detail below. The support column 3 includes an attached first pivotal support connection assembly, generally 5, and the support column 4 includes an attached second pivotal support assembly, generally 6. Between them, the support connection assemblies 5 and 6 uphold an optionally removable elongate, articulate jointed or breaking patient holding or support structure, generally 10 and optionally, a second removable patient support structure that will be described with respect to another embodiment of the invention. The patient support structure 10 includes a rigid outer frame with an inwardly located articulation 16, such as but not limited to a real hinge or a virtual articulation (not shown, and which may be referred to as a virtual "hinge") and is connected to the base end supports by connection assemblies 5 and 6, which are described in greater detail below. The articulation is defined by being limited to vertical translation as opposed to longitudinal translation, or a combination of vertical and longitudinal translation. "Vertical translation" means movement of a structure such that the height of the structure is increased or decreased relative to the floor. Longitudinal translation is generally movement that runs parallel to the floor or to the longitudinal axis of the surgical table 1. It is noted that in this embodiment, the connection assemblies 5 and 6 equally share the load inwardly and outwardly, as opposed to load-bearing that is solely or primarily outwardly at the connection assemblies 5 and 6.

The support connection assemblies 5 and 6 include structures to provide for putting the outer ends of the support structure 10 into simultaneous roll, Trendelenburg, reverse Trendelenburg, pivot or angulation and at least horizontal translation with respect to each of the columns 3 and 4. The illustrated support structure 10 includes a first frame section 12, a second frame section 14 with an optional transverse support cross bar 15, and a pivot or hinge assembly, generally 16. In the illustrated embodiment, the pivot assembly further an actuator in the form of includes a cable drive system, including a dual winch 18 and cooperating cables 20; however, other drive systems are foreseen.

The columns 3 and 4 are supported by outwardly extending feet 22 that may or may not include spaced apart casters or wheels (not shown) each equipped with a floor-lock foot lever for lowering the feet 12 into a floor-engaging position as shown in FIG. 1. The columns 3 and 4 each include two or more motorized lift arm segments 3a, 3b and 4a, 4b, respectively that permit the height of each of the columns 3 and 4 to be selectively increased and decreased in order to raise and lower all or a selected portion of the connected patient support structure 10 and position it into an inclined orientation. It is foreseen that the vertical supports 3 and 4 may be constructed so that the column 3 has a greater mass than the support column 4 or vice versa in order to accommodate an uneven weight distribution of the human body. Such reduction in size at the foot end of the system 1 may be employed in some embodiments to facilitate the approach of personnel and equipment. It is foreseen that other types of end column vertical height adjustment mechanisms can also be used for the columns.

Each of the support piers or columns include a support connection assembly 5 and 6. Each connection assembly 5 and 6 includes two or more subassemblies for moving the patient support 10 in a particular manner. Each connection assembly 5 and 6 includes a rotation subassembly 26 and 26' and an angulation subassembly 27 and 27', respectively, that are interconnected as will be described in greater detail below and include associated power source and circuitry linked to a controller 29 (FIG. 1) for cooperative and integrated actuation and operation so as to maintain the hinges at a selected height and horizontal relationship with respect to the floor. The rotational subassemblies 26 and 26' enable coordinated rotation of the patient support structure 10 about a longitudinal axis of the structure 1 and one generally located near an outer end of the patient support structure. The angulation subassemblies 27 and 27' shown in FIGS. 2 and 3 include translation structure and enable the selective hinging, articulation or breaking of the support 10 at the hinge assembly 16 at desired levels and increments as well as selective tilting of the frame portions 12,14 with respect to a longitudinal axis of such frame portion with longitudinal translation compensation occurring at both outer ends of the frame portions.

The rotation subassembly or mechanism 26, shown in FIGS. 1 and 5, includes at least one motor housing 30 surmounting the support column 3; however, the rotation mechanism could be located closer to the patient support structure. In the illustrated embodiment, only one rotational motor is provided, but it is foreseen that a cooperating motor may also be mounted on the support column 4. It is also foreseen that the rotational mechanism could be located somewhere other than in support columns 3 and 4. A main rotational shaft 32 is shown extending from the motor housing 30 that turns a rotation structure 33 in this particular embodiment. The rotation structure 33 in turn rotates the connected patient support 10 about a longitudinal axis as will be described in greater detail below. The motor housing 30 contains a rotary electric motor or other actuator drivingly engaged with the shaft 32. It is foreseen that the shaft could be located above or below the outer end of the patient support structure. The rotation mechanism 26 is operated by actuating the motor using a switch or other similar means and can be controlled by a computer. The rotation structure 33 is fixed to the shaft 32 at a location spaced from the motor housing 30 and the support column 3 to provide clearance for rotation of the connected patient support structure 10 in this embodiment.

As shown in FIGS. 4 and 5, the rotation structure 33 can be attached to a pair of translation posts or H-bar posts 40 disposed at either end of the rotation structure 33; however, other connections are foreseen. The posts 40 are each attached to the structure 33 by a pin 42, bolt, or other fixing structure. One or more cooperating apertures 44 formed in the posts 40 can provide passageway for a pivot pin 46 to extend therethrough. The pivot pin 46 is receivable in each cooperating pair of apertures 44 allowing for selective placement of a pivoting translation connector component 48 and 52 that, in this embodiment, is sized and shaped to be received between the pair of posts 40 and also receive the pivot pin 46 therethrough. This enables the translation connector mechanism to have a transverse axis of rotation. The pin 46 and connector 48, 52 are thus positionable in different angular orientations with respect to the longitudinal extension of the support 10, wherein this connection mechanism can also translate horizontally at a variety of vertical heights to be selected by the surgeon and readily changeable, even during surgery if necessary, to vary the height of the frame section 12. In one specific embodiment, the multiple location or height feature is also advantageous when more than one frame or patent structure is mounted in tandem as shown, for example in FIGS. 25-29. In this embodiment, the position of the frame or other structure may be desirably changed to provide close proximity to an imaging top with a distance between a patient support and an imaging top being expandable or reduceable depending upon the size or other attributes of a patient and surgical or other requirements. As illustrated in FIG. 5, in one embodiment, the connector component or assembly 48, 52 has a slot 50 for receiving a pivot pin 46, to provide for a passive transverse axis of rotation within the translation compensation mechanism. Further, the slot 50 and pivot pin 46 provide for manual, or passive, height adjustment, or vertical translation, of the connector 48, by manually lifting the connector 48 so that the slot 50 is aligned with the apertures 44 of the H-bar posts 40, and then passing or installing the pivot pin 46 through all three of the aligned apertures 44 and slot 50.

Also with reference to FIGS. 4 and 5, the translation connector subassembly 48, 52 includes rigid attachment to an outer end of the patient support structure. In this embodiment, the attachment includes an additional pivot axis structure 52 with an open ended slot 56, although other attachments to the patient support structure are foreseen. The slot 56 is sized and shaped for receiving an end connection 58 of the frame section 12. The pivoting translation connector subassembly 48, 52 further includes a through aperture or bore 60 running substantially perpendicular to the slot. The aligned apertures 60, 60' are sized and shaped to receive a pivot pin 62 therethrough oriented at a 90° angle with respect to the transverse pivot pin 46. The swivelable connection for the translation connector subassembly provided by the pin 62 provides for some passive forward and rearward lateral movement and rotational movement of the attached frame end connection 58 and thus the frame section 12, providing a degree of freedom and clearance needed for rotating the patient support about a longitudinal axis of a patient, with certain patient manipulations. The inner portion of the multifunctional translation connector subassembly is sized and shaped to frictionally engage the frame end connection 58, thus securely fixing the end connection 58 to the pivoting translation connector component of the connection assembly. The frame end connection 58 is in turn fixed to each of elongate frame members 66 and 68 of the frame section 12. The frame members 66 and 68 are each hingedly connected to the inward hinge assembly 16 to be described in greater detail below. Pivoting of the translation connector subassembly 48, 52 with respect to the pin 46, or the transverse translation axis A2, and the perpendicular axis A1 provides for selected articulation (see FIGS. 5-6), or passive modifications in pitch, of the frame section 12 (that includes the end connection 58 and the frame members 66 and 68) and/or the entire support 10 with respect to the support pier or column 3, wherein the entire patient support structure is inwardly articulated and rolled with respect to the longitudinal or roll axis R (see FIGS. 1 and 6). It if foreseen that, depending upon the table, all of the subassemblies can be powered (i.e., actively driven) or passive (i.e., movement with respect to the axis is driven by movement occurring in another part of the structure 1).

With reference to FIG. 6, at the support pier or column 4, the support assembly 6 is substantially similar to the support assembly 5; however, the rotation subassembly 26' can include a motor or not include a motor. The support pier or column 4, again, includes a powered mechanism to provide selective height adjustment of the subassembly 26'. A rotation structure 33' is inwardly spaced from the column 4. The structure 33' includes a shaft (not shown) extending outwardly therefrom similar to the rotation shaft 32, the shaft being, again, rotatingly related to both the patient support structure and the support column 4.

In this particular arrangement shown, the rotation subassembly 26' and the angulation subassembly 27' otherwise include elements identical to or substantially similar to the elements of the subassemblies 26 and 27. Specifically, H-bar posts 40', pin 42', apertures 44', pivot pin 46', translation connector subassembly 48', 52', end connector 58' and pivot pin 62', are identical or substantially similar in form and cooperate with other elements identically or substantially similarly to what has been described previously herein with respective H-bar posts 40, pin 42, apertures 44, pivot pin 46, translation connector subassembly 48, 52, end connector 58 and pivot pin 62.

The frame 14 further includes frame members 66' and 68' that are each fixed to the end connector 58'. The frame members 66' and 68' are pivotally or hingedly connected to respective frame members 66 and 68 by the hinge assembly 16. Specifically, the frame member 66 is attached to the frame member 66' by the hinge mechanism 70 and the frame member 68 is attached to the frame member 68' by the hinge mechanism 72, which, again, are preferably radiolucent.

With particular reference to FIGS. 3, 7 and 9-11, the hinge mechanism 70 includes an outer member 76 and an inner member 78. The outer member 76 is fixed or may be integral with the elongate frame member 66, while the inner member 78 is integral or otherwise fixed to the frame member 66'. The outer member 76 further includes an extension 80 with a groove 82 for receiving and guiding the cable 20. The extension 80 tapers in a direction from the outer member interior 84 to the groove 82. The extension 80 is configured to cause a slight upward break or bend of the support 10 when the extension 80 comes into contact with the cable 20 at the groove 82. In that way, when the cables 20 are reeled in to shorten the hypotenuse of the triangle formed by the cable, the section 12 and the section 14, the sections 12 and 14 move toward one another, resulting in the upward break as illustrated, for example, in FIG. 18. The downward break or joint illustrated, for example, in FIG. 21 is a result of lengthening the cable 20 distance and allowing gravity to drop the hinge 70. The extension 80 is shaped to extend slightly inwardly toward a longitudinal axis A of the support 10, thereby guiding the cable 20 along a path within a periphery of the frame sections 12 and 14 when the extension 80 is in contact with the cable 20 when in a downward breaking configuration directed toward the cable with the cable 20 being received at the groove 82.

It is foreseen that if an exclusively upward breaking or jointing embodiment is desired according to the invention, the sections 12 and 14 may be positioned with respect to two end columns to always include a slight upward break, joint or bend at the hinge or pivot between the sections 12 and 14. When the base is actuated to move the columns toward one another, the sections 12 and 14 would automatically further break or articulate upwardly and toward one another. Downward breaking or jointing would not be possible in such an embodiment as the maximum distance between the two end columns would still ensure a slight upward break or hinge between the sections 12 and 14. Such an embodiment would be acceptable for use because patient holding pads could be positioned on the frames 12 and 14 such that the patient would be in a substantially horizontal position even when there is a slight upward bend or break at the hinge between the sections 12 and 14.

Returning to the hinge 70 of illustrated embodiment, the inner member 78 is slidingly and rotatably receivable in an interior 84 of the outer member 76. The outer member has a pair of pivot apertures 86 and the inner member has a pivot aperture 87, the apertures cooperating to create a through bore for receiving a pivot pin 88, preferably radiolucent, through both the inner and outer hinge members. The interior 84 includes a curved partially cylindrical surface 89 for slidingly receiving a cooperating outer rounded and partially cylindrical surface 90 of the inner member 78. The inner member 78 further includes a downward breaking stop or projection 92 that limits a downward pivot (in a direction toward the cables 20) of the hinge 70 in the event the cables 20 should fail. The stop 92 abuts against a surface 93 of the interior 84. In the illustrated embodiment, the stop 92 limits the extent of rotation or hinging of the section 66 with respect to the section 66' to about twenty-five degrees. Upward pivot (in a direction away from the cables 20) is limited by abutment of an inner planar surface 95 with a planar surface 96 of the hinge inner member 78.

With particular reference to FIG. 8, the hinge mechanism 72 is substantially a mirror image of the hinge mechanism 70 and therefore includes the following elements: a hinge outer member 76', an inner member 78', an extension 80' with a groove 82', an interior 84', pivot apertures 86', a pivot pin 88', a curved surface 89' (not shown), an outer surface 90' (not shown), a stop 92' (not shown), an abutment surface 93', an inner planar surface 95' and a planar surface 96' that are identical or substantially similar in shape and function to the respective hinge outer member 76, inner member 78, extension 80, groove 82, interior 84, pivot apertures 86, pivot pin 88, curved surface 89, outer surface 90, stop 92, abutment surface 93, inner planar surface 95 and planar surface 96 described herein with respect to the hinge 70.

It is noted that other hinge or pivot mechanisms may be utilized in lieu of the hinge assembly 16. For example, the polyaxial joint 95 illustrated and described in Applicant's U.S. Pat. No. 7,152,261 and pending U.S. patent application Ser. No. 11/159,494 filed Jun. 23, 2005, may be incorporated into the patient support structure 10 at the break or joint between the sections 12 and 14. The disclosures of U.S. Pat. No. 7,152,261 and U.S. patent application Ser. No. 11/159,494 are incorporated by reference herein. It is foreseen that a rotating universal joint operated type of hinge mechanism could be used with the invention, and the like. While a lead screw drive could also be utilized, a more radiolucent joint or hinge is preferred.

Figure 12:
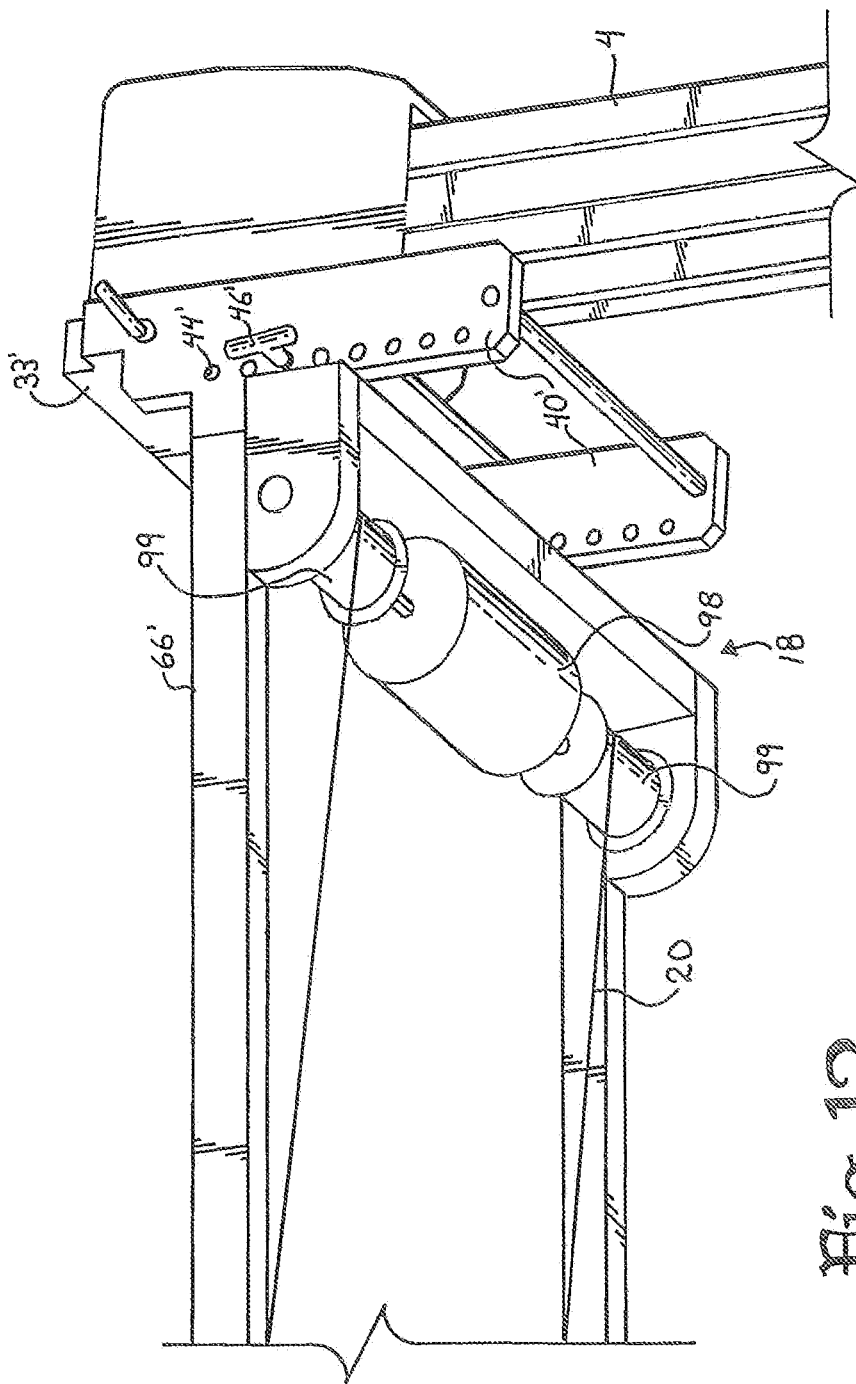
FIG. 12 is an enlarged and partial perspective view of a portion of the structure of FIG. 1 showing an actuator in the form of a cable drive motor and winch cylinders.

With particular reference to FIGS. 6 and 12, the cable drive system 18 includes a rotary motor 98 cooperating with and driving by rotation a pair of winch cylinders 99 disposed on either side of the motor 98. The motor 98 and cylinders 99 are mounted to the end connector 58' located near the support column 4. Each cable 20 is attached to one of the winch cylinders 99 at one end thereof and to the end connector 58 at the other end thereof. In a first longitudinal position wherein the section 12 is substantially planar with the section 14, the cables 20 are wound about the winch cylinders 99 an amount to provide enough tension in the cables 20 to maintain such a substantially planar orientation and configuration, with the hinge extensions 82 and 82' being in contact with each of the cables 20. The motor 98 is preferably low speed and high torque for safely winding both of the cables 20 simultaneously about the cylinders 99 to draw the section 12 toward the section 14 to result in an upward breaking or jointing configuration with the hinges 70 and 72 disposed in spaced relation with the cables 20 and the hinges 70 and 72. The motor 98 may be reversed, reversing the direction of rotation of the winch cylinders 99 for slowly unwinding the cables 20 to a downward breaking or jointing configuration. As the cables 20 unwind, gravity draws the support sections 12 and 14 downward with the cables 20 being received in the grooves 82 and 82' of the hinge extensions 80 and 80'. As the cables 20 slacken, the hinges 70 and 72 continue to lower pressing down upon the cables 20. Again, different ways to move the hinges are foreseen both directly and indirection with actuators that are more or less load-bearing.

It is noted that the frame sections 12 and 14 are typically equipped with pads (not shown) or other patient holding structure, as illustrated, for example, in Applicant's U.S. Pat. No. 5,131,106, the disclosure of which is incorporated by reference herein. It is foreseen that such patient holding structure could translate or glide along the frame sections 12 and 14 and be radiolucent. Furthermore, with respect to FIGS. 13 and 14, the frame member sections 66 and 68 of section 12 and the frame member sections 66' and 68' of the section 14 may be replaced with substantially rectangular radiolucent imaging tops or sections 100 and 101' respectively. Each of the sections 100 and 101' having elongate slots 101 formed therein to allow for attachment of the hinge mechanisms 70 and 72 in a manner identical or substantially similar to what has been described herein with respect to the frame sections 12 and 14.

With reference to FIGS. 15-17, the imaging sections 100 and 100' are illustrated, replacing the frame sections 12 and 14 of the embodiment disclosed in FIGS. 1-12. Each of FIGS. 15-17 represent configurations in which the cable drive 18 is tensioned such that the sections 100 and 100' are kept in a substantially coplanar configuration. FIG. 15 illustrates a configuration in which the column 3 is elevated upwardly with the frame sections hinging at the support assemblies 5 and 6, resulting in an inclined position or configuration of the entire patient support. In the illustrated embodiment, the section 100 would preferably receive a patient's head. Therefore, FIG. 15 illustrates a reverse Trendelenburg position or orientation. FIG. 16 illustrates the sections 100 and 100' again in a substantially common plane with both sections being rotated to a tilted position produced by a powered rotation of the sub assemblies 26 and passive rotation of the assembly 26' with both columns 3 and 4 otherwise holding the sections 100 and 100' at the same height. FIG. 17 illustrates both tilting due to rotation of the assemblies 26 and 26' and also a sloping or inclined position with the column 4 being extended vertically. Thus, FIG. 17 illustrates a Trendelenburg position or orientation with both the sections 100 and 100' remaining in substantially the same plane. It is foreseen that a bearing block assembly at one or both ends of the table could provide for some lateral or transverse translation along with horizontal translation to prevent binding of the hinge mechanisms.

Figure 18:
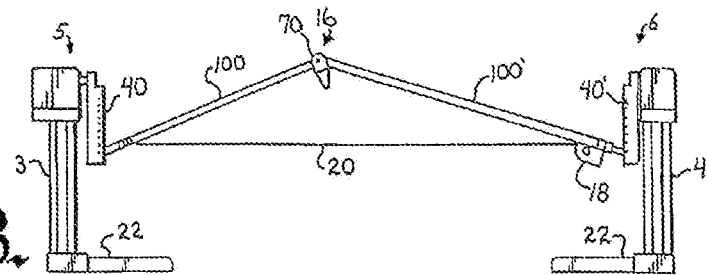
FIG. 18 is a side elevational view of the structure of FIG. 15 shown in a symmetrical upward breaking position.
Figure 19:
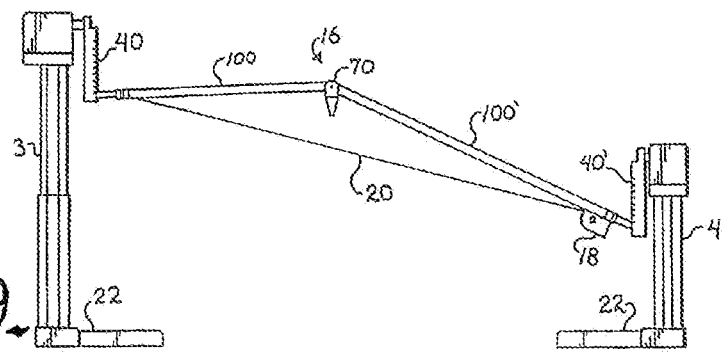
FIG. 19 is a side elevational view of the structure of FIG. 15 shown in a first inclined and upward breaking position.
Figure 20:
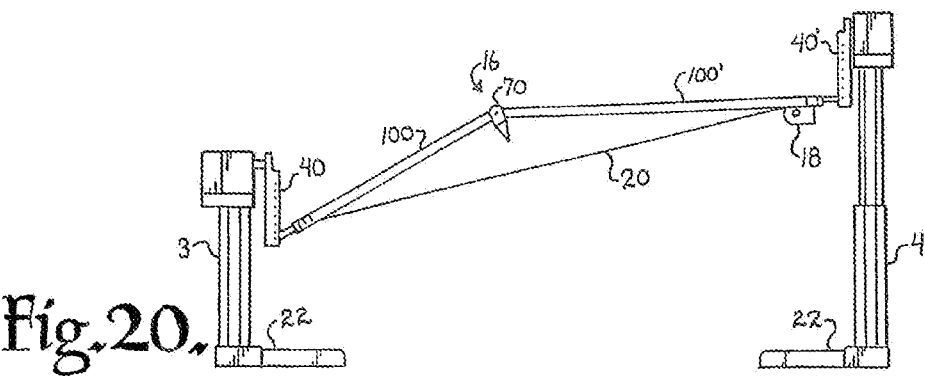
FIG. 20 is a side elevational view of the structure of FIG. 15 shown in a second inclined and upward breaking position.

With reference to FIGS. 18-20, there is illustrated three upward breaking or hinging configurations of the structure 1. FIG. 18 illustrates a symmetrical upward breaking configuration wherein the columns 3 and 4 and their respective support connection assemblies 5 and 6 are holding the patient support structure at substantially the same height with the cables 20 being shortened by rotation of the winch motor to result in an upward break or joint in the hinge assembly 16. FIG. 19 illustrates the column 3 being extended to a maximum height and the cables reeled to shorten a distance between the sections 100 and 100'. An example of such an upward break or joint with reverse Trendelenburg would be a head or column 3 height of 43 inches, a foot or column 4 height of 24 inches and a 35 degree upward break with zero degree roll. FIG. 20 illustrates an upward breaking Trendelenburg with the column 4 being extended to a maximum height.

With reference to FIGS. 21-23, there is illustrated three downward breaking configurations of the structure 1. FIG. 21 illustrates a symmetrical downward breaking configuration wherein the columns 3 and 4 are holding the outer ends of the patient support structure, at the same height with the cables 20 being unwound or slackened to result in a downward break or joint in the hinge assembly 16, the hinges 70 and 72 contacting the cables 20. FIG. 22 illustrates a downward breaking reverse Trendelenburg with the column 3 being extended to a maximum height resulting in a patent's head end being at a maximum height. FIG. 23 illustrates a downward breaking Trendelenburg with the column 4 being extended to a maximum height.

It is noted that in each of the configurations illustrated in FIGS. 18-23, the sub-assemblies 26 may be rotated in either direction, resulting in a tilted or rotated as well as upwardly or downwardly broken or hinged configuration. For example, FIG. 24 illustrates the structure 1 with support frame sections 12 and 14 positioned in a configuration similar to that illustrated in FIG. 19, but also including rotation, resulting in a tilting and upwardly breaking or jointed configuration of the structure 1. An example of the position illustrated in FIG. 24 would be: a head or column 3 height of 41 inches, a foot or column 4 height of 34 inches and a 35 degree upward break or joint with 10 degree roll. Such positioning capabilities is associated with translation compensation occurring at both outer ends of the breaking patient support structure.

With reference to FIGS. 25-29, another structure, generally 102 according to the invention is illustrated. The structure 102 utilizes all of the elements described herein with respect to the structure 1 and therefore the same references numerals are used for the same elements or features. The structure 102 differs from the structure 1 in that the H-bar posts 40 and 40' are replaced or modified to be extended H-bar posts 40A and 40A', allowing for the mounting of two elongate structure 10 and cooperating cable drives 18 or other actuators to move the hinges. In the embodiment shown in FIG. 25, one of the structures 10 includes the frame member 12 and 14 while the other structure is an imaging top having sections 100 and 100'. As previously described herein, the cooperating H-bar posts 40A and 40A' equipped with a plurality of apertures allows for the placement of the support structures 10 at a variety of locations. For example, FIGS. 25-28 illustrate a first spaced orientation of the elongate frame with respect to the elongate imaging top with the imaging top located at a "lower" position identified by the reference letter L. The identical components are shown in FIG. 29 with the imaging top located at a "mid-position" identified by the reference letter M, illustrating a more compact or closely spaced orientation of the elongate frame with respect to the elongate imaging top than what is shown in FIG. 25.

As illustrated in FIGS. 25-28, the structure 102 provides for the complete rotation and thus a roll-over of a patient by actuation of the motor of the rotation subassembly 26 using the controller 29. The structure 102 shown in FIGS. 25-29 is further illustrated with a base support 110 fixed to each of the columns 3 and 4 and rollers or castors 112 at the base of the structure 102.

With reference to FIGS. 30 and 31, further embodiments according to the invention, generally 200 is illustrated. The system 200 broadly includes an elongate length-adjustable base 202 surmounted at either end by respective first and second upright support piers or columns 203 and 204 which are connected to respective first and second support connection assemblies, generally 205 and 206 that translate, rotate, and angulate or pivot. Between them, the support assemblies 205 and 206 uphold an elongated breaking, hingeable or pivotable patient support structure, generally 210. The hinge structure is described in detail in Applicants's U.S. Pat. No. 7,152,261 and also U.S. patent application Ser. No. 11/159,494, both disclosures of which are incorporated by reference herein. In this embodiment, the inward articulations remain mostly unloaded and translation compensation can occur at both outer ends of the patient support structure. The embodiment 200A illustrated in FIG. 31 differs from the structure 200 only in that the length-adjustable base 202 is replaced by a first base 220 attached to the pier 203 and a second base 222 attached to the pier 204. All of the bases 202, 220 and 222 include castors or rollers 230 or some other movable structure to allow the piers 203 and 204 to move toward and away from one another during upward or downward breaking of the structure 210. In this embodiment, it is foreseen that actuators would provide rotation, angulation and horizontal translation at both outer ends of the patient support structure.

It is foreseen that cable drives, as described herein, other types of motor drives, including screw drives with gears, universal joints, hydraulic systems, and other like actuators, may be utilized to facilitate both upward and downward breaking of the support structure 210.

Another patient support structure according to the invention, generally 301, is illustrated in FIGS. 32-34, again, providing translation compensation on both outer ends. The structure 301 generally includes a translating actuator on one end known in the prior table art as an inclinable and transversely and horizontally translatable operating table support structure 304, a vertically height adjustable end support or pier 306 and a hinged or pivotally upwardly and downwardly breaking or jointing support structure 310 connected to both the structure 304 and the pier 306 by pivoting translation compensation mechanisms. The patient support structure 310 further includes a first actively angulated section 312 moved by an actuator and a second section 314. The first section 312 is fixed to and extends from the operating table support 304. The second section is attached to the pier 306 by a pivoting translation connector assembly 320, such as the support connection assembly 5 described herein with respect to the structure 1. The hinge mechanism 316 disposed between the support sections 312 and 314 may be a conventional hinge, pivot, or pivot or hinge systems previously described herein. Preferably, it is a simple hinge and does not need to carry much load.

In use, the operating table support 304 utilizes electric or other power means to move the support section 312 up and down at an incline and to translate it transversely and longitudinally, as is known in the art. The operating table support 304 can also tilt or rotate from side to side. In response to the movement of the section 312, the section 314 also moves, resulting in upward and downward breaking illustrated in FIGS. 33 and 34. In response to the movement of the section 312, the connection 320 provides translation compensation horizontally along with rotation and angulation degrees of freedom of movement. The pier 306 includes a motor for raising and lowering the pier at the connection 320. It is foreseen that the connection 320 could have actuators for rotation, angulation and translation.

As stated above with respect to other embodiments of the invention described herein, it is foreseen that cable drives as described herein, other types of drives including screw drives, gear mechanisms, hydraulic systems, and other actuator like mechanisms, may be utilized to facilitate both upward and downward breaking of the support structure 310 at the joint 316.

With reference to FIGS. 35-47, another patient support structure according to the invention, generally 401 includes first and second upright support piers or columns 403 and 404 that are connected to one another by a base support 402. In some embodiments according to the invention, each column may be surmounted on an independent movable or stationary base. The column 403 is connected to a first support assembly, generally 405 and the column 404 is connected to a second support assembly, generally 406. Between them, the support assemblies 405 and 406 uphold at least one removable elongate and articulate, substantially centrally jointed or breaking patent holding or support structure, generally 410. The assembly includes a first frame section 412, a second frame section 414 and a pair of identical hinge assemblies, generally 416, disposed between and connecting the first and second frame sections 412 and 414. In the illustrated embodiment, the first frame section 412 for holding a head and upper body of a patient is of a slightly shorter longitudinal length (along an axis X) than the second frame section 414. Therefore, the spaced hinge assemblies 416 are approximately centrally located relative to a body of a patient being placed on the structure 410. In the illustrated embodiment, the hinge assembly further includes a drive system that includes a pull rod assembly, generally 418, and cooperating spaced slider bars 420. Again, other drive systems are foreseen, especially lead screws, chains and other linkages.

The columns 403 and 404 are substantially similar in form and function to the columns 3 and 4 previously described herein with respect to the structure 1. The columns 403 and 404 are supported by outwardly extending feet 422 that include casters that may be equipped with a floor-lock foot lever for lowering the feet 422 into a floor-engaging position. The columns 403 and 404 each include two or more lift arm segments respectively that permit the height of each of the columns 403 and 404 to be selectively increased and decreased in order to raise and lower all or a selected portion of the connected patient support structure 410.

Each of the support connection assemblies 405 and 406 generally includes a rotation subassembly 426 and 426' and an angulation subassembly 427 and 427', respectively, that are the same or substantially similar to the subassemblies 26, 26', 27 and 27' previously described herein with respect to the structure 1. In the illustrated embodiment, the angulation subassembly 427 connected to the frame 412 for holding the head and upper body of a patient is shown as substantially identical to the subassembly 27 and, therefore, shall not be described further herein. The subassembly 427' is substantially similar to the subassembly 27', but with some modifications, including a frame 436 disposed transverse to the overall longitudinal axis X of the structure 401, the frame 436 providing for slidable support of the pair of identical slider bars 420 that are disposed at either side of the frame 414 and near the subassembly 427'.

Similar to the rotation subassembly 26 previously described herein, the rotation subassembly or mechanism 426, includes at least one motor housing 430 surmounting the support column 403. It is foreseen that a cooperating motor may also be mounted on the support column 404. A main rotational shaft 432 extends from the motor housing 430 that turns a rotation structure or bar that in turn is connected to and rotates the patient support 410 about a longitudinal axis. In particular, the motor housing 430 contains a rotary electric motor or other actuator drivingly engaged with the shaft 432. The rotation mechanism 426 is operated by actuating the motor using a switch or other similar means. The shaft 432 rotationally cooperates with a pair of substantially vertically disposed translation posts or H-bar posts 440, the posts 440 being attached to and disposed at either end of the transverse rotation structure or bar 433. Each H-bar post 440 includes a plurality of apertures 444, allowing for selective, hinged vertical placement of the frame section 412 identical or substantially similar to what has been described previously herein with respect to the H-bar posts 40, the angulation sub-assembly 27 and the frame end section 58 of the frame section 12 previously described herein with respect to the structure 1.

With particular reference to FIGS. 38-40, as stated above, the sub-assembly 426' is substantially similar to the sub-assembly 426 and therefore may include a motor and further includes either an active or passive rotational shaft 432' that engages a rotation structure or bar 433' that is attached to a pair of substantially vertically disposed H-bar posts 440'. A plurality of cooperating apertures 444' formed in the posts 440' provide passageway for a pivot pin 446 to extend therethrough. The pivot pin 446 is receivable in each cooperating pair of apertures 444', allowing for selective placement of a translation connector 448, 452 component that is part of the connection assembly. In this embodiment, the translation connector is sized and shaped to be received between the pair of posts 440' and also receive the pivot pin 446 therethrough. The pin 446 and connector 448 are thus positionable in an orientation transverse to the longitudinal axis X of the patient support frame 410 at a variety of heights to be selected by the surgeon and readily changeable, even during surgery if necessary, to vary the height of the frame section 414. The multiple location or height feature is also advantageous when more than one frame or patent structure is mounted in tandem, for example, when both a frame and imaging table are used together, such as is shown in the embodiment illustrated in FIGS. 25-29. The position of the frame or other structure may be desirably changed to provide close proximity to an imaging top with a distance between a patient support and an imaging top being expandable or reduceable depending upon the size or other attributes of a patient and surgical or other requirements. The connector 448 has a slot for translatably receiving the pivot pin 446. It is noted that the H-bar support 440', apertures 444', elongate transverse pin 446 and translation connector 448, 452 component are the same or substantially similar in form and function with the respective support 40, apertures 44, transverse pin 46 and translation connector 48 previously described herein with respect to the structure 1.

The translation connector 448, again, has an attached pivot connector 452 that is substantially similar to the pivot connector 52 previously described herein, with the exception that rather than being attached directly to an end piece or section of the patient support frame 414, the pivot connector 452 is fixed to the frame 436 that is fixed to and supports the slider bars 420 near end surfaces 464 thereof. Thus, the slider bars 420 are in a hinged relationship with the H-bar supports 440'. The slider bars 420 are also in slidable relation with the frame section 414 while being securely attached thereto and disposed substantially parallel to a longitudinal axis of the section 414, as will be described in greater detail below. Such slidable attachment facilitates upward and downward breaking or hinging of the section 414 with respect to the section 412 at the hinge mechanism 416. Also as more fully described below, the pull rod assembly 418, that is connected to both the frame section 414 and the hinge mechanism 416, is rotatable so as to control the hinge or break angle of the patient support 410 and render the support 410 rigid at a desired upward or downward break or joint of the hinge mechanism 416.

With particular reference to FIGS. 38 and 39, the support frame section 414 includes opposed elongate and parallel frame sections 466 and 468 attached to one another by a transverse end frame section 469. A support plate 470 is attached to and is disposed below each of the sections 466, 468 and 469 to provide additional support and stability to the frame section 414 at and near the end section 469. Further support is provided by a pair of frame support plates 471, both of which are fixed to the end support frame section 469 near one end thereof; one plate 471 being fixed to the section 466 and the other plate 471 being fixed to the section 468. At least one pair of slider bar holding structures 472 are fixed to the support plate 470 and extend downwardly therefrom at each of the frame sections 466 and 468. Each structure 472 includes a through bore that extends parallel to the frame sections 466 and 468, the structure 472 for slidably receiving one of the slider bars 420 directly below one of the frame sections 466 and 468 and also orienting the pair of slider bars 420 in a direction substantially parallel to the frame sections 466 and 468. The illustrated slider bar holding structures 472 are spaced from the end frame section 469 and located near a forward edge 473 of the plate 470. In the illustrated embodiment, the holding structures 472 are also bolted to the frame sections 466 or 468. A pair of pull-rod supports 475 are also fixed to the support plate 470 and the frame 414 and extend downwardly therefrom at each of the frame sections 466 and 468 and also downwardly from the end frame section 469. Each structure 475 includes a through bore for receiving a transverse pivot pin or bar 476 mounted below the slider bars 420. The pull-rod assembly 418 is attached to the support 475 at the pivot pin 476 and is thus in hinged relationship with the support 475, pivotally attached thereto at end portions 478.

The actuator assembly 418 further includes a pair of housings 480, each housing attached to an end portion 478 and having a powered actuator 482 cooperating with one of a pair of rotatable extendible and retractable rods 484 and a pair of hinge connectors 486, each pivotally attached to a respective cam plate 488 of the respective hinge mechanism 416 at a respective pivot pin 490. The cam plate 488 has a substantially centrally located curvilinear wall 489 forming a curvate aperture or slot, a lower circular aperture for receiving the pin 490 and an upper circular aperture for receiving a pin 502, described in greater detail below. Each pull rod 484 is rotatably mounted within one of the housings 480, such rotation being controlled by operation of the actuator 482 located in the housing 480 and engaged with the rod 484 to screw and thus selectively move or draw the rod 484 into or away from the hinge mechanism 416 in a direction along a longitudinal axis of the rod 484, that in turn results in breaking or jointing of the patient support 410 at the hinge mechanism 416. It is foreseen that other embodiments according to the invention may utilize other types of push/pull rods or actuator mechanisms, including, for example hydraulic systems and actuators that can provide angulation. An additional centrally located pull-rod or piston may be included to provide additional support. Furthermore, other hinge mechanisms according to the invention may be utilized in lieu of the mechanism 416, for example including, but not limited to, polyaxial joints, roller with spokes, sprockets, toothed gears, universal axis gears, or the like.

With particular reference to FIG. 41, the illustrated pair of hinge mechanisms 416, each having a cam plate 488, further include a pair of forked arms 492 extending from the frame section 412 and a pair of cooperating forked arms 494 attached to and extending from the section 414. Hinge arms 496, 497, 498 and 499 having apertures near opposite ends thereof for receiving pivot pins cooperate with the respective cam plate 488 and adjacent forked arms 492 and 494 at pivot pins 501, 502, 503 and 504. All of the pivot pins 490, 501, 502, 503 and 504 are disposed transverse to the longitudinal axis X of the patient support structure 401. In particular, the pivot pin 501 is received by circular apertures located near first ends of the hinge arms 496 and 498 and a circular aperture in the arm 492, thus pivotally attaching the arm 492 with both the hinge arms 496 and 498. The pivot pin 502 is received by an upper circular aperture in the cam plate 488 and circular apertures located near the ends of each of the forked arms 492 and 494, thus pivotally attaching the cam plate 488 with both of the forked arms 492 and 494. The pivot pin 503 is received by circular apertures located near first ends of the hinge arms 497 and 499 and a circular aperture in the arm 494, thus pivotally attaching the arm 494 with both the hinge arms 497 and 499. The pivot pin 504 is received by the slot 489 and also by circular apertures located near second ends of the hinge arms 496, 497, 498 and 499, thus pivotally attaching all four hinge arms 496, 497, 498 and 499 with the cam plate 488 at the slot 489.

Also, with particular reference to FIGS. 35 and 38-41, the structure 401 is shown in a neutral, planar orientation, with the pull-rod assembly 418 holding the hinge mechanism 416 in such neutral position, with the forked arms 492 and 494 in parallel. In such position, the pin 504 is located at or near a rear-ward end of the slot 489.

Figure 42:
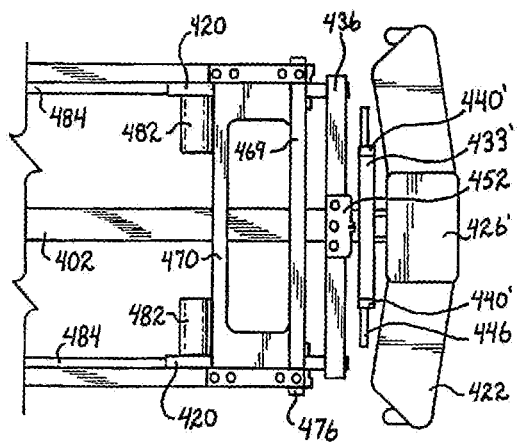
FIG. 42 is an enlarged and partial top plan view of a portion of the structure of FIG. 35 and shown in the same position as shown in FIG. 36.
Figure 44:
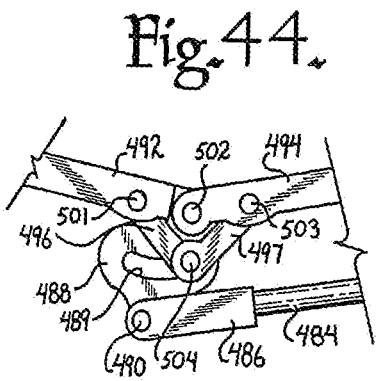
FIG. 44 is an enlarged and partial side elevational view of the structure of FIG. 35 and shown in the same position as shown in FIG. 36.
Figure 43:
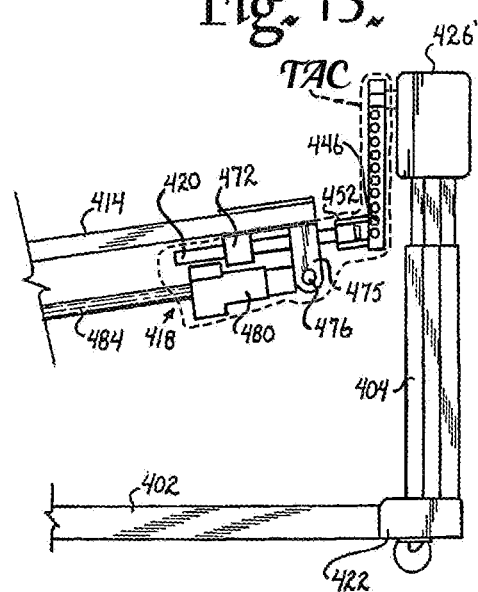
FIG. 43 is an enlarged and partial side elevational view of the structure of FIG. 35 and shown in the same position as shown in FIG. 36.
Figure 48:
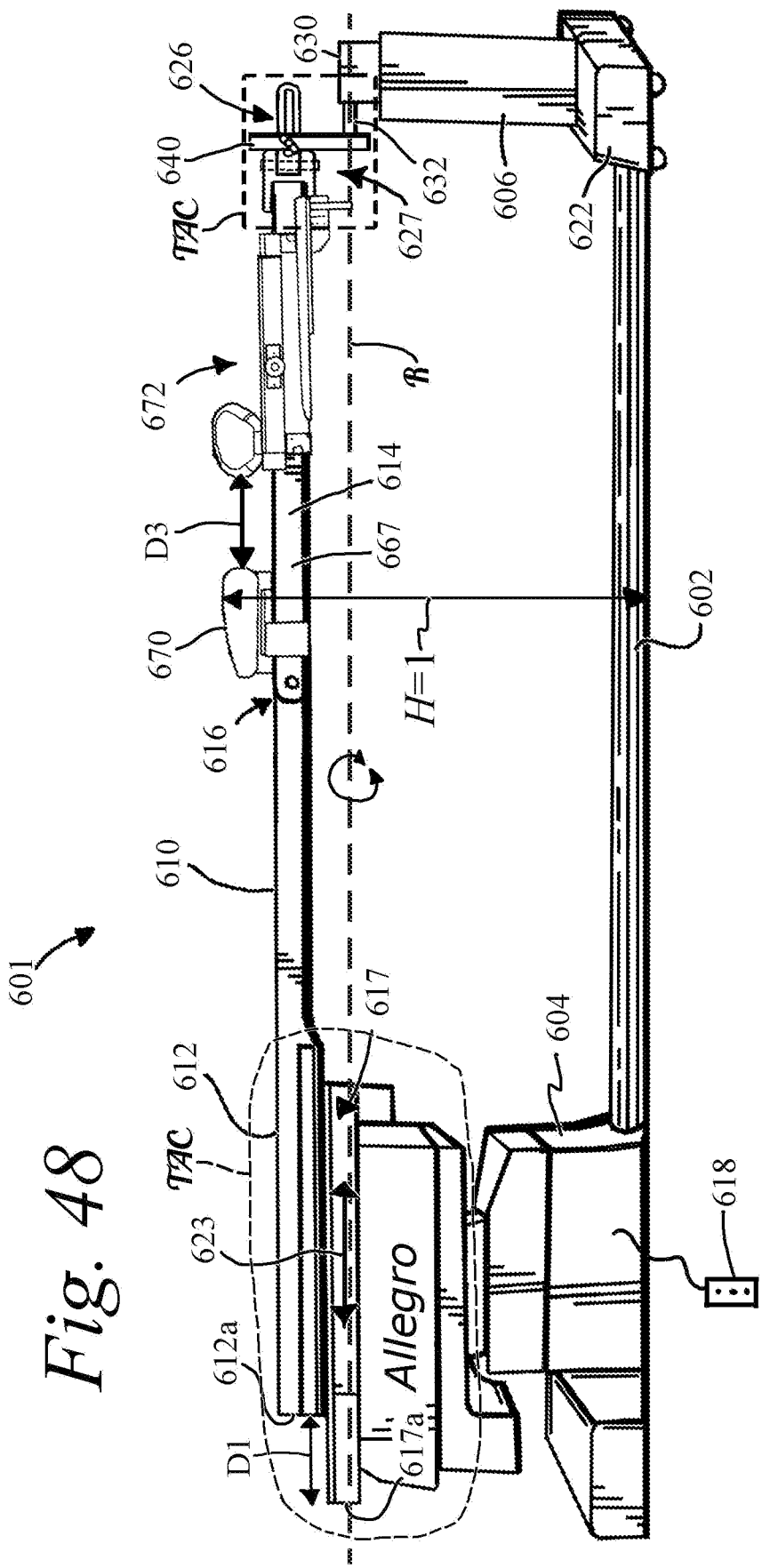
FIG. 48 is a side view of an eighth embodiment, similar to that of FIGS. 32-34, of a patient support structure, again, with translation compensation on both outer ends thereof, according to the invention, shown in a planar horizontal position, and including reversibly attached stationary upper body support assembly and hip-thigh pad structures.
Figure 49:
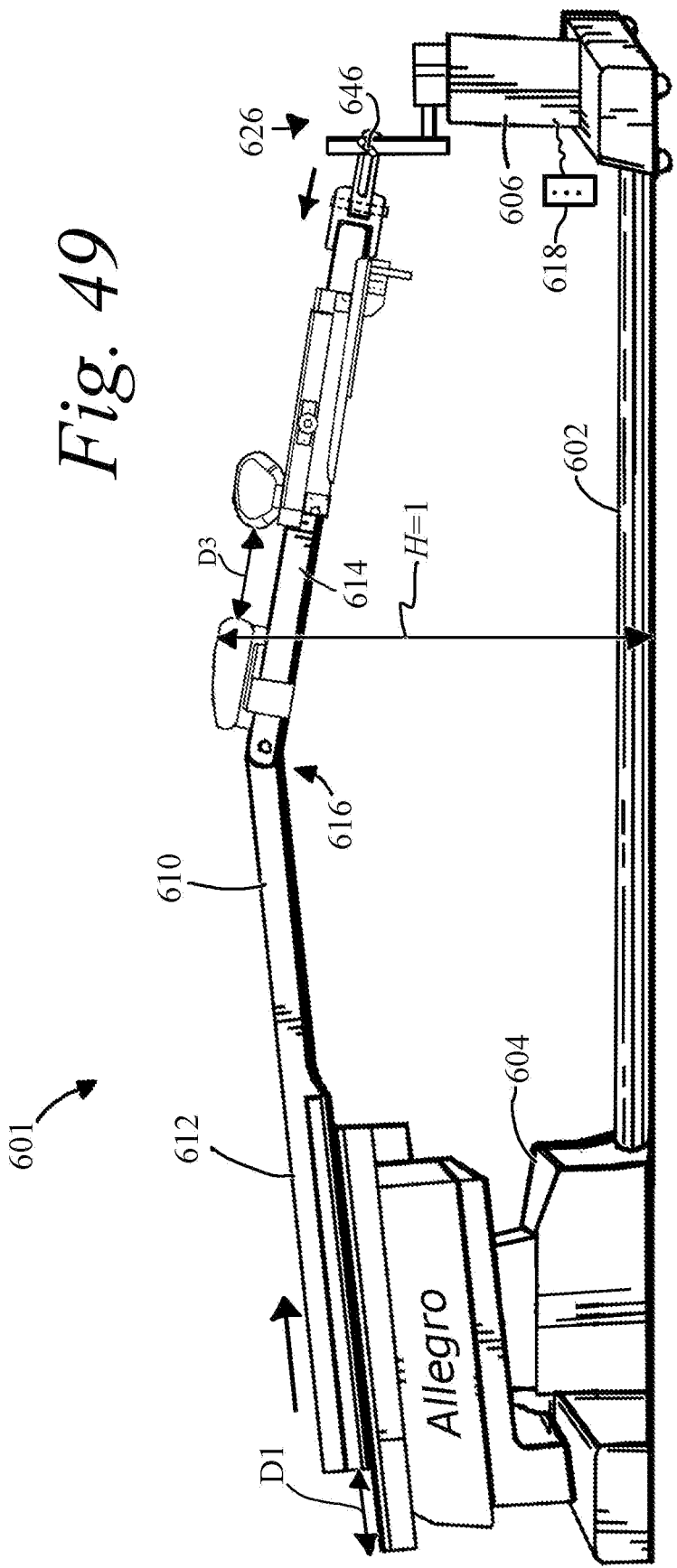
FIG. 49 is a side view of the structure of FIG. 48 shown in an inclined and upward breaking position, and including reversibly attached upper body support and hip-thigh pad structures of FIG. 48.
Figure 50:
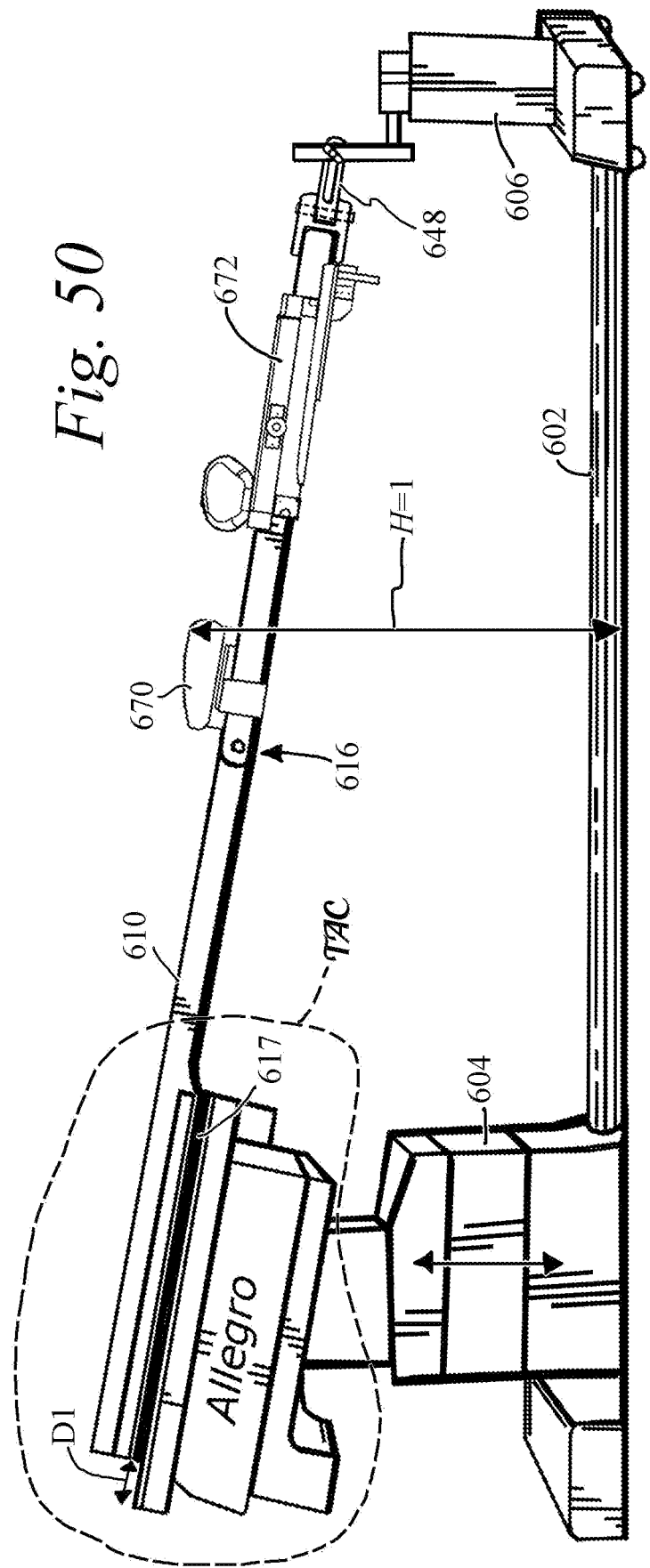
FIG. 50 is a side view of the structure of FIG. 48 shown in a Trendelenburg position, and including reversibly attached chest support and hip-thigh pad structures of FIG. 48.
Figure 51:
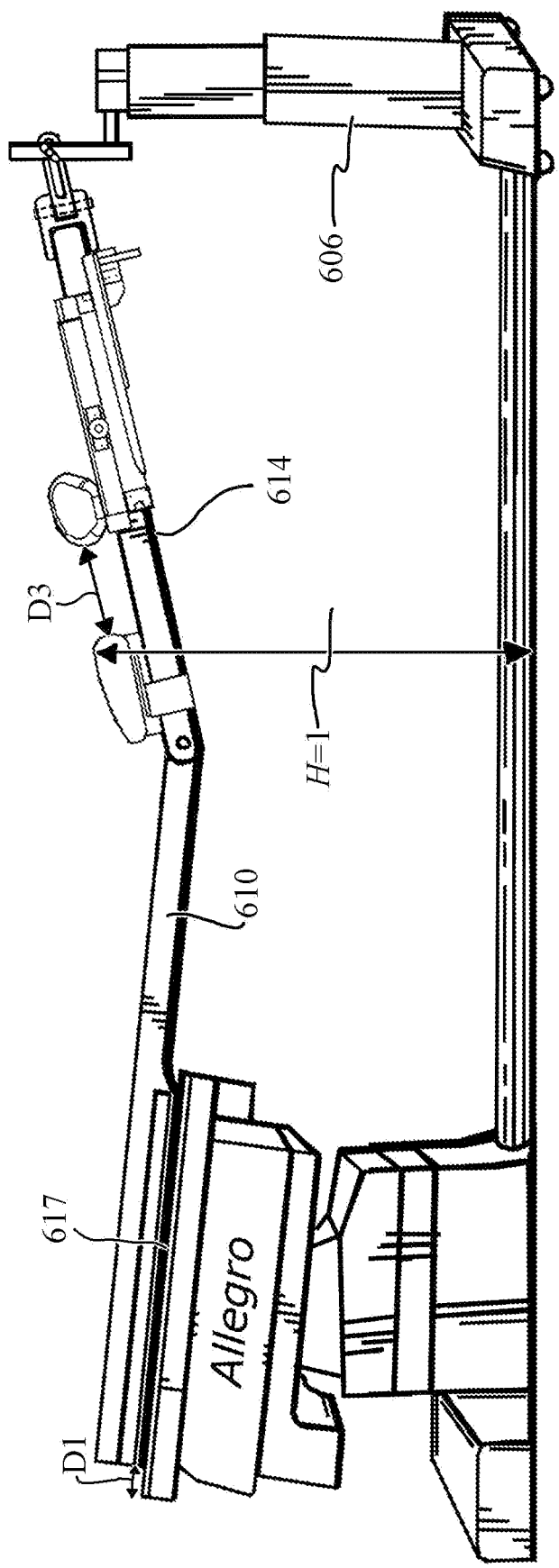
FIG. 51 is a side view of the structure of FIG. 48 shown in a downwardly breaking position, and including reversibly attached chest support and hip-thigh pad structures of FIG. 48.
Figure 52:
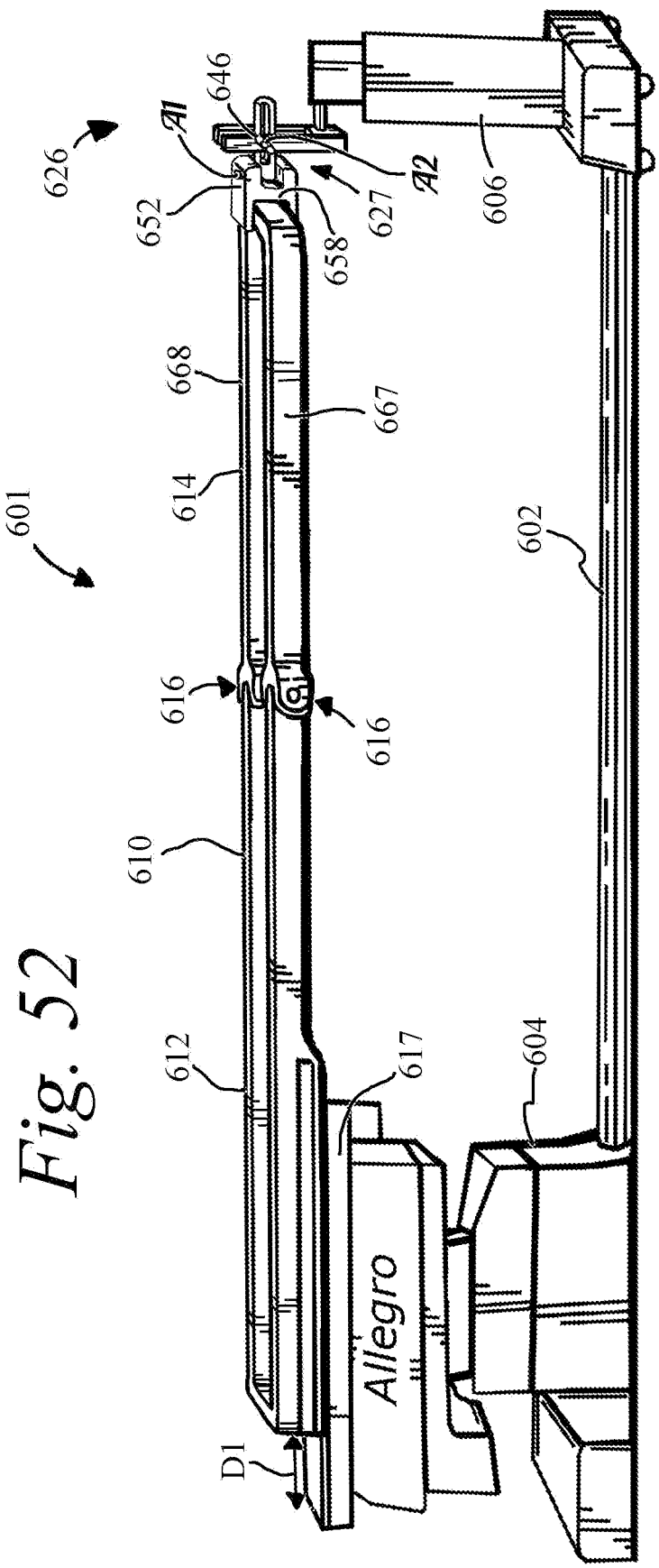
FIG. 52 is a side view of the structure of FIG. 48 showing the patient support structure and inward articulation in a horizontal and tilted position, and with the reversibly attached chest support assembly and hip-thigh pad structures of FIG. 48 removed.

With reference to FIGS. 42-44, as the rod 484 is rotated to selectively move the hinge mechanism, the pin 504 remains near the rear-ward end of the slot 489 and the action of the rod causes the hinge mechanism 416 to pivot the cam plate 488 at the pivot pin 490, causing the arms 492 and 494 to move toward the rod hinge connector 486 and thus pivot the patient support at the pin 502, causing a downward break or joint in the patient support 410. With reference to FIGS. 45-47, as the rod 484 is rotated to selectively shorten the length thereof, the support portion 414 slides along the slider bars 420 away from the end support 404. At the same time, the pin 504 slides along the slot 489 to an opposite or forward end thereof as the cam plate pivots in a forward direction about the pin 490. The movement of the rod 484 thus causes an upward break at the pivot pin 502. In the illustrated embodiment, the patient frame is pinned at the head end, but is free to move along the fixed slider bar 420 at the foot end, providing dynamic support to the patient frame. The slider bar mechanism can be attached to a bearing block mechanism to provide lateral or transverse translation movement, as described previously. The sidebar is configured to provide for a considerable amount of translation which is required for this type of breaking table.

It is noted that since the patient frame is free to move over the slider bar, a horizontal force component is generated by the combined components of the patient support. When the support is broken or jointed upward, the angle of the foot end frame imparts a horizontal force on the slider that urges the end supports 403 and 404 toward one another. When the table is broken downward, a horizontal force develops that tends to push the end supports apart. It has been found that the magnitude of the horizontal force is a function of support loading and break angle, and thus, for example, if a working limit of five hundred pounds is selected for the patient support, a worst case of horizontal loading is only about fifty-eight pounds at an upward break or joint of thirty-five degrees. It is noted that the illustrated structure 401 advantageously supports a breaking or jointing range from about thirty-five degrees up to about twenty degrees down. Throughout such range, the horizontal forces imposed by the structure are minimized by the illustrated locked support frame that moves on a slider bar at the foot end of the support. This provides a significant improvement to the prior art.

As with the structure 1 configurations illustrated in FIGS. 18-23, the upward and downward breaking of the patient support 410 may be modified by placing the portions 412 and 414 at different vertical locations along the H-bar supports 440 and 440', thus resulting in symmetrical or asymmetrical breaking configurations. Furthermore, the portions 412 and 414 may be rotated or tilted as described above with respect to the structure 1.

With reference to FIGS. 48-54, another patient support structure according to the invention, generally 601, includes a floor mounted base 602, a conventional or standard vertically adjustable, and inclinable operating table support structure 604 known in the industry, a vertically height adjustable end support, pier or column 606 and a hinged or pivotally upwardly and downwardly breaking or jointing patient support structure 610 connected to both the table support structure 604 and the pier 606 with pivoting translation compensation capabilities. The patient support structure 610 further includes a first frame section 612 and a second frame section 614 joined together by a pair of upwardly and downwardly breaking hinges 616. An intervening second base, longitudinal translation subassembly or longitudinal translation connector 617 surmounts the operating table support 604. The first frame section 612 is engaged by, fixed or attached to the second base 617 such that the first frame section 612 extends outwardly from the operating table support 604 and toward the pier 606. The table support structure 604 includes a powered mechanism, electronics and a controller 618 for selectively adjusting the height, inclination and tilt or roll of the patient support structure 610. The second base 617 includes a motor (not shown), electronics (not shown) and structure that slidingly moves or longitudinally translates the first frame section 612 with respect to the operating table support 604.

The second base 617 slidingly moves, or translates in a longitudinal direction, the first frame 612 a distance D1 toward or away from the pier 606, as is indicated by the arrow 623. The distance D1 is measurable from the rear or outer end 617a of the second base 617 and the rear or outer end 612a of the first frame section 612. Longitudinal translation, or longitudinal movement or sliding, of the first frame section 612, such as with respect to the operating table support 604, and resultant changes or variation in D1, is coordinated and synchronized by a controller with changes in the angulation of the hinges 616, at the table support 604 and at the pier 606, so as to position the patient support 610 in various positions determined by the surgeon, such as is described elsewhere herein. In this embodiment, the hinges 616 themselves need not carry much load.

The pier or support column 606 includes a rotation subassembly, generally 626, and an angulation subassembly, generally 627, that are interconnected and include an associated power source and circuitry linked to a controller, such as but not limited to controller 618, for cooperative and integrated actuation and operation. The rotation subassembly 626, an angulation subassembly 627 and pivoting translation subassembly are the same or substantially similar to the rotation subassembly 26', the angulation subassembly 27', and the translation connector 48, 52 in FIGS. 4 and 5, respectively. The rotational subassembly 626 enables coordinated rotation or tilting of the patient support structure 610 about the longitudinal axis of the structure 601. The angulation subassembly 627 enables the selective hinging, articulation or breaking of the patient support 610 at the hinge assemblies 616 at desired levels and increments as well as selective tilting of the frame portions 612, 614 with respect to a longitudinal axis of such frame portion.

The rotation subassembly or mechanism 626, shown in FIGS. 48-54, includes at least one motor housing 630 surmounting the pier 606. A main rotational shaft 632 (most easily seen in FIG. 55) extends from the motor housing 630 that turns a rotation structure 633. The rotation structure 633 in turn rotates the connected patient support 610 about a longitudinal axis. The motor housing 630 contains a rotary electric motor or other actuator drivingly or actively engaged with the shaft 632. The rotation mechanism 626 is operated by actuating the motor using a switch or other similar means, such as but not limited to controller 618, such as is known in the art. The rotation structure 633 is fixed to the shaft 632 at a location spaced from the motor housing 630 and the pier 606 to provide clearance for rotation of the connected patient support structure 610. In some embodiments, the rotation subassembly 626 can be passive and, therefore, not include a motor. However, the support pier 606 preferably includes a powered mechanism to provide selective height adjustment of the assembly 626. The rotation subassembly can be at different locations between the end support of the base and the outer end of the patient support structure.

In the embodiment shown, the rotation structure 633 is attached to an H-frame bracket 640. The translation connector subassembly is the bracket located by a pin 642, bolt, or other fixing structure. The pivot pin 646 and translation connector 648 are thus positionable in an orientation transverse to the longitudinal extension of the patient support 610. As illustrated in FIG. 55, the translation connector 648 includes a slot 650 for receiving the pivot pin 646 therethrough. The translation connector 648 is slidable with respect to the pivot pin 646, as is described in greater detail below.

The translation connector subassembly 648 again includes a pivot connector 652. The pivot connector 652 is the same or substantially similar to the pivot connector described above with respect to FIGS. 4 and 5. The pivot connector 652 includes a slot sized and shaped for receiving an end connection 658 of the frame section 614. The pivot connector 652 further includes a through aperture or bore 60 running substantially perpendicular to the slot 654 and communicating therewith. As shown in FIG. 55, the aperture 660 is sized and shaped to receive a pivot pin 662 therethrough. The connector 648 also includes a through bore 660' that receives the pivot pin 662. The swiveable connection provided by the pin 662 allows for some forward and rearward lateral movement of the attached frame end connection 658 and thus the frame section 614, providing a degree of freedom and clearance needed for rotation or tilting the patient support 610 about a longitudinal axis of a patient. The slot 656 is sized and shaped to frictionally engage the frame end connection 658, thus securely fixing the end connection 658 to the pivot connector 652. The frame end connection 658 is in turn fixed to elongate frame members 667 and 668 (see FIG. 52) of the frame section 614. The frame members 667 and 668 are each hingedly connected to the hinge assembly 616 as described herein. Pivoting of the translation connector 648 with respect to the pin 646 provides for selected articulation, angulation or pivoting of the frame section 614 (that includes the end connection 658 and the frame members 667 and 668) and/or the entire support 610 with respect to the support pier or column 606.

With reference to FIG. 55, a bold dashed line that is parallel with the axis A1, intersects the transverse pivot pin 646. The pivot pin 646 is spaced a variable distance D1 from the A1 axis, wherein the distance D1 is measured between the A1 axis and the bold dashed line. As the patient support 610 is moved between various positions, the translation connector subassembly 648 is moved or translated along the pivot pin 646 at slot 650 and toward or away from the pier 606, as is indicated by the arrows D2. Accordingly, the distance D2 varies in cooperation with actuation of other components of the apparatus 601 that position the patient support 610. The translation connector subassembly 648 moves with respect to the pivot pin 646 in response to movement increasing and decreasing the inclination of the patient support 610 and positioning the patient support 610. When the frame 610 is inclined or placed in a breaking position or configuration (see FIGS. 49-51) the translation connector subassembly 648 moves away from the pier 606, thereby increasing the distance D1 between the axis A1 and the transverse axis. Upon returning to the planar position that is parallel with the floor (see FIGS. 48-52-53) the translation connector subassembly 648 moves toward the pier 606, thereby decreasing the distance D2. For example, when the patient support 610 is in a planar position parallel with the floor (FIGS. 48, 52 and 53), the translation connector 648 is in a starting position with respect to the pivot pin 646, and such that the distance D2 is a starting distance. When the patient support is moved into an upwardly breaking position (FIG. 49 or 54) or a downwardly breaking position (FIG. 51), and possibly a Trendelenburg position (FIG. 50), or a reverse-Trendelenburg position (not shown), the translation connector 648 is passively moved away from the pier 606 such that D2 is reduced relative to the starting distance. When the patient support 610 is returned to the initial planar position that is parallel with the floor, the translation connector 648 is passively moved back toward the starting position, and D2 is increased. Changes in the distance D2, or translation compensation, are in response to coordinated movements and positioning of the patient support 610. The amount of change in D2 is coordinated with the breaking of the hinges 616 and movement of other portions of the apparatus 601, such as by synchronizing electronics and a controller, such as but not limited to controller 618.

The patient support 610 is sized and shaped to reversibly receive thereon and engage a body support structure. Generally, numerous body support structures are attached to or fixed to the frames portions 612, 614 along their lengths. Such body support structures are know in the art and include, but are not limited to hip-thigh pads, generally 670, chest or torso support assemblies, generally 672, and chest or torso translation assemblies, generally 674. Detailed descriptions of several of these body support structures can be found in U.S. patent application Ser. No. 12/803,192, filed Jun. 21, 2010, U.S. patent application Ser. No. 13/956,728, filed Aug. 1, 2013, and U.S. patent application Ser. No. 14/012,434, filed Aug. 28, 2013, each of which is incorporated by reference herein in its entirety.

The hip-thigh pads 670 are generally attached adjacent to the hinges 616. In some embodiments, the hip-thigh pads 670 are incorporated into or include the hinges 616. The placement of the upper body supports depends upon the location of the hip-thigh pads 670 and the length of the patient's spine. Generally, it is desirable to maintain a substantially constant distance D3 (see FIG. 48) between the patient's hips, or the hip pads 670, and an upper body support, such as the chest support 672 or torso trolley 674. Upward and downward breaking of the hinges 616 is associated with flexion and extension, respectively, of the patient's hips. Therefore, keeping distance D3 substantially constant advantageously prevents excessive, or undesirable, pulling and compression of the patient's spine during upward and downward breaking of the hinges 616.

In some embodiments, such as is shown in FIGS. 48-51, both the hip-thigh pads 670 and the upper body support are located on the same side of the hinges 616. For example, the hip-thigh pads 670 and the upper body support may be attached to the frame portion 614. Accordingly, since the hip-thigh pads 670 are stationary, it is acceptable to support the patient's upper body with a stationary upper body support, such as the chest support 672, which is fixed to and locks onto the frame 614.

In other embodiments, the hip-thigh pads 670 and the upper body support are located on the opposite side of the hinges 616, or the hinges 616 include the hip-thigh pads. For example, as shown in FIG. 53, the hip-thigh pads 670 are attached to the frame 612 such that they are located adjacent to the hinges 616, and the torso trolley 674 is attached to the frame 614. The torso trolley 674 includes upper body support portion 676 and an actuator 678. The actuator 678 moves the upper body support portion 676 longitudinally, as is indicated by the arrow 680, so as to maintain the distance D3 substantially constant. Movement of upper body support portion 676 by the actuator 678 is coordinated, or synchronized, with the movements of the hinges 616 by software and a controller, such as but not limited to controller 618.

Thus, if the hip-thigh pads 670 are located on the opposite side of the hinges 616 from the upper body support, and the upper body support is stationary, the distance D3 will vary (i.e., increase and decrease) during actuation of the hinges 616. However, if the upper body support is longitudinally movable, such as is the torso trolley 674, the upper body support can move longitudinally along the frame 614 at a suitable rate and in a direction that is sufficient to keep the distance D3 substantially constant. For example, when the frame 610 is in a planar configuration, the torso trolley 674 is attached to the frame 614 at a location along the length of the frame 614, such that the upper body support portion 676 is spaced an initial distance of D3 from the hip-thigh pads 670. When the hinges 616 are actuated and moved to an upwardly or downwardly breaking position or configuration, the hip-thigh pads 670 swing away from their initial position. If the upper body support is stationary, like the chest support 672, the distance D3 would be increased. The torso trolley 674 avoids this problem, because as the hip-thigh pads 670 swing away from their initial position, the actuator 678 of the torso trolley 674 moves the body support 676 toward the hinges 616. The body support 676 is moved at a rate sufficient to keep the distance D3 substantially constant, and such movement is coordinated and synchronized with the movements of the hinges 616. When the hinges 616 are moved back to their starting position, wherein the patient support 610 is planar, the hip-thigh pads 670 swing back toward their initial position. Simultaneously, the actuator 678 moves the upper body support 676 away from the hinges 616 at a rate sufficient to keep the distance D3 substantially constant.

It is noted that the components of the apparatus 601 cooperate, or work in concert, perform several functions at the same time, so as to move or place a patient's body in a desirable position for performing the surgical procedure. These functions include, but are not limited to, simultaneously maintaining the surgical site at a substantially constant height H, maintaining the surgical site at a substantially constant location along longitudinal axis of the apparatus 601, and enabling or allowing movement and positioning of the patient's body during the surgical procedure, such as (but not limited to) by upward and downward breaking, inclination and tilting of the patient support 610.

It is noted that providing for translation of the patient support 610 at both outer ends thereof, such as is provided by the second base 617, and the translation connector 648 and angulation subassembly 267 enables the hinges 616 to be substantially stationary in a longitudinal direction, such that the hinges 616 do not move substantially toward either the operating table support structure 604 or the pier 606. Preventing the hinges 616 from moving longitudinally substantially prevents the surgical site, on the patient, from moving longitudinally toward either end of the apparatus 601. Many surgeries are performed under magnification and/or in conjunction with continuous imaging of the surgical site. As is known in the art, even small movements of the surgical site parallel with the longitudinal axis of the apparatus 601 is substantially disruptive of such surgical procedures. Accordingly, longitudinal translation at both ends of the apparatus 1 provides significant advantages over surgical tables that include such longitudinal translation at only one end thereof.

It is to be understood that while certain forms of the present invention have been illustrated and described herein, it is not to be limited to the specific forms or arrangement of parts described and shown.

What is claimed is:

1. A patient positioning system comprising:
   a base including spaced apart first and second columns;
   a first patient support extending along a first longitudinal axis between opposite first and second ends, the first end being coupled to the first column;
   a second patient support extending along a second longitudinal axis between opposite first and second ends, the first end of the second patient support being coupled to the second column, the second end of the second patient support being connected to the second end of the first patient support by a hinge, the patient positioning system comprising a rod having an end that is connected to the second patient support and an opposite end that is connected to the hinge, the rod being extendable and retractable to pivot the second patient support relative to the first patient support about the hinge; and
   a roll mechanism coupled to the first column and the first patient support, the roll mechanism being configured to rotate the first patient support about the first longitudinal axis.

2. The patient positioning system of claim 1, wherein the hinge allows the patient positioning system to move between a first orientation in which the second longitudinal axis is co-planar with the first longitudinal axis and a second orientation in which the second longitudinal axis extends transverse to the first longitudinal axis.

3. The patient positioning system of claim 1, wherein the roll mechanism is configured to rotate the first patient support at least ninety degrees about the first longitudinal axis.

4. The patient positioning system of claim 1, wherein the roll mechanism is a first roll mechanism and the patient positioning system further comprises a second roll mechanism coupled to the second column and the second patient support, the second roll mechanism being configured to rotate the second patient support about the second longitudinal axis.

5. The patient positioning system of claim 4, wherein the first roll mechanism is configured to rotate the first patient support at least ninety degrees about the first longitudinal axis and the second roll mechanism is configured to rotate the second patient support at least ninety degrees about the second longitudinal axis.

6. The patient positioning system of claim 1, wherein the first end of the first patient support is releasably coupled to the first column.

7. The patient positioning system of claim 1, wherein the first end of the first patient support is releasably coupled to the first column by a removable pin.

8. The patient positioning system of claim 1, wherein the first column comprises a plurality of spaced apart apertures along a length of the first column, the patient positioning system comprising a pin configured to be removably positioned in one of the apertures and extend through the first patient support to releasably couple the first patient support to the first column.

9. The patient positioning system of claim 8, wherein the pin is configured to be removed from one of the apertures and inserted into another one of the apertures to adjust a position of the first end of the first patient support along the height of the first column.

10. The patient positioning system of claim 1, wherein the first end of the first patient support is releasably coupled to the first column and the first end of the second patient support is releasably coupled to the second column.

11. The patient positioning system of claim 1, wherein the first end of the first patient support is releasably coupled to the first column by a first removable pin and the first end of the second patient support is releasably coupled to the second column by a second removable pin.

12. The patient positioning system of claim 11, wherein the first removable pin extends parallel to the second removable pin.

13. The patient positioning system of claim 1, wherein the first column comprises a plurality of spaced apart first apertures along a length of the first column and the second column comprises a plurality of spaced apart second apertures along a length of the second column, the patient positioning system comprising a first pin configured to be removably positioned in one of the first apertures and extend through the first patient support to releasably couple the first patient support to the first column, the patient positioning system comprising a second pin configured to be removably positioned in one of the second apertures and extend through the second patient support to releasably couple the second patient support to the second column.

14. The patient positioning system of claim 13, wherein the first pin is configured to be removed from one of the first apertures and inserted into another one of the first apertures to adjust a position of the first end of the first patient support along the height of the first column and the second pin is configured to be removed from one of the second apertures and inserted into another one of the second apertures to adjust a position of the first end of the second patient support along the height of the second column.

15. The patient positioning system of claim 1, wherein the first column comprises a plurality of spaced apart apertures along a length of the first column, the patient positioning system comprising a pin configured to be removably positioned in one of the apertures and extend through an elongated slot of the first patient support to releasably couple the first patient support to the first column, the pin being configured to be removed from one of the apertures and inserted into another one of the apertures and the slot to adjust a position of the first end of the first patient support along the height of the first column.

16. The patient positioning system of claim 1, wherein:
the first column comprises a plurality of spaced apart first apertures along a length of the first column, the patient positioning system comprising a first pin configured to be removably positioned in one of the first apertures and extend through a first elongated slot of the first patient support to releasably couple the first patient support to the first column, the first pin being configured to be removed from one of the first apertures and the slot and inserted into another one of the first apertures to adjust a position of the first end of the first patient support along the height of the first column; and
the second column comprises a plurality of spaced apart second apertures along a length of the second column, the patient positioning system comprising a second pin configured to be removably positioned in one of the second apertures and extend through a second elongated slot of the second patient support to releasably couple the second patient support to the second column, the second pin being configured to be removed from one of the second apertures and inserted into another one of the second apertures to adjust a position of the second end of the first patient support along the height of the second column.

17. The patient positioning system of claim 1, wherein the hinge comprises a first part coupled to the second end of the first patient support and a second part coupled to the second end of the second patient support, the first part comprising an extension rotatably disposed in an opening of the second part such that the second part is rotatable relative to the first part about the extension.

18. A patient positioning system comprising:
a base including spaced apart first and second columns;
a first patient support extending along a first longitudinal axis between opposite first and second ends, the first end being releasably coupled to the first column by a first removable pin;
a second patient support extending along a second longitudinal axis between opposite first and second ends, the first end of the second patient support being releasably coupled to the second column by a removable second pin, the second end of the second patient support being connected to the second end of the first patient support by a hinge, the patient positioning system comprising a rod having an end that is connected to the second patient support and an opposite end that is connected to the hinge, the rod being extendable and retractable to pivot the second patient support relative to the first patient support about the hinge, the hinge comprising a first part coupled to the second end of the first patient support and a second part coupled to the second end of the second patient support, the first part comprising an extension rotatably disposed in an opening of the second part such that the second part is rotatable relative to the first part about the extension;
a first roll mechanism coupled to the first column and the first patient support, the first roll mechanism being configured to rotate the first patient support about the first longitudinal axis; and
a second roll mechanism coupled to the second column and the second patient support, the second roll mechanism being configured to rotate the second patient support about the second longitudinal axis,
wherein the hinge allows the patient positioning system to move between a first orientation in which the second longitudinal axis is co-planar with the first longitudinal axis and a second orientation in which the second longitudinal axis extends transverse to the first longitudinal axis.

19. The patient positioning system of claim 1, wherein the rod includes a pair of spaced apart pull rods.

20. A patient positioning system comprising:
a base including spaced apart first and second columns;
a first patient support extending along a first longitudinal axis between opposite first and second ends, the first end being coupled to the first column by a first angulation subassembly such that the first end is pivotable relative to the first column about an axis that extends perpendicular to the first longitudinal axis and the first end is spaced apart from the first column by the first angulation subassembly;
a second patient support extending along a second longitudinal axis between opposite first and second ends, the first end of the second patient support being coupled to the second column by a second angulation subassembly such that the first end of the second patient support is pivotable relative to the second column about an axis that extends perpendicular to the second longitudinal axis and the first end of the second patient support is spaced apart from the second column by the second angulation subassembly, the second end of the second patient support being connected to the second end of the first patient support by a hinge, the patient positioning system comprising a rod having an end that is connected to the second patient support and an opposite end that is connected to the hinge, the rod being extendable and retractable to pivot the second patient support relative to the first patient support about the hinge; and a roll mechanism coupled to the first column and the first patient support, the roll mechanism being configured to rotate the first patient support about the first longitudinal axis.

* * * * *